(12) United States Patent
Neelapu et al.

(10) Patent No.: US 9,290,541 B2
(45) Date of Patent: Mar. 22, 2016

(54) TCL1 PEPTIDES FOR IMMUNOTHERAPY

(71) Applicant: Board of Regents, The University of Texas System, Austin, TX (US)

(72) Inventors: Sattva S. Neelapu, Pearland, TX (US); Jinsheng Weng, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/358,896

(22) PCT Filed: Nov. 19, 2012

(86) PCT No.: PCT/US2012/065866
§ 371 (c)(1),
(2) Date: May 16, 2014

(87) PCT Pub. No.: WO2013/075105
PCT Pub. Date: May 23, 2013

(65) Prior Publication Data
US 2014/0348902 A1    Nov. 27, 2014

Related U.S. Application Data

(60) Provisional application No. 61/561,555, filed on Nov. 18, 2011.

(51) Int. Cl.
| | | |
|---|---|---|
| *C07K 14/00* | (2006.01) | |
| *A61K 39/00* | (2006.01) | |
| *A61K 38/08* | (2006.01) | |
| *A61K 38/10* | (2006.01) | |
| *A61K 38/16* | (2006.01) | |
| *A61K 45/06* | (2006.01) | |
| *C07K 7/06* | (2006.01) | |
| *C07K 7/08* | (2006.01) | |

(52) U.S. Cl.
CPC .............. *C07K 14/00* (2013.01); *A61K 38/08* (2013.01); *A61K 38/10* (2013.01); *A61K 38/16* (2013.01); *A61K 39/0011* (2013.01); *A61K 45/06* (2013.01); *C07K 7/06* (2013.01); *C07K 7/08* (2013.01)

(58) Field of Classification Search
None
See application file for complete search history.

(56) References Cited

U.S. PATENT DOCUMENTS

| | | | |
|---|---|---|---|
| 5,985,598 A | 11/1999 | Russo et al. | |
| 7,175,995 B1 | 2/2007 | Russo et al. | |
| 7,749,715 B2 | 7/2010 | Russo et al. | |
| 7,910,109 B2 | 3/2011 | Carroll et al. | |

FOREIGN PATENT DOCUMENTS

| | | |
|---|---|---|
| WO | WO 96-13514 | 5/1996 |
| WO | WO 00-32769 | 6/2000 |
| WO | WO 00-55169 | 9/2000 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Strome et al., The Oncologist, 2007; 12:1084-95.*
Brand et al., Anticancer Res. 2006; 26:463-70.*
Engelhard, Current Opinion in Immunology vol. 6 p. 13 (1994).*
Guo, et al Nature vol. 360 p. 384 (1992).*
Rammensee et al, Immunogenetics vol. 41 p. 178 (1995).*
Shastri et al J. Immunol. vol. 1995 vol. 155 p. 4339.*
"TCL1A overexpression linked to poor outcome in DLCL patients", *Cancer Vaccine Week*, Mar. 21, 2005.
Aggarwal et al., "TCL1A expression delineates biological and clinical variability in B-cell lymphoma", *Modern Pathology*, 22:206-215, 2009.
Bendandi et al.,"Complete molecular remissions induced by patient-specific vaccination plus granulocyte-monocyte colony-stimulating factor against lymphoma", *Nat. Med.*, 5:1171-1177, 1999.
Bertinetti et al., "Phase I trial of a novel intradermal idiotype vaccine in patients with advanced B-cell lymphoma: specific immune responses despite profound immunosuppression", *Cancer Res.*, 66:4496-4502, 2006.
Bijker et al.,"CD8+ CTL priming by exact peptide epitopes in incomplete Freund's adjuvant induces a vanishing CTL response, whereas long peptides induce sustained CTL reactivity", *J. Immunol.*, 179:5033-5040, 2007.
Blanchard and Shastri, "Coping with loss of perfection in the MHC class I peptide repertoire", *Curr. Opin. Immunol.*, 20:82-88, 2008.
Burrows et al., "Have we cut ourselves too short in mapping CTL epitopes?", *Trends Immunol.*, 27:11-16, 2006.
Celluzzi et al., "Peptide-pulsed dendritic cells induce antigen-specific CTL-mediated protective tumor immunity", *J. Exp. Med.*, 183: 283-287, 1996.
Cheson and Leonard, "Monoclonal antibody therapy for B-cell non-Hodgkin's lymphoma", *N. Eng. J. Med.*, 359:613-626, 2008.
Coiffier et al., "CHOP chemotherapy plus rituximab compared with CHOP alone in elderly patients with diffuse large-B-cell lymphoma", *N. Eng. J. Med.*, 346:235-242, 2002.
Collins et al., "Three-dimensional structure of a peptide extending from one end of a class I MHC binding site", *Nature*, 371:626-629, 1994.
Di Nicola et al., "Vaccination with autologous tumor-loaded dendritic cells induces clinical and immunologic responses in indolent B-cell lymphoma patients with relapsed and measurable disease: a pilot study", *Blood*, 113:18-27, 2009.

(Continued)

*Primary Examiner* — Sheela J Huff
(74) *Attorney, Agent, or Firm* — Parker Highlander PLLC

(57) ABSTRACT

Provided are TCL1 peptides that bind to MHC I (HLA-A2) on tumor cells or other antigen-presenting cells and are recognized by T-cell receptors on T cells. The TCL1 peptides may be therapeutically used to treat a cancer, such as a B cell malignancy, leukemia, or lymphoma. Methods for expanding a population of T cells that target TCL1 are also provided.

18 Claims, 26 Drawing Sheets

(56) References Cited

OTHER PUBLICATIONS

Dudley et al., "Generation of tumor-infiltrating lymphocyte cultures for use in adoptive transfer therapy for melanoma patients", *J. Immunol.*, 26(4):332-342, 2003.
Gritti et al., "Transgenic mice for MTCP1 develop T-cell prolymphocytic leukemia", *Blood*, 92:368-373, 1998.
Guo et al., "Different length peptides bind to HLA-Aw68 similarly at their ends but bulge out in the middle", *Nature*, 360:364-366, 1992.
Hawkins et al., "Development of adoptive cell therapy for cancer: a clinical perspective", *Hum. Gene Ther.*, 21(6):665-72, 2010.
Herling et al., "High TCL1 are a marker of B-cell receptor pathway responsiveness and adverse outcome in chronic lymphocytic leukemia", *Blood*, 114:4675-4686, 2009.
Herling et al., "High TCL1 express ion and intact T-cell receptor signaling define a hyperproliferative subset of T-cell prolymphocytic leukemia", *Blood*, 111(1): 328-337, 2007.
Herling et al., "TCL1 in B-cell tumors retains its normal b-cell pattern of regulation and is a marker of differentiation stage", *Am. J. Surg. Pathol.*, 31:1123-1129, 2007.
Hida et al., "A simple culture protocol to detect peptide-specific cytotoxic T lymphocyte precursors in the circulation", *Cancer Immunol. Immunotherapy*, 51:219-228, 2002.
Houot and Levy, "Vaccines for lymphomas: idiotype vaccines and beyond", *Blood Rev.*, 23:137-142, 2009.
Hoyer et al., "Dysregulated TCL1 promotes multiple classes of mature B cell lymphoma", *Proc. Natl. Acad. Sci. USA*, 99:14392-14397, 2002.
Inogès et al., "Clinical benefit associated with idiotypic vaccination in patients with follicular lymphoma", *J. Natl. Cancer Inst.*, 98:1292-1301, 2006.
Irvine et al., "Direct observation of ligand recognition by T cells", *Nature*, 419:845-849, 2002.
Kang et al., "Inhibition of self-binding antibodies (autobodies) by a VH-derived peptide", *Science*, 240:1034-1036, 1988.
Kwak et al., "Induction of immune responses in patients with B-cell lymphoma against the surface-immunoglobulin idiotype expressed by their tumors", *N. Eng. J. Med.*, 327:1209-1215, 1992.
Laine et al., "The protooncogene TCL1 is an Akt kinase coactivator", *Molec. Cell*, 6:395-407, 2000.
Lee et al., "A novel strategy for rapid and efficient isolation of human tumor-specific CD4(+) and CD8(+) T-cell clones", *J. Immunol. Methods*, 331:13-26, 2008.
Malyguine et al., "A modified human ELISPOT assay to detect specific responses to primary tumor cell targets", *J. Transl. Med.*, 2(1):9, 2004.
Marcus et al., "CVP chemotherapy plus rituximab compared with CVP as first-line treatment for advanced follicular lymphoma", *Blood*, 105:1417-1423, 2005.
Maus et al., "Ex vivo expansion of polyclonal and antigen-specific cytotoxic T lymphocytes by artificial APCs expressing ligands for the T-cell receptor, CD28 and 4-1BB", *Nat. Biotech.*, 20:143-148, 2002.
McLaughlin et al., "Rituximab chimeric anti-CD20 monoclonal antibody therapy for relapsed indolent lymphoma: half of patients respond to a four-dose treatment program", *J. Clin. Oncol.*, 16:2825-2833, 1998.
Melief and van der Burg, "Immunotherapy of established (pre)malignant disease by synthetic long peptide vaccines", *Nat. Rev. Cancer*, 8:351-360, 2008.
Narducci et al., "Regulation of TCL1 expression in b- and t-cell lymphomas and reactive lymphoid tissues", *Cancer Research*, 60:2095-2100, 2000.
Narducci et al., "TCL1 is overexpressed in patients affected by adult T-cell leukemias", *Cancer Res.*, 57:5452-5456, 1997.
Narducci et al., "The murine Tcl1 oncogene: embryonic and lymphoid cell expression", *Oncogene*, 15:919-926, 1997a.
Narducci et al., "TCL1 participates in early embryonic development and is overexpressed in human seminomas", *Proc. Natl. Acad. Sci. USA*, 99:11712-11717, 2002.

Navarrete et al., "Upfront immunization with autologous recombinant idiotype Fab fragment without prior cytoreduction in indolent B-cell lymphoma", *Blood*, 117:1483-1491, 2011.
Neelapu and Kwak, "Vaccine therapy for b-cell lymphomas: next-generation strategies", *Hematology*, pp. 243-249, 2007.
Neelapu et al., "Vaccine-induced tumor-specific immunity despite severe B-cell depletion in mantle cell lymphoma", *Nat. Med.*, 11:986-991, 2005.
Nestle et al., "Vaccination of melanoma patients with peptide- or tumor lysate-pulsed dendritic cells", *Nat. Med.*, 4:328, 1998.
Park and Neelapu, "Developing idiotype vaccines for lymphoma: from preclinical studies to phase III clinical trials", *Br. J. Haemat.*, 142:179-191, 2008.
PCT International Preliminary Report on Patentability issued in International Application No. PCT/US2012/065866, mailed May 30, 2014.
PCT International Search Report and Written Opinion issued in International Application No. PCT/US2012/065866, mailed Mar. 13, 2013.
Pekarsky et al., "Tell functions as a transcriptional regulator and is directly involved in the pathogenesis of CLL", *Proc. Natl. Acad. Sci. USA*, 105:19643-19648, 2008.
Quintarelli et al., "High-avidity cytotoxic T lymphocytes specific for a new PRAME-derived peptide can target leukemic and leukemic-precursor cells", *Blood*, 117:3353-3362, 2011.
Ramuz et al., "Identification of TCL1A as an immunohistochemical marker of adverse outcome in diffuse large B-cell lymphomas", *Int. J Oncol.*, 26:151-157, 2005.
Ribas et al., "Determinant spreading and tumor responses after peptide-based cancer immunotherapy", *Trends Immunol.*, 24:58-61, 2003.
Riddell et al., "The use of anti-CD3 and anti-CD28 monoclonal antibodies to clone and expand human antigen-specific T cells", *J. Immunol.*, 128(2):189-201, 1990.
Said et al., "TCL1 oncogene expression in B cell subsets from lymphoid hyperplasia and distinct classes of B cell lymphoma", *Lab. Invest.* 81:555-564, 2001.
Samino et al., "A long N-terminal-extended nested set of abundant and antigenic major histocompatibility complex class I natural ligands from HIV envelope protein", *J. Biol. Chem.*, 281:6358-6365, 2006.
Schuster et al., "Vaccination with patient-specific tumor-derived antigen in first remission improves disease-free survival in follicular lymphoma", *J. Clin. Oncol.*, 29(20):2787-94, 2011.
Skull and Kemp, "Treatment of hypogammaglobulinaemia with intravenous immunoglobulin, 1973-93", *Arch. Dis. Child.*, 74:527-530, 1996.
Stryhn et al., "Longer peptide can be accommodated in the MHC class I binding site by a protrusion mechanism", *Eur. J. Immunol.*, 30:3089-3099, 2000.
Teitell, "The TCL1 family of oncoproteins: co-activators of transformation", *Nat. Rev. Cancer*, 5:640-648, 2005.
Timmerman et al., "Idiotype-pulsed dendritic cell vaccination for B-cell lymphoma: clinical and immune responses in 35 patients", *Blood*, 99:1517-1526, 2002.
Virgilio et al., "Deregulated expression of TCL1 causes T cell leukemia in mice", *Proc. Natl. Acad. Sci. USA*, 95:3885-3889, 1998.
Weng et al., "TCL1: a shared tumor-associated antigen for immunotherapy against B-cell lymphomas", *Blood*, 120(8): 1613-1623, 2012.
Young and Inaba, "Dendritic cells as adjuvants for class I major histocompatibility complex-restricted antitumor immunity", *J. Exp. Med.*, 183(1):7-11, 1996.
Zwaveling et al., "Established human papillomavirus type 16-expressing tumors are effectively eradicated following vaccination with long peptides", *J Immunol.*, 169:350-358, 2002.

\* cited by examiner

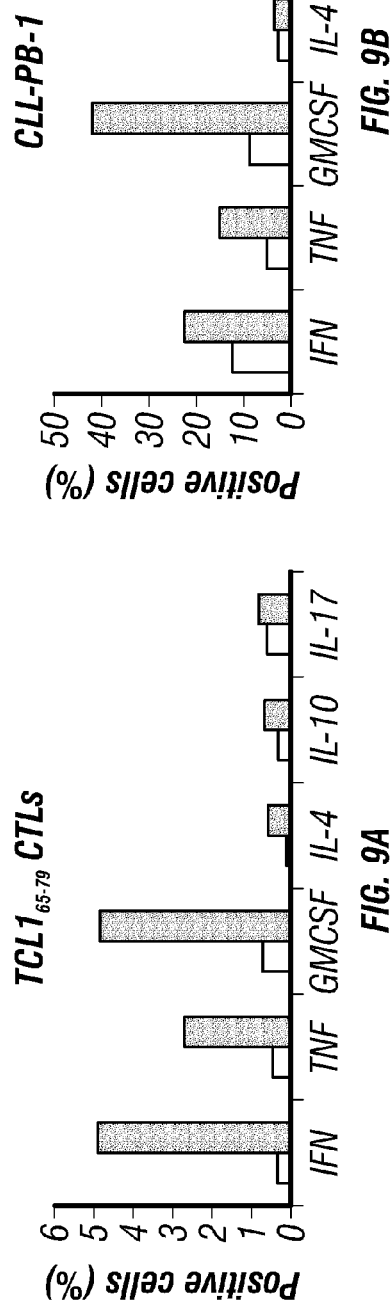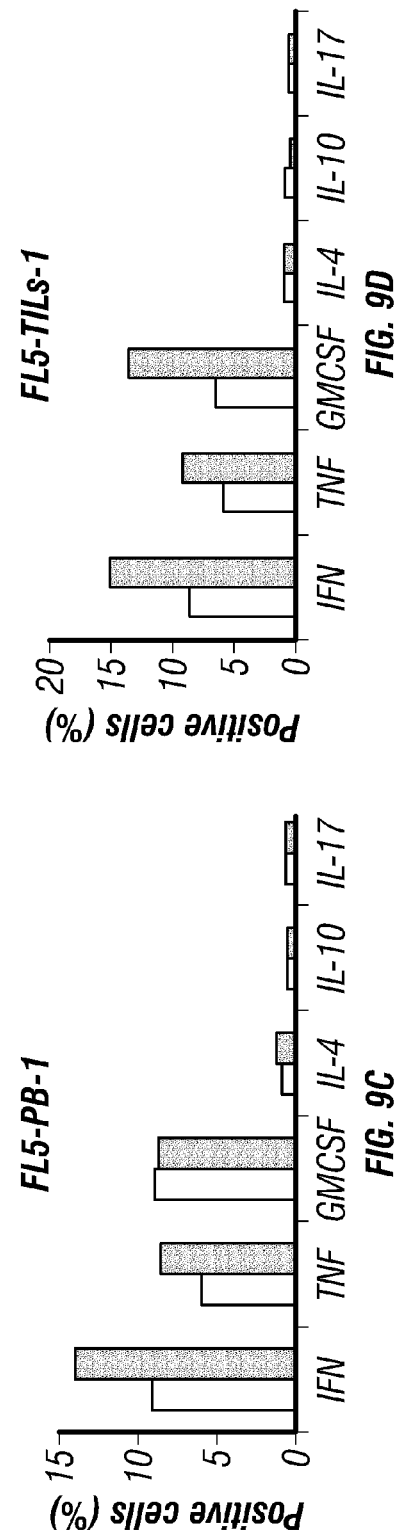
FIG. 9A  TCL1₆₅₋₇₉ CTLs
FIG. 9B  CLL-PB-1
FIG. 9C  FL5-PB-1
FIG. 9D  FL5-TILs-1

TCL1 PEPTIDES FOR IMMUNOTHERAPY

This application is a national phase application under 35 U.S.C. §371 of International Application No. PCT/US2012/065866, filed Nov. 19, 2012, which claims the benefit of U.S. Provisional Patent Application No. 61/561,555, filed Nov. 18, 2011, the entirety of each of which is incorporated herein by reference.

This application claims the benefit of U.S. Provisional Patent Application No. 61/561,555, filed Nov. 18, 2011, the entirety of which is incorporated herein by reference.

BACKGROUND OF THE INVENTION

1. Field of the Invention

The present invention relates generally to the fields of molecular biology, immunology, and medicine. More particularly, it concerns epitopes of TCL1 that are recognized by T cells and may be used to treat a cancer.

2. Description of Related Art

Malignancies of B-cell origin are typically responsive to combination chemotherapy and complete remissions can be induced in many patients; nonetheless, relapse continues to be a significant clinical problem. The use of rituximab, an anti-CD20 monoclonal antibody in combination with chemotherapy has improved the overall and complete response rates, progression-free survival, overall survival, and curability of patients with B-cell non-Hodgkin's lymphomas (Marcus et al., 2005; Cheson and Leonard; Coiffier et al., 2002). However, relapse remains a significant cause of treatment failure and novel treatments are needed to eradicate minimal residual disease to further improve clinical outcome in these patients.

While immunotherapy with idiotype vaccines may offer promise for treatment of B-cell malignancies, identification of novel lymphoma-associated antigens that are widely expressed is necessary to overcome the barriers of patient-specific idiotype vaccines. Therapeutic agents used to eradicate minimal residual disease should ideally be directed at different targets and have different mechanisms of action than agents used in induction therapy. They should also be safe with minimal adverse effects since they may need to be administered as maintenance therapy over several months. Therapeutic vaccines may provide many of these desirable features as they can target different antigens on the lymphoma tumor cells than those targeted by rituximab or chemotherapy agents, and they have been observed to be safe and well tolerated (Houot and Levy, 2009; Park and Neelapu, 2008). Furthermore, by inducing immunological memory and polyclonal humoral and cellular immune responses, vaccines may potentially produce a sustained antitumor effect, and unlike monoclonal antibodies, they may prevent the emergence of antigen-loss variants. Thus, therapeutic vaccines against lymphomas can be complementary to passive immunotherapeutic agents such as monoclonal antibodies and cytotoxic chemotherapeutic agents and could be ideal for eradicating minimal residual disease.

Several groups have used the clonal tumor immunoglobulin expressed on the surface of mature B-cell malignancies, termed idiotype, as a tumor-specific antigen for development of therapeutic vaccines against lymphomas (Di Nocola et al., 2009; Timmerman et al., 2002; Navarrete et al., 2011; Bertinetti et al., 2006; Inoges et al., 2006; Neelapu et al., 2005; Malyguine et al., 2004; Bendandi et al., 1999; Kwak et al., 1992). Idiotype vaccines were shown to be safe and induced sustained antitumor antibody and CD4$^+$ and CD8$^+$ T-cell responses in patients with follicular lymphoma (FL), chronic lymphocytic leukemia (CLL), mantle cell lymphoma (MCL), and diffuse large B-cell lymphoma (DLBCL) (Di Nocola et al., 2009; Timmerman et al., 2002; Navarrete et al., 2011; Bertinetti et al., 2006; Inoges et al., 2006; Neelapu et al., 2005; Malyguine et al., 2004; Bendandi et al., 1999; Kwak et al., 1992). Furthermore, idiotype vaccines induced molecular remissions when administered after standard chemotherapy (Bendandi et al., 1999). A recently completed randomized, double blind, multicenter phase III clinical trial showed that idiotype vaccination improves disease-free survival when administered in the setting of minimal residual disease in FL, providing proof of principle that therapeutic vaccines can improve clinical outcome in these patients (Schuster et al., 2011). However, a major limitation of idiotype vaccines is the requirement for a custom-made product for each patient that makes the manufacturing of the vaccine expensive, laborious, and time-consuming. To overcome these difficulties, there is a clear need for the identification of novel lymphoma-associated antigens that are shared between patients and widely expressed in multiple B-cell malignancies.

SUMMARY OF THE INVENTION

The present invention overcomes limitations in the prior art by providing new MHC class I epitopes of TCL1. The antigenic TCL1 peptides may be used in various cancer therapies, e.g., as a cancer vaccine or in an adoptive immunotherapy. Antibodies, such as therapeutic humanized antibodies, may also be generated that selectively bind one or more of the TCL1 peptides or the complex formed by the binding of a TCL1 peptide and HLA-A2. The TCL1 peptides may be used to treat a B cell malignancy, such as a leukemia or a lymphoma. The present invention is based, in part, on the discovery that peptides of the intracellular protein TCL1 are provided by MHC I (HLA-A2) on the surface of tumor cells that are recognized by T-cell receptors on T cells. In various aspects, TCL1 peptides are provided that can bind MHC I (HLA-A2) and can be recognized by T-cell receptors on T cells. The TCL1 peptides may be therapeutically used to treat a cancer, such as a B cell malignancy, leukemia, or lymphoma. Methods for expanding a population of T cells that target TCL1 are also provided.

As shown in the below examples, expression of TCL1 in B-cell lymphomas and normal tissues was characterized, and TCL1$_{71-78}$ was identified as the minimal immunogenic epitope that binds to HLA-A*0201 (HLA-A2), and it was observed that cytotoxic T lymphocytes (CTL) specific to this peptide can efficiently kill lymphoma cell lines and primary human lymphoma cells. These results suggest that TCL1 is naturally processed and presented on the surface of primary lymphoma cells for recognition by CTL in an HLA-restricted manner and can potentially serve as a shared lymphoma-associated antigen for therapeutic vaccine development against multiple B-cell malignancies.

An aspect of the present invention relates to an isolated peptide 45 amino acids in length or less and comprising the sequence of TCL1$_{65-78}$ (SEQ ID NO:2) or TCL1$_{71-78}$ (SEQ ID NO:11) or a sequence having at least 90% identity to TCL1$_{65-78}$ (SEQ ID NO:2) or TCL1$_{71-78}$ (SEQ ID NO:11), wherein the peptide selectively binds HLA-A2 or HLA-A*0201. In some embodiments, the peptide is 15 amino acids in length or less. The peptide may comprises or consist of TCL1$_{65-79}$ (SEQ ID NO:1). The peptide may comprise TCL1$_{70-79}$ (SEQ ID NO:7). The peptide may be comprised in a pharmaceutical preparation. The pharmaceutical preparation may be formulated for parenteral administration, intravenous injection, intramuscular injection, inhalation, or subcutaneous injection. In some embodiments, the peptide is comprised in a liposome, lipid-containing nanoparticle, or in a lipid-based carrier. The pharmaceutical preparation may be formulated for injection or inhalation as a nasal spray. The peptide may be comprised in a cell culture media. The peptide may be produced via peptide synthesis. In other embodiments, the peptide may be recombinantly produced. In some aspects, the peptide may be comprised in a composition or a pharmaceutical composition, for use in therapeutic treatment of a disease, such as for example cancer.

Another aspect of the present invention relates to a method of treating a cancer in a mammalian subject, comprising administering to the subject an effective amount of a TCL1 peptide of the present invention. The peptide may be comprised in a pharmaceutical preparation. The pharmaceutical preparation may be formulated for parenteral administration, intravenous injection, intramuscular injection, inhalation, or subcutaneous injection. In some embodiments, the subject is a human. The cancer may be selected from the group consisting of a leukemia, a lymphoma, or a B-cell malignancy, or a B-cell lymphoma. In some embodiments, the cancer is a B-cell malignancy selected from the group consisting of follicular lymphoma (FL), chronic lymphocytic leukemia (CLL), mantle cell lymphoma (MCL), diffuse large B-cell lymphoma (DLBCL), and splenic marginal zone lymphoma (SMZL). The subject may be administered a second anti-cancer therapy, such as, e.g., a chemotherapy, a radiotherapy, an immunotherapy, or a surgery. The peptide may be administered to the subject in an amount effective to promote cytotoxic T lymphocytes (CTL) in the subject to lyse or kill cancerous cells in the subject.

Yet another aspect of the present invention relates to a method for inducing a population of T cells to proliferate, comprising contacting T cells with a peptide of claim 1 in an amount sufficient to bind a HLA-A*0201 or a HLA-A2 in the T cells and promote proliferation of one or more of the T cells. The T cells may be cytotoxic T lymphocytes (CTL) or CD8+ T cells. The method may be further defined as an in vitro method. The method may further comprising administering the T cells to a subject after said proliferation. The subject may be a human.

Another aspect of the present invention relates to a method of promoting an immune response in a subject against TCL1, comprising administering to the subject a peptide of claim 1 in an amount effective to cause proliferation of T cells that selectively target TCL1. The T cells may be cytotoxic T lymphocytes. The subject may be a human. The subject may have a cancer, such as, e.g., a leukemia, a lymphoma, or a B-cell malignancy, or a B-cell lymphoma. In other embodiments, the subject does not have a cancer.

Yet another aspect of the present invention relates to a isolated nucleic acid encoding a TCL1 peptide of the present invention. Another aspect of the present invention relates to a vector comprising a contiguous sequence consisting of the nucleic acid segment.

Another aspect of the present invention relates to an isolated antibody that selectively binds to a TCL peptide of the present invention. The antibody may be a monoclonal antibody, may be comprised in polyclonal antisera, or may be an antibody fragment. In some embodiments, the antibody is a human or humanized antibody.

Yet another aspect of the present invention relates to an isolated antibody that selectively binds to a peptide—HLA-A2 complex, wherein the peptide—HLA-A2 complex comprises a TCL1 peptide of the present invention bound to a HLA-A2. The antibody may be a monoclonal antibody, may be comprised in polyclonal antisera, or may be an antibody fragment. In some embodiments, the antibody is a human or humanized antibody.

Another aspect of the present invention relates to a kit comprising a TCL1 peptide of the present invention in a container means. The peptide may be comprised in a pharmaceutical preparation, such as, e.g., a pharmaceutical preparation formulated for parenteral administration or inhalation. The peptide may be comprised in a cell culture media.

HLA-A2 refers to the human leukocyte antigen serotype A2 and is also referred to as HLA-A*02. Several serotypes of the gene products of many HLA-A*02 alleles are well known, including HLA-A*0201, *0202, *0203, *0206, *0207, and *0211 gene products.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A, FIG. 1C) Total RNA was extracted from normal human tissues, normal human peripheral blood B and T cells, and from primary human lymphoma cells, reverse transcribed into cDNA and quantitative PCR was performed for TCL1 and β-actin. (FIG. 1A) The expression of TCL1 mRNA relative to β-actin is shown in normal human tissues. (FIG. 1C) The expression of TCL1 mRNA in primary human lymphoma cells is shown relative to TCL1 expression in normal human peripheral blood B cells. Horizontal lines represent the median value for each group. P value on the top of graph represents comparison between normal donor B cells and all lymphomas. P values below the graph represent comparison between normal donor B cells and each lymphoma subtype. All P values were calculated by two-tailed Student's t test. (FIG. 1B, FIG. 1D) The expression of TCL1 mRNA in normal human tissues (FIG. 1B) and different human lymphoma subtypes (FIG. 1D) was determined from publicly available cDNA microarray datasets from the Oncomine database. The number of samples for each tissue type is shown in brackets. CLL, chronic lymphocytic leukemia; MCL, mantle cell lymphoma; FL, follicular lymphoma; DLBCL, diffuse large B-cell lymphoma; SMZL, splenic marginal zone B-cell lymphoma; HL, Hodgkin lymphoma; BL, Burkitt's lymphoma; MM, multiple myeloma; HCL, hairy cell leukemia (FIG. 2A) The expression of TCL1 protein was determined by immunohistochemistry in formalin-fixed paraffin embedded primary human lymphoma tissues [FL, follicular lymphoma (n=5); CLL, chronic lymphocytic leukemia (n=2); MCL, mantle cell lymphoma (n=3); DLBCL, diffuse large B-cell lymphoma (n=2); SMZL, splenic marginal zone B-cell lymphoma (n=3)] and reactive human tonsils (n=4)]. Images shown are the original magnification× 100. (FIG. 2B) Intracellular staining for TCL1 was performed on primary human lymphoma cells and normal human peripheral blood B cells, and samples were analyzed by flow cytometry. The relative expression of TCL1 was calculated as follows: Mean fluorescence intensity (MFI) of TCL1 in test sample/MFI of TCL1 in normal B cells. Horizontal lines represent the median value for each group. P value on the top of graph represents comparison between normal donor B cells and all lymphomas. P values below the graph represent comparison between normal donor B cells and each lymphoma subtype. All P values were calculated by two-tailed Student's t test. (FIG. 2C) TCL1 protein expression was determined by Western blotting in two FL and two normal donor (ND) peripheral blood B cells. β-actin protein expression was used as loading control.

(FIG. 3A) PBMCs from HLA-A2+ normal donors were stimulated with overlapping 15-mer peptides spanning the entire length of the TCL1 protein (see Table 2). T cells from each condition were washed and incubated with autologous CD3-depleted PBMC as antigen-presenting cells (APC) in the presence or absence of the corresponding peptide. After 18 hours, the production of IFN-γ was determined in the supernatants by ELISA. Asterisk indicates significant IFN-γ production compared with control (P<0.05). Representative data from one of three normal donors tested is shown. (FIG. 3B) T cell lines generated from HLA-A2+ normal donors using $TCL1_{65-79}$ peptide were incubated with APC in the presence or absence of the $TCL1_{65-79}$ peptide or control HIV $Gag_{77-85}$ peptide, and intracellular cytokine assay was performed. The percentage of CD4+ and CD8+ T cells producing IFN-γ are shown. (FIG. 3C) $TCL1_{65-79}$ peptide-specific T cells were incubated with T2 cells or EBV-transformed B lymphoblastoid cell lines (IHW1003, IHW1019, IHW1089, and IHW1135) mismatched at their MHC class I locus in the presence of the $TCL1_{65-79}$ peptide or control HIV $Gag_{77-85}$ peptide. IFN-γ production was determined as in (FIG. 3A). The HLA-A alleles for each of the cell lines are shown. (FIG. 3D, FIG. 3E) A 4-hour $^{51}$Cr-release cytotoxicity assay was performed. $TCL1_{65-79}$ peptide-specific T cells were incubated with T2 cells alone or T2 cells pulsed with $TCL1_{65-79}$ peptide or control HIV $Gag_{77-85}$ peptide, at various effector:target ratios. For MHC blocking assay, an effector:target ratio of 20:1 was used in the presence or absence of isotype control antibody or blocking antibodies against MHC class I, MHC class II, HLA-A2, or HLA-B and C. All cytotoxicity assays were performed in triplicate wells and mean and standard deviation are shown.

(FIG. 4A) $TCL1_{65-79}$ peptide-specific T cells derived from HLA-A2+ normal donors were incubated in the presence or absence of T2 cells and $TCL1_{65-79}$ derived truncated peptides (SEQ ID NOS:1-2; SEQ ID NOS:12-17; SEQ ID NOS:3-11; and SEQ ID NO:18) Flu matrix peptide ($FMP_{58-66}$) and $Gag_{77-85}$ peptide were used as controls. After 18 hours, the production of IFN-γ was determined in the supernatants by ELISA. (FIG. 4B) T2 cells were incubated with $TCL1_{65-79}$-derived truncated peptides (SEQ ID NOS:1-2; SEQ ID NOS:12-17; SEQ ID NOS:3-11; and SEQ ID NO:18), and the HLA-A2 binding affinity of each peptide was determined by flow cytometry. The T2 binding index was calculated as described in Materials and Methods. (FIG. 4C) $TCL1_{65-79}$ (SEQ ID NO:1) peptide-specific T cells were incubated with T2 cells pulsed with $TCL1_{65-79}$-derived truncated peptides (SEQ ID NO:1; SEQ ID NO:8; SEQ ID NO:10; SEQ ID NO:11; SEQ ID NO:18) or control HIV $Gag_{77-85}$ peptide and a 4-hour $^{51}$Cr-release cytotoxicity assay was performed. The percent specific lysis is shown. (FIG. 4D) $TCL1_{65-79}$ peptide-specific CD8+ T cells or irrelevant T-cell line were stained with $TCL1_{71-78}$ or HIV $Gag_{77-85}$ tetramers and analyzed by flow cytometry. The percentage of tetramer positive T cells is shown. Data in panels A-D are representative of three independent experiments each.

(FIG. 5A, FIG. 5C) Intracellular staining for TCL1 was performed on tumor cell lines and normal donor peripheral blood B cells (FIG. 5A), and primary human lymphoma cells (FIG. 5C). Black histograms represent cells stained with isotype control antibody, and open histograms represent staining with TCL1 antibody. (FIG. 5B, FIG. 5D) CD8+ T cells purified from $TCL1_{65-79}$ peptide-specific T cell lines by MACS were incubated with tumor cell lines and normal donor-derived peripheral blood B cells (FIG. 5B) or primary human lymphoma cells (FIG. 5D). A 4-hour $^{51}$Cr-release cytotoxicity assay was performed, and the percent specific lysis is shown. The HLA-A2 expression for each of the cell types is shown in the figures. Data in panels (FIG. 5B) and (FIG. 5D) is representative of three independent experiments. CLL, chronic lymphocytic leukemia; MCL, mantle cell lymphoma; FL, follicular lymphoma; DLBCL, diffuse large B-cell lymphoma; SMZL, splenic marginal zone B-cell lymphoma.

(FIG. 6A) PBMC and tumor-infiltrating lymphocytes (TILs) derived from HLA-A2+ patients with chronic lymphocytic leukemia (CLL) or follicular lymphoma (FL) were stimulated in vitro with $TCL1_{65-79}$ After five stimulations, IFN-γ production in response to TCL1$_{65-79}$ peptide was determined as in FIG. 3A. (FIG. 6B, FIG. 6E) The cytotoxic function of TCL1$_{65-79}$ peptide-specific T cells generated above was tested against T2 cells pulsed with TCL1$_{65-79}$ peptide or HIV Gag$_{77-85}$ peptide (FIG. 6B) or primary autologous or allogeneic HLA-A2$^+$ or HLA-A2$^-$ mantle cell lymphoma (MCL Tu) or FL tumor cells (FL Tu) or tumor-free PBMC from MCL3 and FL5 patients (MCL3-PB and FL5-PB) or HLA-A2$^+$ MCF-7 cell line (FIG. 6E). (FIG. 6C) The percentage of tetramer positive CD8$^+$ T cells in each of the TCL1-specific T-cell lines generated from lymphoma patients is shown. (FIG. 6D) The expression of TCL1 in each of the primary lymphoma samples as determined by flow cytometry is shown. All cytotoxicity assays were performed in triplicate wells and mean and standard deviation are shown. CLL1-PB-T: TCL1-specific CTL generated from peripheral blood T cells of CLL patient 1; FL5-PB-T: TCL1-specific CTL generated from peripheral blood T cells of FL patient 5; FL5-TILs-T: TCL1-specific CTL generated from tumor infiltrating T cells of FL patient 5.

FIGS. 9A-D: Summary of cytokine secretion profile of TCL1 specific CTLs derived from normal donors or lymphoma patients. T2 cells were pulsed with TCL1$_{65-79}$ peptide in the presence of 3 ng/ml 32-microglobulin overnight and then incubated with normal donor-derived (FIG. 9A) or lymphoma patient-derived (FIG. 9B, FIG. 9C, FIG. 9D) TCL1-specific CTLs for one hour prior to adding Brefeldin A. The cytokine expression was determined 12 hours later by intracellular staining. TCL1-specific CTLs secreted IFN-γ, GM-CSF, and TNFα but not IL-4, IL-10, and IL-17.

(FIG. 13A) TCL1 expression in hematopoietic stem cells (HSC–CD19$^-$CD20$^-$CD10$^-$CD34$^+$), pro-B cells (CD19$^+$CD20$^-$CD10$^+$CD34$^+$), pre-B cells (CD19$^+$CD20$^-$CD10$^+$CD34$^-$), and immature B cells (CD19$^+$CD20$^+$CD10$^-$CD34$^-$) in normal human bone marrow samples, and primary mantle cell lymphoma tumor cells was determined by flow cytometry and compared to autologous non-B cells or isotype antibody staining as control. Mean fluorescence intensity of each gated subset is indicated on right. Representative data from one of three bone marrow samples tested is shown. (FIG. 13B) TCL1 expression in naïve B cells (CD19$^+$IgD$^+$CD10$^-$CD27$^-$CD38$^-$), germinal center (GC) B cells (CD19$^+$IgD$^-$CD10$^+$CD27$^-$CD38$^{int}$), memory B cells (CD19$^+$IgD$^-$CD10$^-$CD27$^+$CD38$^-$), and plasma cells (CD19$^+$IgD$^-$CD10$^-$CD27$^+$CD38$^{hi}$) in normal tonsils was determined by flow cytometry and compared to autologous non-B cells as control. Mean fluorescence intensity of each gated subset is indicated on right. Representative data from one of three tonsil samples tested is shown. (FIG. 13C) TCL1 expression was determined by flow cytometry in 18-week-old human fetal thymocytes. Top panel. Gating strategy for Double Negative (DN), Double Positive (DP), and Single Positive (SP) CD4 and CD8 thymocytes is shown. Bottom panel. TCL1 expression (open histogram) in thymocyte subsets as compared with isotype control antibody (grey histogram) is shown. Representative data from one of two fetal thymus tissues tested is shown.

(FIG. 16A) Phenotypic analysis of CD8$^+$ T cells purified from TCL1$_{65-79}$ peptide-specific T cell lines was performed with CD16 PE, CD56 PE, CD3 PerCP-Cy5.5, and CD8 FITC antibodies. Top panel. The percentage of T cells (CD3+), NK cells (CD3–CD16+CD56+), and CD8 T cells is shown. Representative data from one of three lines is shown. Bottom panel. Normal donor (ND) PBMC were used as control. (FIG. 16B) CD8$^+$ T cells purified from a TCL1$_{65-79}$ peptide-specific T cell line were incubated with HLA-A2$^+$ normal human bone marrow-derived CD34$^+$ hematopoietic stem cells; normal tonsil-derived naïve B cells, germinal center (GC) B cells, or memory B cells; Jeko-1 cells; and primary follicular lymphoma tumor cells (FL5). A 4-hour $^{51}$Cr-release cytotoxicity assay was performed. The percent specific lysis is shown. Representative data from one of three lines is shown.

DESCRIPTION OF ILLUSTRATIVE EMBODIMENTS

Figure 1A:
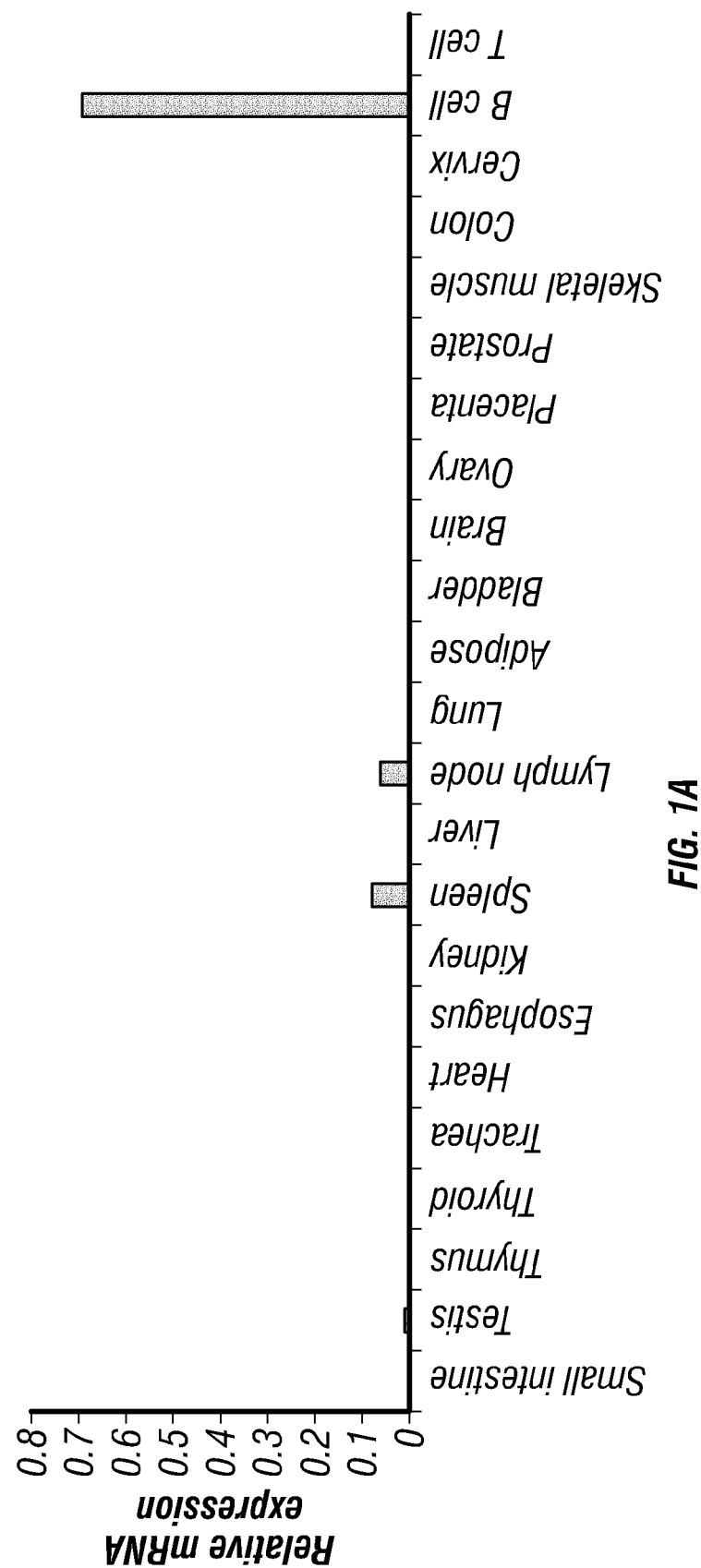
FIGS. 1A-D: TCL1 mRNA is hyperexpressed in multiple B cell lymphomas.

The present invention is based, in part, on the identification of TCL1 peptides that are recognized by the immune system and may be used in various immunotherapies to treat a cancer. As shown in the below examples, antigenic peptides of the T-cell leukemia/lymphoma 1 (TCL1) oncoprotein can be used for immunotherapy of B-cell malignancies. TCL1 mRNA and protein were observed to be selectively expressed at low levels in B cells among normal adult tissues but markedly hyperexpressed in multiple human B-cell lymphomas including follicular lymphoma, chronic lymphocytic leukemia, mantle cell lymphoma, diffuse large B-cell lymphoma, and splenic marginal zone B-cell lymphoma. TCL1-specific CD8$^+$ T cells can be generated from HLA-A*0201 (HLA-A2)$^+$ normal donors, and TCL1$_{71-78}$ (LLPIMWQL) (SEQ ID NO:11) was identified as the minimal immunogenic HLA-A2 binding epitope. It was also shown that TCL1$_{71-78}$ peptide-specific T cells are present in the peripheral blood and tumor-infiltrating lymphocytes of lymphoma patients, can be expanded in vitro, and lyse autologous tumor cells but not normal B cells in an HLA-A2-restricted manner. TCL1 peptides of the present invention and related antibodies may be used in a variety of immunotherapeutic strategies for the treatment of a cancer, such as a B cell malignancy.

I. TCL1 IS A TARGET FOR B-CELL LYMPHOMAS

The T-cell leukemia/lymphoma 1 (TCL1) oncoprotein encoded by the TCL1 gene (also called TCL1A) is aberrantly expressed in several B-cell malignancies (Aggarwal et al., 2008; Teitell, 2005; Said et al., 2001; Narducci et al., 2000). TCL1 is primarily expressed during early embryogenesis in fetal lymphoid tissues, including liver, yolk sac, thymus, spleen, tonsil, and bone marrow (Narducci et al., 1997a; Narducci et al., 2002). In adults, TCL1 expression is restricted to germ cells in the testis and precursor B and T lymphocytes. During B-cell development, TCL1 expression begins at the pre-B cell stage and is present until they differentiate into naïve B cells. Following antigen activation, TCL1 is down regulated in the germinal center (GC) B cells and is silenced in post-GC memory B cells and plasma cells (Said et al., 2001). During T-cell development, TCL1 is expressed in CD3$^-$CD4$^-$CD8$^-$ thymocytes but is absent in mature T cells in the periphery (Narducci et al., 1997b; Hoyer et al., 2005). TCL1 was demonstrated to function as a co-activator of Akt (also called protein kinase B) and thereby promote cell proliferation and survival (Laine et al., 2000). The tumorigenic role for TCL1 was established in transgenic mice where ectopic expression of human TCL1 in B cells resulted in the development of B-cell malignancies (Virgilio et al., 1998; Gritti et al., 1998; Hoyer et al., 2002). Furthermore, TCL1 expression was associated with adverse clinical outcome in CLL, MCL, and DLBCL (Aggarwal et al., 2008; Ramuz et al., 2005; Pekarsky et al., 2008; Herling et al., 2009).

TCL1 has been observed herein to be a shared tumor-associated antigen for B-cell malignancies and lymphomas. TCL1 is normally selectively expressed at low levels in normal B cells in adults, and is markedly hyperexpressed in most B-cell malignancies (Aggarwal et al., 2008; Said et al., 2001; Narducci et al., 2000; Herling et al., 2007). More importantly, the results suggest that tumor cells naturally process and present TCL1 on their cell surface in the context of HLA-A2 molecules for recognition and killing by TCL1-specific CTL. TCL1-specific CTL are not centrally deleted during thymic development as they can be generated from normal donors. Furthermore, TCL1$_{71-78}$ peptide-specific CTL can be detected and expanded in vitro from the PBMC and tumor-infiltrating lymphocytes of lymphoma patients. Without wishing to be bound by any theory, these results support the idea that TCL1 may be naturally immunogenic. However, the extent of the naturally induced TCL1-specific T cells may be insufficient to inhibit the growth of the tumor but may be augmented with immunotherapeutic strategies such as vaccines and adoptive T cell therapy for enhanced antitumor effect and/or clinical benefit.

While MHC class I molecules have been traditionally described to bind to peptides of 8-11 amino acids long, recent reports suggest that peptides as long as 15 amino acids can bind to MHC class I molecules by bulging in the middle of the binding site or extending out of the MHC class I binding groove (Guo et al., 1992; Burrows et al., 2006; Samino et al., 2006; Stryhn et al., 2000; Collins et al., 1994; Blanchard and Shastri, 2008). Moreover, recent studies also demonstrated that long peptides may be more efficiently endocytosed, processed, and presented by antigen-presenting cells (Zwaveling et al., 2002; Bijker et al., 2007; Melief and van der Burg, 2008; Quintarelli et al., 2011). By T2 binding assay, the inventors observed that the TCL1$_{65-79}$ 15 amino-acid long peptide bound to TAP-deficient T2 cells and was recognized by CTL when pulsed on to the T2 cells, indicating direct binding of TCL1$_{65-79}$ to HLA-A2 (FIGS. 3C-E and 4A-C). However, presentation by TCL1$_{65-79}$ peptide-pulsed antigen-presenting cells (FIGS. 3A and B) may involve either direct binding or presentation of truncated peptides by cross-presentation or cross-dressing pathways (Lin et al., 2008; Wakim and Bevan, 201). Using a panel of truncated peptides, the inventors identified TCL1$_{71-78}$ as the minimal epitope that bound to HLA-A2 and recognized by TCL1-specific CTL. As several truncated peptides bound to HLA-A2 and were recognized by TCL1-specific CTL (FIGS. 4A-C), identification of the natural TCL1-derived HLA-A2 ligand may be performed via isolation of MHC class I binding peptides from TCL1-expressing cells and analysis by mass spectrometry.

As shown in the below examples, TCL1 expression may be variable in tumor cells within each tumor (FIGS. 1C, 2A, and 6D) (Aggarwal et al., 2008; Said et al., 2001; Narducci et al., 2000; Herling et al., 2007). However, expression of low levels of TCL1 by the tumor cells may be sufficient since recognition by antigen-specific T cells requires only few MHC-peptide complexes on the cell surface (Irvine et al., 2002). Furthermore, even if TCL1 is not present in all tumor cells within each tumor, lysis of TCL1-expressing tumor cells by TCL1-specific CTL may be used to induce epitope spreading and broaden the immune response against tumor cells with or without TCL1 expression. Recent reports demonstrate that epitope spreading can develop in a high proportion of cancer patients who attain tumor regression after peptide-based cancer immunotherapy (Ribas et al., 2003). Thus, the variable level of TCL1 expression in lymphoma cells, if present, may not be a limitation for using TCL1 as a shared lymphoma-associated antigen for therapeutic vaccine development.

Figure 5A:
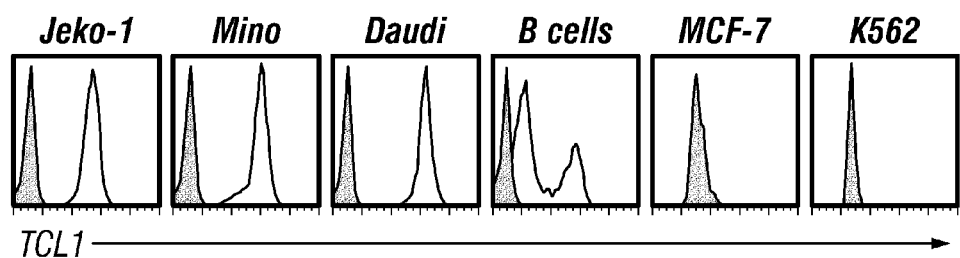
FIGS. 5A-D: $TCL1_{65-79}$ peptide-specific T cells lysed human lymphoma cell lines and primary lymphoma cells.
Figure 5B:
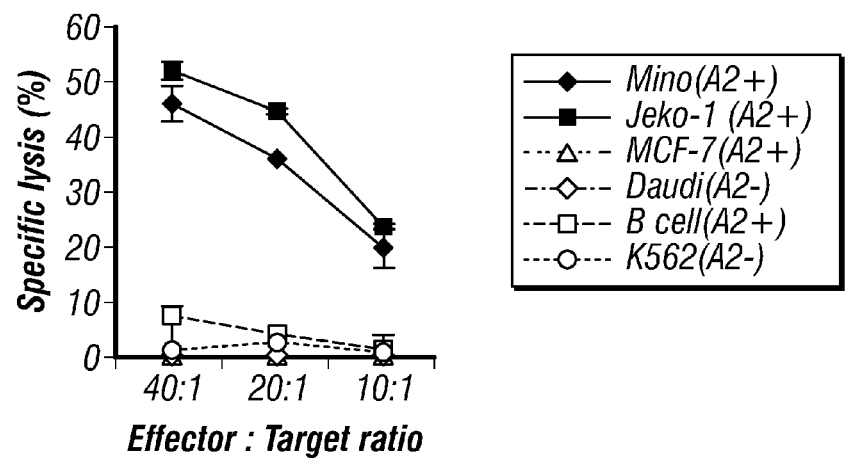
Figure 6A:
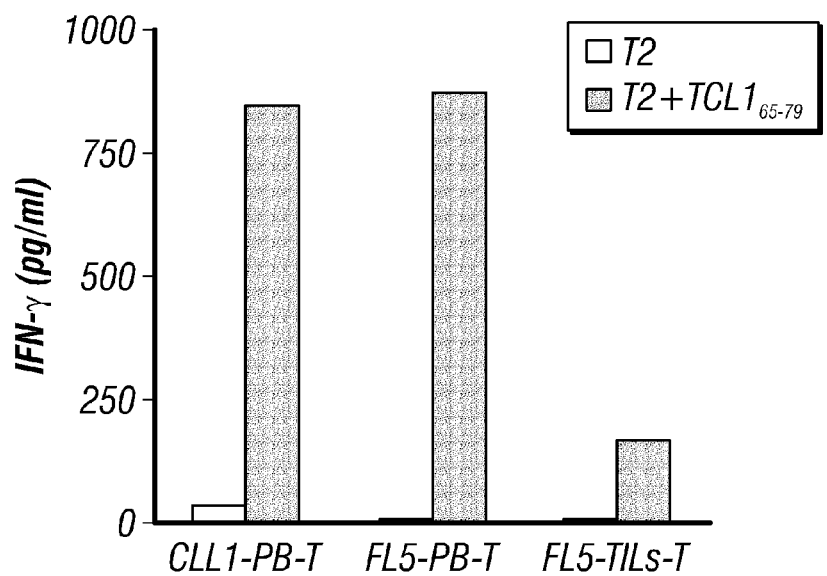
FIGS. 6A-E: $TCL1_{71-78}$ peptide-specific T cells can be generated from lymphoma patients.
Figure 6B:
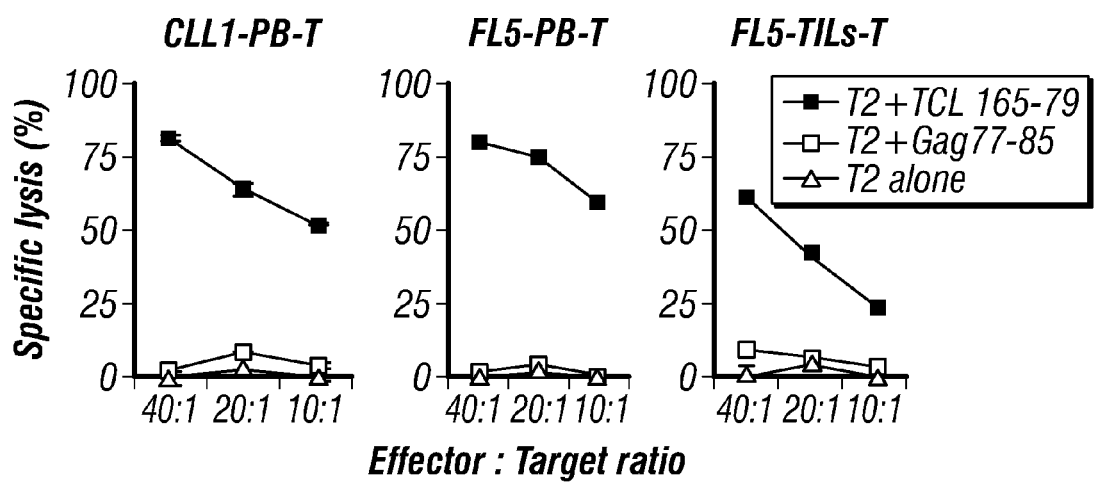
Figure 6C:
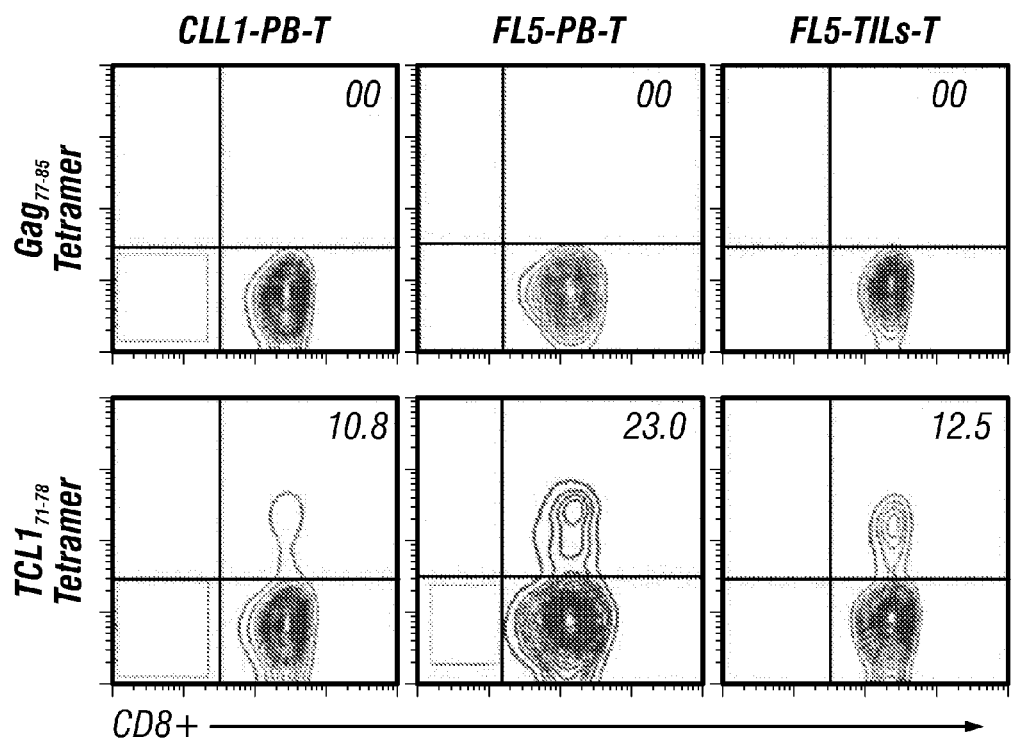
Figure 6D:
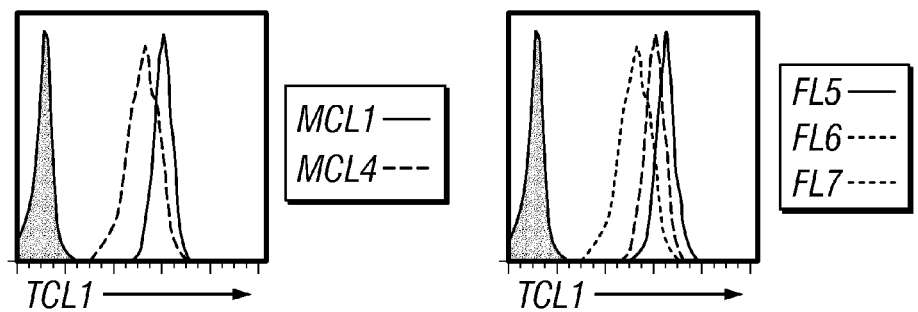
Figure 6E:
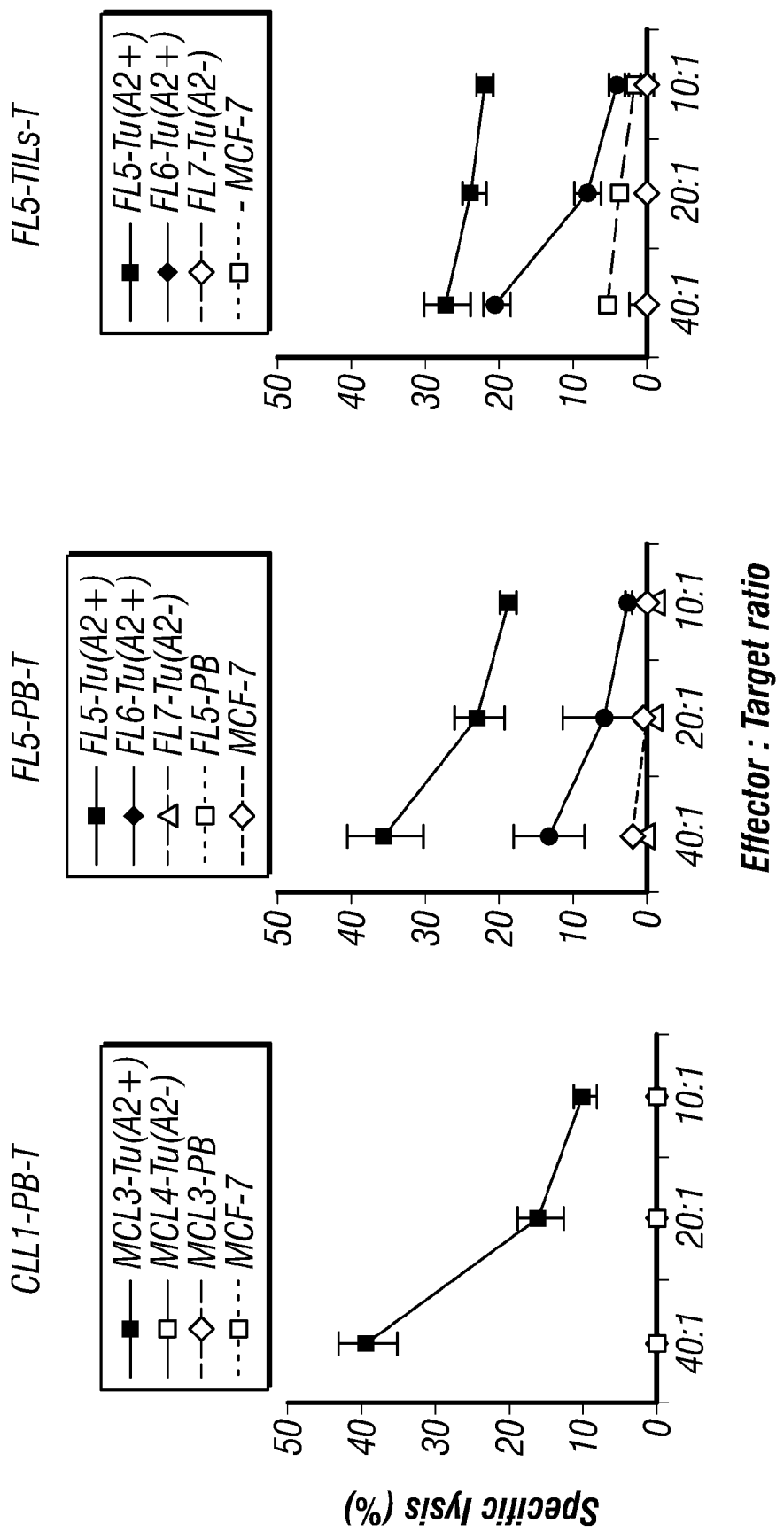

The pattern of TCL1 expression seen in the below studies is consistent with expression of TCL1 primarily in lymphoid tissues in precursor B and T cells and naïve B cells in adults (Said et al., 2001; Narducci et al., 2000). Using real-time PCR, flow cytometry, and Western blotting, the inventors observed that TCL1 is hyperexpressed in tumor B cells as compared with normal peripheral blood B cells. Consistent with this differential expression, the inventors did not observe significant lysis of normal B cells or autologous tumor-free PBMC by TCL1-specific CTL (FIGS. 5B and 6E). Various approaches may be taken to reduce the possibility that vaccination with TCL1 protein or TCL1-derived peptides may cause depletion of precursor B or naïve B cells. Although permanent depletion of B cells may result in hypogammaglobulinemia and increase the risk of infections, the morbidity can be minimized by prophylactic administration of intravenous gamma globulin as demonstrated in patients with X-linked agammaglobulinemia, a genetic disease characterized by lack of circulating B cells due to the mutation of Bruton's tyrosine kinase (Skull and Kemp, 1996). Depletion of normal B cells for several months after rituximab administration in patients with B cell lymphoma has also not resulted in increased incidence of infections (McLaughlin et al., 1998). Finally, TCL1 deficient mice had only modest deficiencies in B and T lymphopoiesis and slightly reduced IgG1 and IgG2b antibody production in response to a T-dependent antigen (Kang et al., 2005). In view of the foregoing, it is anticipated that targeting tumor B cells using a TCL1-derived vaccine may be administered to treat a cancer and may be substantially safe and well tolerated.

Although idiotype vaccines have been found to be safe, immunogenic, and induce clinical benefit in lymphoma patients, rapid progress in the development of idiotype vaccines has been hindered by the requirement for a tumor biopsy and the need to generate a custom-made product for each patient—a process that is expensive, laborious, and time-consuming Identification of TCL1 as a shared lymphoma-associated antigen may be used to generate vaccine formulations that may be used in many or most lymphoma patients and may, therefore, be easier and less costly to produce. Such shared lymphoma antigens may also be used to optimize vaccination strategies by evaluating novel vaccine formulations, doses, and schedules, as well as novel adjuvants in clinical trials. Furthermore, identification of TCL1 as a shared lymphoma-associated antigen would enable generation of autologous and allogeneic TCL1-specific T-cells for adoptive transfer strategies.

TCL1 may serve as a shared tumor-associated antigen for therapeutic vaccine development in common B-cell malignancies, including FL, CLL, MCL, DLCL, and SMZL. In the below examples, $TCL1_{71-78}$ was identified as the minimal peptide that bound to HLA-A2, an MHC class I allele present in approximately half of the general human population. In some embodiments, whole protein or genetic vaccines encoding a TCL1 gene may be used, e.g., without any restriction to HLA type.

II. IMMUNOTHERAPIES USING TCL1 PEPTIDES

A TCL1 peptide may be used for immunotherapy of a cancer. For example, a TCL1 peptide may be contacted with or used to stimulate a population of T cells to induce proliferation of the T cells that recognize or bind the TCL1 peptide.

In other embodiments, a TCL1 peptide of the present invention may be administered to a subject, such as a human patient, to enhance the immune response of the subject against a cancer. For tumors such as melanoma, the adoptive transfer of tumor-infiltrating lymphocytes (TILs) has been shown to result in significant patient benefit (Hawkins et al., 2010).

A TCL1 peptide may be included in an active immunotherapy (e.g., a cancer vaccine) or a passive immunotherapy (e.g., an adoptive immunotherapy). Active immunotherapies include immunizing a subject with a purified TCL1 peptide antigen or an immunodominant TCL1 peptide (native or modified); alternately, antigen presenting cells pulsed with a TCL1 peptide (or transfected with genes encoding the TCL1 antigen) may be administered to a subject. Passive immunotherapies include adoptive immunotherapies. Adoptive immunotherapies generally involve administering cells to a subject, wherein the cells (e.g., cytotoxic T cells) have been sensitized in vitro to TCL1 (see, e.g., U.S. Pat. No. 7,910, 109).

In some embodiments, flow cytometry may be used in the adoptive immunotherapy for rapid isolation of human tumor antigen-specific T-cell clones by using, e.g., T-cell receptor (TCR) Vβ antibodies in combination with carboxyfluorescein succinimidyl ester (CFSE)-based proliferation assay. See, e.g., Lee et al. (2008), which is incorporated by reference without disclaimer. Various culture protocols are also known for adoptive immunotherapy and may be used with the present invention; in some embodiments, cells may be cultured in conditions which do not require the use of antigen presenting cells (e.g., Hida et al., 2002). In other embodiments, T cells may be expanded under culture conditions that utilize antigen presenting cells, such as dendritic cells (Nestle et al., 1998), and in some embodiments artificial antigen presenting cells may be used for this purpose (Maus et al., 2002). Additional methods for adoptive immunotherapy are disclosed in Dudley et al. (2003) that may be used with the present invention. Various methods are known and may be used for cloning and expanding human antigen-specific T cells (see, e.g., Riddell et al., 1990).

In certain embodiments, the following protocol may be used to generate T cells that selectively recognize TCL1 peptides. Peptide-specific T-cell lines may be generated from HLA-A2$^+$ normal donors and patients using methods previously reported (Hida et al., 2002). Briefly, PBMCs ($1\times10^5$ cells/well) were stimulated with about 10 mg/ml of each peptide in quadruplicate in a 96-well, U-bottom-microculture plate (Corning Incorporated, Lowell, Mass.) in about 200 µl of culture medium. The culture medium may consist of 50% AIM-V medium (Invitrogen), 50% RPMI1640 medium (Invitrogen), 10% human AB serum (Valley Biomedical, Winchester, Va.), and 100 IU/ml of interleukin-2 (IL-2). Cells may be restimulated with the corresponding peptide about every 3 days. After 5 stimulations, T cells from each well may be washed and incubated with T2 cells in the presence or absence of the corresponding peptide. After about 18 hours, the production of interferon (IFN)-γ may be determined in the supernatants by ELISA. T cells that secret large amounts of IFN-γ may be further expanded by a rapid expansion protocol (Lee et al., 2008).

In some embodiments, an immunotherapy may utilize a TCL1 peptide of the present invention that is associated with a cell penetrator, such as a liposome or a cell penetrating peptide (CPP). Antigen presenting cells (such as dendritic cells) pulsed with peptides may be used to enhance antitumour immunity (Celluzzi et al., 1996; Young et al., 1996). Liposomes and CPPs are described in further detail below.

III. TCL1 PEPTIDES

As used herein, the term "peptide" encompasses amino acid chains comprising less than about 45 amino acids, preferably 7-20 amino acid residues, and even more preferably 8-15 amino acids, wherein the amino acid residues are linked by covalent peptide bonds. For example, a TCL1 peptide of the present invention may, in some embodiments, comprise or consist of a TCL1 peptide in FIG. 4A-B (SEQ ID NOs:1-11). As used herein, an "antigenic peptide" is a peptide which, when introduced into a vertebrate, can stimulate the production of antibodies in the vertebrate, i.e., is antigenic, and wherein the antibody can selectively recognize and/or bind the antigenic peptide. An antigenic peptide may comprise an immunoreactive TCL1 peptide, and may comprise additional sequences. The additional sequences may be derived from a native antigen and may be heterologous, and such sequences may, but need not, be immunogenic. In some embodiments, a TCL1 peptide can selectively bind with a HLA-A2. In certain embodiments, the TCL1 peptide is 8, 9, 10, 11, 12, 13, 14, or 15 amino acids in length, or any range derivable therein. Select TCL1 peptides are listed in Table 1 below.

TABLE 1

Immunogenic TCL1 Peptides

| Amino acid location in TCL1 protein | Peptide Sequence | SEQ ID NO: |
|---|---|---|
| 65-79 | TQIGPSLLPIMWQLY | 1 |
| 65-78 | TQIGPSLLPIMWQL | 2 |
| 66-79 | QIGPSLLPIMWQLY | 3 |
| 67-79 | IGPSLLPIMWQLY | 4 |
| 68-79 | GPSLLPIMWQLY | 5 |
| 69-79 | PSLLPIMWQLY | 6 |
| 70-79 | SLLPIMWQLY | 7 |
| 71-79 | LLPIMWQLY | 8 |
| 72-79 | LPIMWQLY | 9 |
| 70-78 | SLLPIMWQL | 10 |
| 71-78 | LLPIMWQL | 11 |

In certain embodiments, a TCL1 peptide may be immunogenic or antigenic. As shown in the below examples, various TCL1 peptides of the present invention can promote the proliferation of T cells. It is anticipated that such peptides could be used to induce some degree of protective immunity.

A TCL1 peptide may be a recombinant peptide, synthetic peptide, purified peptide, immobilized peptide, detectably labeled peptide, encapsulated peptide, or a vector-expressed peptide. In some embodiments, a synthetic TCL1 peptide may be administered to a subject, such as a human patient, to induce an immune response in the subject. Synthetic peptides may display certain advantages, such as a decreased risk of bacterial contamination, as compared to recombinantly expressed peptides. A TCL1 peptide may also be comprised in a pharmaceutical composition such as, e.g., a vaccine composition, which is formulated for administration to a mammalian or human subject.

As described in further detail in the examples below, overlapping peptides derived from TCL1 were generated and are listed in Table 2 below. A TCL1 peptide from the list below may be used in some embodiments of the present invention.

TABLE 2

Overlapping peptides derived from TCL1

| Peptide Name | Position | Sequence | SEQ ID NO: |
|---|---|---|---|
| P1 | 1-15 | MAECPTLGEAVTDHP | 19 |
| P2 | 5-19 | PTLGEAVTDHPDRLW | 20 |
| P3 | 9-23 | EAVTDHPDRLWAWEK | 21 |
| P4 | 13-27 | DHPDRLWAWEKFVYL | 22 |
| P5 | 17-31 | RLWAWEKFVYLDEKQ | 23 |
| P6 | 21-35 | WEKFVYLDEKQHAWL | 24 |
| P7 | 25-39 | VYLDEKQHAWLPLTI | 25 |
| P8 | 29-43 | EKQHAWLPLTIEIKD | 26 |
| P9 | 33-47 | AWLPLTIEIKDRLQL | 27 |
| P10 | 37-51 | LTIEIKDRLQLRVLL | 28 |
| P11 | 41-55 | IKDRLQLRVLLRRED | 29 |
| P12 | 45-59 | LQLRVLLRREDVVLG | 30 |
| P13 | 49-63 | VLLRREDVVLGRPMT | 31 |
| P14 | 53-67 | REDVVLGRPMTPTQI | 32 |
| P15 | 57-71 | VLGRPMTPTQIGPSL | 33 |
| P16 | 61-75 | PMTPTQIGPSLLPIM | 34 |
| P17 | 65-79 | TQIGPSLLPIMWQLY | 1 |
| P18 | 69-83 | PSLLPIMWQLYPDGR | 35 |
| P19 | 73-87 | PIMWQLYPDGRYRSS | 36 |
| P20 | 77-91 | QLYPDGRYRSSDSSF | 37 |
| P21 | 81-95 | DGRYRSSDSSFWRLV | 38 |
| P22 | 85-99 | RSSDSSFWRLVYHIK | 39 |
| P23 | 89-103 | SSFWRLVYHIKIDGV | 40 |
| P24 | 93-107 | RLVYHIKIDGVEDML | 41 |
| P25 | 97-111 | HIKIDGVEDMLLELL | 42 |
| P26 | 101-114 | DGVEDMLLELLPDD | 43 |

A. Cell Penetrating Peptides

A TCL1 peptide may also be associated with or bound to a cell penetrating peptide (CPP). Cell penetrating peptides that may be covalently bound to a TCL1 peptide include, e.g., HIV Tat, herpes virus VP22, the *Drosophila* Antennapedia homeobox gene product, signal sequences, fusion sequences, or protegrin I. Covalently binding a peptide to a CPP can prolong the presentation of a peptide by dendritic cells, thus enhancing antitumour immunity (Wang and Wang, 2002). In some embodiments, a TCL1 peptide of the present invention (e.g., comprised within a peptide or polyepitope string) may be covalently bound (e.g., via a peptide bond) to a CPP to generate a fusion protein. In other embodiments, a TCL1 peptide or nucleic acid encoding a TCL1 peptide may be encapsulated within or associated with a liposome, such as a mulitlamellar, vesicular, or multivesicular liposome.

As used herein, "association" means a physical association, a chemical association or both. For example, an association can involve a covalent bond, a hydrophobic interaction, encapsulation, surface adsorption, or the like.

As used herein, "cell penetrator" refers to a composition or compound which enhances the intracellular delivery of the peptide/polyepitope string to the antigen presenting cell. For example, the cell penetrator may be a lipid which, when associated with the peptide, enhances its capacity to cross the plasma membrane. Alternatively, the cell penetrator may be a peptide. Cell penetrating peptides (CPPs) are known in the art, and include, e.g., the Tat protein of HIV (Frankel and Pabo, 1988), the VP22 protein of HSV (Elliott and O'Hare, 1997) and fibroblast growth factor (Lin et al., 1995).

Cell-penetrating peptides (or "protein transduction domains") have been identified from the third helix of the Drosophila Antennapedia homeobox gene (Antp), the HIV Tat, and the herpes virus VP22, all of which contain positively charged domains enriched for arginine and lysine residues (Schwarze et al., 2000; Schwarze et al., 1999). Also, hydrophobic peptides derived from signal sequences have been identified as cell-penetrating peptides. (Rojas et al., 1996; Rojas et al., 1998; Du et al., 1998). Coupling these peptides to marker proteins such as β-galactosidase has been shown to confer efficient internalization of the marker protein into cells, and chimeric, in-frame fusion proteins containing these peptides have been used to deliver proteins to a wide spectrum of cell types both in vitro and in vivo (Drin et al., 2002). Fusion of these cell penetrating peptides to a TCL1 peptide in accordance with the present invention may enhance cellular uptake of the polypeptides.

In other embodiments, cellular uptake is facilitated by the attachment of a lipid, such as stearate or myristilate, to the polypeptide. Lipidation has been shown to enhance the passage of peptides into cells. The attachment of a lipid moiety is another way that the present invention increases polypeptide uptake by the cell. Cellular uptake is further discussed below.

In certain embodiments, a TCL1 peptide of the present invention may be included in a liposomal vaccine composition. For example, the liposomal composition may be or comprise a proteoliposomal composition. Methods for producing proteoliposomal compositions that may be used with the present invention are described, e.g., in Neelapu et al. (2007) and Popescu et al. (2007). In some embodiments, proteoliposomal compositions may be used to treat a leukemia or lymphoma such as, e.g., a follicular lymphoma.

By enhancing the uptake of a TCL1 polypeptide, the present invention can reduce the amount of protein or peptide required for treatment. This in turn can significantly reduce the cost of treatment and increase the supply of therapeutic agent. Lower dosages can also minimize the potential immunogenicity of peptides and limit toxic side effects. As such, the compositions and methods of the present invention provide significant benefits for therapeutic treatments.

In accordance with the present invention, a TCL1 peptide may be associated with a nanoparticle to form nanoparticle-polypeptide complex. In some embodiments, the nanoparticle is a liposomes or other lipid-based nanoparticle such as a lipid-based vesicle (e.g., a DOTAP:cholesterol vesicle). In other embodiments, the nanoparticle is an iron-oxide based superparamagnetic nanoparticles. Superparamagnetic nanoparticles ranging in diameter from about 10 to 100 nm are small enough to avoid sequestering by the spleen, but large enough to avoid clearance by the liver. Particles this size can penetrate very small capillaries and can be effectively distributed in body tissues. Superparamagnetic nanoparticles-polypeptide complexes can be used as MRI contrast agents to identify and follow those cells that take up the TCL1 peptide. In certain embodiments, the nanoparticle is a semiconductor nanocrystal or a semiconductor quantum dot, both of which can be used in optical imaging. In further embodiments, the nanoparticle can be a nanoshell, which comprises a gold layer over a core of silica. One advantage of nanoshells is that polypeptides can be conjugated to the gold layer using standard chemistry. In other embodiments, the nanoparticle can be a fullerene or a nanotube (Gupta et al., 2005).

Peptides are rapidly removed from the circulation by the kidney and are sensitive to degradation by proteases in serum. By associating a TCL1 peptide with a nanoparticle, the nanoparticle-polypeptide complexes of the present invention may protect against degradation and/or reduce clearance by the kidney. This may increase the serum half-life of polypeptides, thereby reducing the polypeptide dose need for effective therapy. Further, this may decrease the costs of treatment, and minimizes immunological problems and toxic reactions of therapy.

B. Polyepitope Strings

In some embodiments, a TCL1 peptide is included or comprised in a polyepitope string. A polyepitope string is a peptide or polypeptide containing a plurality of antigenic epitopes from one or more antigens linked together. A polyepitope string may be used to induce an immune response in a subject, such as a human subject. Polyepitope strings have been previously used to target malaria and other pathogens (Baraldo et al., 2005; Moorthy et al., 2004; Baird et al., 2004). A polyepitope string may refer to a nucleic acid (e.g., a nucleic acid encoding a plurality of antigens including a TCL1 peptide) or a peptide or polypeptide (e.g., containing a plurality of antigens including a TCL1 peptide). A polyepitope string may be included in a cancer vaccine composition.

C. Biological Functional Equivalents

A TCL1 peptide of the present invention may be modified to contain amino acid substitutions, insertions and/or deletions that do not alter their respective interactions with HLA-A2 binding regions. Such a biologically functional equivalent of a TCL1 peptide could be a molecule having like or otherwise desirable characteristics, e.g., binding of HLA-A2. As a nonlimiting example, certain amino acids may be substituted for other amino acids in an TCL1 peptide disclosed herein without appreciable loss of interactive capacity, as demonstrated by detectably unchanged antibody binding. It is thus contemplated that an TCL1 peptide disclosed herein (or a nucleic acid encoding such a peptide) which is modified in sequence and/or structure, but which is unchanged in biological utility or activity remains within the scope of the present invention.

It is also well understood by the skilled artisan that, inherent in the definition of a biologically functional equivalent peptide, is the concept that there is a limit to the number of changes that may be made within a defined portion of the molecule while still maintaining an acceptable level of equivalent biological activity. Biologically functional equivalent peptides are thus defined herein as those peptides in which certain, not most or all, of the amino acids may be substituted. Of course, a plurality of distinct peptides with different substitutions may easily be made and used in accordance with the invention.

The skilled artisan is also aware that where certain residues are shown to be particularly important to the biological or structural properties of a peptide, e.g., residues in specific epitopes, such residues may not generally be exchanged. This may be the case in the present invention, as a mutation in an TCL1 peptide disclosed herein could result in a loss of species-specificity and in turn, reduce the utility of the resulting peptide for use in methods of the present invention. Thus, peptides which are antigenic (i.e., bind HLA-A2 specifically) and comprise conservative amino acid substitutions are understood to be included in the present invention. Conservative substitutions are least likely to drastically alter the activity of a protein. A "conservative amino acid substitution" refers to replacement of amino acid with a chemically similar amino acid, i.e., replacing nonpolar amino acids with other nonpolar amino acids; substitution of polar amino acids with other polar amino acids, acidic residues with other acidic amino acids, etc.

Amino acid substitutions, such as those which might be employed in modifying an TCL1 peptide disclosed herein are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

The invention also contemplates isoforms of the TCL1 peptides disclosed herein. An isoform contains the same number and kinds of amino acids as a peptide of the invention, but the isoform has a different molecular structure. The isoforms contemplated by the present invention are those having the same properties as a peptide of the invention as described herein.

Nonstandard amino acids may be incorporated into proteins by chemical modification of existing amino acids or by de novo synthesis of a peptide disclosed herein. A nonstandard amino acid refers to an amino acid that differs in chemical structure from the twenty standard amino acids encoded by the genetic code.

In select embodiments, the present invention contemplates a chemical derivative of an TCL1 peptide disclosed herein. "Chemical derivative" refers to a peptide having one or more residues chemically derivatized by reaction of a functional side group, and retaining biological activity and utility. Such derivatized peptides include, for example, those in which free amino groups have been derivatized to form specific salts or derivatized by alkylation and/or acylation, p-toluene sulfonyl groups, carbobenzoxy groups, t-butylocycarbonyl groups, chloroacetyl groups, formyl or acetyl groups among others. Free carboxyl groups may be derivatized to form organic or inorganic salts, methyl and ethyl esters or other types of esters or hydrazides and preferably amides (primary or secondary). Chemical derivatives may include those peptides which comprise one or more naturally occurring amino acids derivatives of the twenty standard amino acids. For example, 4-hydroxyproline may be substituted for serine; and ornithine may be substituted for lysine.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The amino acids described herein are preferred to be in the "L" isomeric form. However, residues in the "D" isomeric form can be substituted for any L-amino acid residue, as long as the desired functional properties set forth herein are retained by the protein.

Preferred TCL1 peptides or analogs thereof preferably specifically or preferentially bind a HLA-A2. Determining whether or to what degree a particular TCL1 peptide or labeled peptide, or an analog thereof, can bind an HLA-A2 can be assessed using an in vitro assay such as, for example, an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (FA), nephelometry, flow cytometry assay, chemiluminescence assay, lateral flow immunoassay, u-capture assay, mass spectrometry assay, particle-based assay, inhibition assay and/or an avidity assay.

D. Nucleic Acids Encoding a TCL1 Peptide

In an aspect, the present invention provides a nucleic acid encoding an isolated TCL1 peptide comprising a sequence that has at least about 90%, 91%, 92%, 93%, 94%, 95%, 96%, 97%, 98%, 99%, or 100% sequence identity to any of SEQ ID NOs. 1-11. Such a TCL1 peptide may be from 7 to 45, 7-20, or 8-15 amino acids in length, or any range derivable therein. In some embodiments, the TCL1 peptide corresponds to a portion of the TCL1 protein (NC_000014.8; Gene ID: 8115). The term "nucleic acid" is intended to include DNA and RNA and can be either double stranded or single stranded.

Some embodiments of the present invention provide recombinantly produced TCL1 peptides which can specifically bind a HLA-A2. Accordingly, a nucleic acid encoding a TCL1 peptide may be operably linked to an expression vector and the peptide produced in the appropriate expression system using methods well known in the molecular biological arts. A nucleic acid encoding a TCL1 peptide disclosed herein may be incorporated into any expression vector which ensures good expression of the peptide. Possible expression vectors include but are not limited to cosmids, plasmids, or modified viruses (e.g. replication defective retroviruses, adenoviruses and adeno-associated viruses), so long as the vector is suitable for transformation of a host cell.

A recombinant expression vector being "suitable for transformation of a host cell", means that the expression vector contains a nucleic acid molecule of the invention and regulatory sequences selected on the basis of the host cells to be used for expression, which is operatively linked to the nucleic acid molecule. The terms, "operatively linked" or "operably linked" are used interchangeably, and are intended to mean that the nucleic acid is linked to regulatory sequences in a manner which allows expression of the nucleic acid.

Accordingly, the present invention provides a recombinant expression vector comprising nucleic acid encoding an TCL1 peptide, and the necessary regulatory sequences for the transcription and translation of the inserted protein-sequence. Suitable regulatory sequences may be derived from a variety of sources, including bacterial, fungal, or viral genes (e.g., see the regulatory sequences described in Goeddel (1990).

Selection of appropriate regulatory sequences is dependent on the host cell chosen, and may be readily accomplished by one of ordinary skill in the art Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

A recombinant expression vector may also contain a selectable marker gene which facilitates the selection of host cells transformed or transfected with a recombinant TCL1 peptide disclosed herein. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of a recombinant expression vector, and in particular, to determine the effect of a mutation on expression and phenotype. It will be appreciated that selectable markers can be introduced on a separate vector from the nucleic acid of interest.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Suitable host cells include a wide variety of prokaryotic and eukaryotic host cells. For example, the proteins of the invention may be expressed in bacterial cells such as E. coli, insect cells (using baculovirus), yeast cells or mammalian cells.

A nucleic acid molecule of the invention may also be chemically synthesized using standard techniques. Various methods of chemically synthesizing polydeoxy-nucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

IV. ANTIBODIES

In certain aspects of the invention, one or more antibodies may be produced to a TCL1 peptide of the present invention or a TCL1 peptide-HLA-A2 complex. These antibodies may be used, e.g., to treat a cancer or may be included in a cancer vaccine. In some embodiments, an antibody that selectively recognizes a TCL1 peptide or a TCL1 peptide-HLA-A2 complex may be administered to a subject, such as a human patient, to treat a B-cell malignancy such as a leukemia or a lymphoma.

In some embodiments, there are methods of inducing dendritic cell-(DC) mediated cell killing against a target cell expressing a targeted cell surface polypeptide comprising: a) contacting the target cell with a polypeptide comprising an antibody that selectively binds a TCL1 peptide-HLA-A2 complex; and b) exposing the target cell to dendritic cells under conditions that promote killing of the target cell.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with the present invention. Minibodies are sFv polypeptide chains which include oligomerization domains at their C-termini, separated from the sFv by a hinge region. Pack et al. (1992). The oligomerization domain comprises self-associating .alpha.-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in the present invention. Liu et al. (2003) describe "antibody like binding peptidomimetics" (ABiPs), which are peptides that act as pared-down antibodies and have certain advantages of longer serum half-life as well as less cumbersome synthesis methods.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

A. Methods for Generating Monoclonal Antibodies

The methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756, 687, 5,750,172, and 5,741,957.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, Pa.); low-dose Cyclophosphamide (CYP; 300 mg/m$^2$) (Johnson/Mead, N.J.), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196, 265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). cites). For example, where the immunized animal is a mouse, one may use P3-X63/Ag8, X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. See Yoo et al. (2002), for a discussion of myeloma expression systems.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71-74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

Further, expression of antibodies of the invention (or other moieties therefrom) from production cell lines can be enhanced using a number of known techniques. For example, the glutamine sythetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Another embodiment of the invention for producing antibodies according to the present invention is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments encompassed by the present invention can be synthesized using an automated peptide synthesizer, or by expression of full-length gene or of gene fragments in E. coli.

B. Antibody Conjugates

The present invention further provides antibodies against a TCL1 peptide of the present invention or a TCL1 peptide-HLA-A2 complex, generally of the monoclonal type, that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, antitumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotypes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti-cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody-directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$-carbon, $^{51}$chromium, $^{36}$-chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In another embodiment of the invention, the anti-(TCL1 peptide) antibodies or the anti-(TCL1 peptide-HLA-A2) antibodies may be linked to semiconductor nanocrystals such as those described in U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays of the present invention include, but are not limited to those described above, including group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,630,307 and 6,274,323.

In still further embodiments, the present invention concerns immunodetection methods for binding, purifying, removing, quantifying and/or otherwise generally detecting biological components such as T cells or that selectively bind or recognize a TCL1 peptide or a TCL1 peptide-HLA-A2 complex. In some embodiments, a tetramer assay may be used with the present invention. Tetramer assays generally involve generating soluble peptide-MHC tetramers that may bind antigen specific T lymphocytes, and methods for tetramer assays are described, e.g., in Altman et al. (1996). Some immunodetection methods that may be used include, e.g., enzyme linked immunosorbent assay (ELISA), radioimmunoassay (RIA), immunoradiometric assay, fluoroimmunoassay, chemiluminescent assay, bioluminescent assay, tetramer assay, and Western blot. The steps of various useful immunodetection methods have been described in the scientific literature, such as, e.g., Doolittle and Ben-Zeev, 1999; Gulbis and Galand, 1993; De Jager et al., 1993; and Nakamura et al., 1987, each incorporated herein by reference.

V. PHARMACEUTICAL PREPARATIONS

In select embodiments, it is contemplated that a TCL1 peptide of the present invention may be comprised in a vaccine composition and administered to a subject to induce a therapeutic immune response in the subject towards a cancer, such as a B cell malignancy, that expresses TCL1. A vaccine composition for pharmaceutical use in a subject may comprises a TCL1 peptide composition disclosed herein and a pharmaceutically acceptable carrier. Alternately, an antibody that selectively binds to a TCL1 peptide-HLA-A2 complex may be included in a pharmaceutically acceptable carrier.

The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington: The Science and Practice of Pharmacy, 21st edition, Pharmaceutical Press, 2011, incorporated herein by reference). Except insofar as any conventional carrier is incompatible with the active ingredient, its use in the vaccine compositions of the present invention is contemplated.

As used herein, a "protective immune response" refers to a response by the immune system of a mammalian host to a cancer. A protective immune response may provide a therapeutic effect for the treatment of a cancer, e.g., decreasing tumor size, increasing survival, etc.

In some embodiments, a vaccine composition of the present invention may comprise a TCL1 peptide or anti-(TCL1 peptide-HLA-A2 complex) antibody of the present invention. In some embodiments, TCL1 peptides to be included in a pharmaceutical preparation selectively bind HLA-A2. A vaccine composition comprising a TCL1 peptide or an antibody that selectively binds to a TCL1 peptide-HLA-A2 complex may be used to induce a protective immune response against a cancer that expresses TCL1.

A person having ordinary skill in the medical arts will appreciate that the actual dosage amount of a vaccine composition administered to an animal or human patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, vaccine compositions may comprise, for example, at least about 0.1% of a TCL1 peptide or anti-(TCL1 peptide-HLA-A2 complex) antibody. In other embodiments, the an active compound may comprise between about 2% to about 75% of the weight of the unit, or between about 25% to about 60%, for example, and any range derivable therein. As with many vaccine compositions, frequency of administration, as well as dosage, will vary among members of a population of animals or humans in ways that are predictable by one skilled in the art of immunology. By way of nonlimiting example, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1-36 week period. Preferably, 3 doses are administered, at intervals of 3-4 months, and booster vaccinations may be given periodically thereafter.

In some embodiments, a "suitable dose" is an amount of an TCL1 peptide or anti-(TCL1 peptide-HLA-A2 complex) antibody that, when administered as described above, is capable of raising an immune response in an immunized patient against a cancer. In general, the amount of peptide present in a suitable dose (or produced in situ by the nucleic acid in a dose) may range from about 0.01-100 mg per kg of host, from about 0.01-100 mg, preferably about 0.05-50 mg and more preferably about 0.1-10 mg. In some embodiments a TCL1 peptide may be administered in a dose of from about 0.25 mg to about 1 mg per each vaccine dose.

A vaccine composition of the present invention may comprise different types of carriers depending on whether it is to be administered in solid, liquid or aerosol form, and whether it needs to be sterile for such routes of administration as injection. A vaccine composition disclosed herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctivally, intravesicularlly, mucosally, intrapericardially, intraumbilically, intraocularly, orally, topically, locally, and by inhalation, injection, infusion, continuous infusion, lavage, and localized perfusion. A vaccine composition may also be administered to a subject via a catheter, in cremes, in lipid compositions, by ballistic particulate delivery, or by other method or any combination of the forgoing as would be known to one of ordinary skill in the art (see, for example, Remington: The Science and Practice of Pharmacy, 21$^{st}$. Ed. Lippincott Williams and Wilkins, 2005, incorporated herein by reference).

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Of particular interest in an aspect of the present invention is a vaccine composition that may be administered by microstructured transdermal or ballistic particulate delivery. Microstructures as carriers for vaccine formulation are a desirable configuration for vaccine applications and are widely known in the art (Gerstel and Place 1976 (U.S. Pat. No. 3,964,482); Ganderton and McAinsh 1974 (U.S. Pat. No. 3,814,097); U.S. Pat. Nos. 5,797,898, 5,770,219 and 5,783,208, and U.S. Patent Application 2005/0065463). Such a vaccine composition formulated for ballistic particulate delivery may comprise an isolated TCL1 peptide disclosed herein immobilized on a surface of a support substrate. In these embodiments, a support substrate can include, but is not limited to, a microcapsule, a microparticle, a microsphere, a nanocapsule, a nanoparticle, a nanosphere, or a combination thereof.

Microstructures or ballistic particles that serve as a support substrate for an TCL1 peptide or anti-(TCL1 peptide-HLA-A2 complex) antibody disclosed herein may be comprised of biodegradable material and non-biodegradable material, and such support substrates may be comprised of synthetic polymers, silica, lipids, carbohydrates, proteins, lectins, ionic agents, crosslinkers, and other microstructure components available in the art. Protocols and reagents for the immobilization of a peptide of the invention to a support substrate composed of such materials are widely available commercially and in the art.

In other embodiments, a vaccine composition comprises an immobilized or encapsulated TCL1 peptide or anti-(TCL1 peptide-HLA-A2 complex) antibody disclosed herein and a support substrate. In these embodiments, a support substrate can include, but is not limited to, a lipid microsphere, a lipid nanoparticle, an ethosome, a liposome, a niosome, a phospholipid, a sphingosome, a surfactant, a transferosome, an emulsion, or a combination thereof. The formation and use of liposomes and other lipid nano- and microcarrier formulations is generally known to those of ordinary skill in the art, and the use of liposomes, microparticles, nanocapsules and the like have gained widespread use in delivery of therapeutics (e.g., U.S. Pat. No. 5,741,516, specifically incorporated herein in its entirety by reference). Numerous methods of liposome and liposome-like preparations as potential drug carriers, including encapsulation of peptides, have been reviewed (U.S. Pat. Nos. 5,567,434; 5,552,157; 5,565,213; 5,738,868 and 5,795,587, each of which is specifically incorporated in its entirety by reference).

In addition to the methods of delivery described herein, a number of alternative techniques are also contemplated for administering the disclosed vaccine compositions. By way of nonlimiting example, a vaccine composition may be administered by sonophoresis (i.e., ultrasound) which has been used and described in U.S. Pat. No. 5,656,016 for enhancing the rate and efficacy of drug permeation into and through the circulatory system; intraosseous injection (U.S. Pat. No. 5,779,708), or feedback-controlled delivery (U.S. Pat. No. 5,697,899), and each of the patents in this paragraph is specifically incorporated herein in its entirety by reference.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

A peptide may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Sterile injectable solutions are prepared by incorporating the active peptides in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Detection and Vaccination Kits

A TCL1 peptide, an anti-(TCL1 peptide-HLA-A2 complex) antibody, or an anti-TCL1 peptide antibody of the present invention may be included in a kit. The TCL1 peptide or antibody in the kit may be detectably labeled or immobilized on a surface of a support substrate also comprised in the kit. The TCL1 peptide(s) or antibody may, for example, be provided in the kit in a suitable form, such as sterile, lyophilized, or both.

The support substrate comprised in a kit of the invention may be selected based on the method to be performed. By way of nonlimiting example, a support substrate may be a multi-well plate or microplate, a membrane, a filter, a paper, an emulsion, a bead, a microbead, a microsphere, a nanobead, a nanosphere, a nanoparticle, an ethosome, a liposome, a niosome, a transferosome, a dipstick, a card, a celluloid strip, a glass slide, a microslide, a biosensor, a lateral flow apparatus, a microchip, a comb, a silica particle, a magnetic particle, or a self-assembling monolayer.

As appropriate to the method being performed, a kit may further comprise one or more apparatuses for delivery of a composition to a subject or for otherwise handling a composition of the invention. By way of nonlimiting example, a kit may include an apparatus that is a syringe, an eye dropper, a ballistic particle applicator (e.g., applicators disclosed in U.S. Pat. Nos. 5,797,898, 5,770,219 and 5,783,208, and U.S. Patent Application 2005/0065463), a scoopula, a microslide cover, a test strip holder or cover, and such like.

A detection reagent for labeling a component of the kit may optionally be comprised in a kit for performing a method of the present invention. In particular embodiments, the labeling or detection reagent is selected from a group comprising reagents used commonly in the art and including, without limitation, radioactive elements, enzymes, molecules which absorb light in the UV range, and fluorophores such as fluorescein, rhodamine, auramine, Texas Red, AMCA blue and Lucifer Yellow. In other embodiments, a kit is provided comprising one or more container means and a BST protein agent already labeled with a detection reagent selected from a group comprising a radioactive element, an enzyme, a molecule which absorbs light in the UV range, and a fluorophore.

When reagents and/or components comprising a kit are provided in a lyophilized form (lyophilisate) or as a dry powder, the lyophilisate or powder can be reconstituted by the addition of a suitable solvent. In particular embodiments, the solvent may be a sterile, pharmaceutically acceptable buffer and/or other diluent. It is envisioned that such a solvent may also be provided as part of a kit.

When the components of a kit are provided in one and/or more liquid solutions, the liquid solution may be, by way of non-limiting example, a sterile, aqueous solution. The compositions may also be formulated into an administrative composition. In this case, the container means may itself be a syringe, pipette, topical applicator or the like, from which the formulation may be applied to an affected area of the body, injected into a subject, and/or applied to or mixed with the other components of the kit.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Patient Samples.

The Institutional Review Board of The University of Texas M. D. Anderson Cancer Center approved the study. An informed consent was obtained in accordance with the Declaration of Helsinki prior to collection of blood and tissue samples. Peripheral blood mononuclear cells (PBMC) were isolated from blood samples by density gradient separation. Tissue samples from lymphoma patients were processed into single-cell suspension and cryopreserved in aliquots.

Cell Lines.

MCL cell lines, Mino and Jeko-1; Burkitt's lymphoma cell line, Daudi; erythroleukemia cell line, K562; breast cancer cell line, MCF-7; and T2 hybridoma cells were cultured in RPMI 1640 medium supplemented with 10% fetal bovine serum, 10 mM HEPES, 1× Glutamax, 50 µM β-mercaptoethanol, 1 mM sodium pyruvate, 100 U/mL penicillin+100 µg/mL streptomycin, and 10 µg/mL gentamicin (all reagents from Invitrogen, Carlsbad, Calif.) at 37° C. and 5% $CO_2$ in air.

Tumor and Immune Cell Subset Isolation.

Tumor cells, T cells from tumor samples, and normal peripheral blood B and T cells were isolated by magnetic cell separation (MACS, Miltenyi Biotec, Auburn, Calif.) and the purity confirmed by flow cytometry as previously described (Malyguine et al., 2004; Lee et al., 2008). The procedure yielded >90% purity of tumor B cells, tumor infiltrating T cells, and normal B and T cells (data not shown).

Reagents.

Mouse anti-human antibodies against CD3, CD4, CD8, CD10, CD20, IFN-γ, CD38, IgD, CD19, CD34, CD16, CD56, PD-1, CD160, CTLA-4, and CD244 were obtained from BD Biosciences, San Jose, Calif.; anti-human BTLA from Biolegend, San Diego, Calif.; and anti-human LAG3 from Alexis Biochemicals, NY. Enzyme-linked immunosorbent assay (ELISA) kits for IFN-γ were obtained from R&D Systems, Minneapolis, Minn. All peptides were synthesized by Sigma-Aldrich, St Louis, Mo. to greater than 70% purity and dissolved in dimethyl sulfoxide (Sigma-Aldrich). Phycoerythrin (PE)-conjugated tetramers were synthesized by MHC Tetramer Lab, Protein Chemistry Core of Baylor College of Medicine, Houston, Tex. TCL1 and β-actin antibodies for Western blotting were obtained from Cell Signaling Technology, Beverly, Mass. Anti-human HLA-ABC (clone W6/32, eBioscience, San Diego, Calif.), anti-HLA-DP-DQDR (clone TÜ39, BD Biosciences), anti-HLA A2 (clone BB7.2, BD Biosciences), mouse IgG2a isotype control (eBioscience, Cat#16-4724-81) were used for HLA-blocking studies. Blocking antibody against HLA-B and C was a kind gift from Paul Robbins, National Cancer Institute, National Institutes of Health, Bethesda, Md.

Analysis of cDNA Microarray Data.

The relative expression of TCL1 mRNA in lymphoma cells and normal tissues was determined from publicly available cDNA microarray datasets from the Oncomine database (https://www.oncomine.org/resource/login.html). Log 2-transformed data was analyzed for relative levels of gene expression.

Real-Time PCR.

FirstChoice® Human Total RNA Survey Panel (Cat# AM6000) containing 20 normal human tissues total RNA and human lymph node total RNA (Cat#AM7894) were obtained from Applied Biosystems, Foster City, Calif. Total RNA was extracted from purified lymphoma cells or peripheral blood B and T cells using Trizol (Invitrogen). About 10 μg of total RNA from each source was reverse transcribed into cDNA with Superscript III kit (Invitrogen). Quantitative PCR was performed with Taqman real-time PCR kit (Applied Biosystems), and TCL1 (Applied Biosystems, Cat # Hs00951350_m1) and β-actin primers (Applied Biosystems, Cat# Hs99999903_m1) using the following conditions: 50° C. for 2 min, 94° C. for 10 min, followed by 94° C. for 15 sec, 60° C. for 60 sec for 40 cycles on Applied Biosystems StepOne™/StepOnePlus™ Real-Time PCR System. The expression of TCL1 mRNA relative to the β-actin mRNA was calculated in each sample.

Immunohistochemistry.

All tumor tissues were obtained form the M. D. Anderson Lymphoma Tissue Bank. Briefly, formalin-fixed, paraffin-embedded tissue sections from different lymphomas (DLBCL, FL, MCL, CLL, and splenic marginal zone lymphoma [SMZL]) and reactive tonsils were deparaffinized, and heat-induced antigen retrieval was performed as per manufacturer's instructions (Vector Labs, Burlingame, Calif.). Sections were incubated for 10 minutes with TBS containing 3% bovine serum albumin (BSA) to block non-specific staining. Next, specimens were incubated overnight at 4° C. with the primary antibody against TCL-1 (Cell Signaling Technology, Beverly, Mass.). Antibody binding was detected using a secondary antibody in blocking buffer and staining was visualized using 3,3'-diaminobenzidine (DAB) (Vector Labs). Digital photomicrographs were acquired using DP Controller software mounted on a BX41 inverted microscope (Olympus, Center Valley, Pa.).

Flow cytometry. For intracellular staining, tumor or normal B cells were first surface stained with CD3 and CD20 and then fixed and permeabilized using BD Biosciences Cytofix/Cytoperm™ Plus Fixation/Permeabilization kit as per manufacturer's instructions. Cells were then stained with mouse anti-human-TCL1 Alexa Fluor® 647 antibody (eBioscience, Cat#51-6699-73) or Alexa Fluor® 647 Mouse IgG2b isotype control antibody (eBiosciences, Cat#51-4732) for 30 mM at 4° C. After two washes, samples were acquired on a FACS Calibur (BD Biosciences) and analyzed using Cell Quest Pro (BD Biosciences) or FlowJo (Tree Star, Inc., Ashland, Oreg.) software. Intracellular cytokine staining was performed as previously described (Malyguine et al., 2004; Lee et al., 2008). For tetramer staining, PE-conjugated TCL1$_{71-78}$ tetramer or HIV Gag$_{77-85}$ tetramer and FITC-conjugated mouse anti-human CD8 antibody were mixed with the cells in 50 μl volume for 30 minutes at room temperature, washed twice, and analyzed by a flow cytometry.

Western Blotting.

Approximately 50 μg of total cell protein was extracted from tumor or normal B cells after cell lysis in a buffer composed of 50 mM Tris-Cl (pH 7.4), 5 mM EDTA, 150 mM NaCl, 0.5% Triton-X 100, 1 mg/mL leupeptin and aprotinin, and 1 mM PMSF. Protein content of the lysates was quantified by the Bradford assay (Bio-Rad, Hercules, Calif.) and 25 μg of total protein was dissolved in Laemmli sodium dodecyl sulfate polyacrylamide gel electrophoresis (SDS-PAGE) sample buffer prior to separation in 15% SDS-PAGE gels. After electrophoresis, proteins were transferred to a nitrocellulose membrane (Bio-Rad) for western blotting with mouse anti-human-TCL1 antibody (eBioscience, Cat#14-6699) (1:200 dilution) for 1 h at room temperature or at 4° C. overnight. Bound antibodies were detected with goat anti-mouse horseradish peroxidase-conjugated secondary antibody diluted at 1:10,000 and SuperSignal West Pico Chemiluminescent Substrate (Thermo Scientific, Rockford, Ill.).

HLA-A2-Binding Assay.

TAP-deficient T2 cells were incubated with 20 μg/ml of peptides and 3 μg/ml of β$_2$-microglobulin (Sigma-Aldrich, Cat # M4890) for 24 hours at 37° C. and 5% $CO_2$ in air. The cells were then stained with anti-HLA-A2 PE antibody (BD Biosciences, Cat #560168), and the level of HLA-A2 expression was determined by flow cytometry. The binding affinity of the peptide to HLA-A2 (T2 binding index) was quantified as follows: (Mean fluorescence intensity [MFI] of HLA-A2 with peptide—MFI of HLA-A2 without peptide)/(MFI of HLA-A2 without peptide).

Generation of Peptide-Specific T-Cell Lines.

Peptide-specific T-cell lines were generated from HLA-A2$^+$ normal donors and patients using methods previously reported (Hida et al., 2002). Briefly, PBMCs ($1 \times 10^5$ cells/well) were stimulated with 10 μg/ml of each peptide in quadruplicate in a 96-well, U-bottom-microculture plate (Corning Incorporated, Lowell, Mass.) in 200 μl of culture medium. The culture medium consisted of 50% AIM-V medium (Invitrogen), 50% RPMI1640 medium (Invitrogen), 10% human AB serum (Valley Biomedical, Winchester, Va.), and 100 IU/ml of interleukin-2 (IL-2). Cells were restimulated with the corresponding peptide every 3 days. After 5 stimulations, T cells from each well were washed and incubated with T2 cells in the presence or absence of the corresponding peptide. After 18 hours, the production of interferon (IFN)-γ was determined in the supernatants by ELISA. T cells that secreted large amount of IFN-γ were further expanded by rapid expansion protocol to obtain sufficient number of cells for additional functional assays as previously described (Lee et al., 2008).

Cytotoxicity Assay.

T2 cells were cultured overnight with 40 μg/ml peptide in the presence of 3 μg/ml β$_2$-microglobulin, washed twice, labeled with chromium-51 ($^{51}$Cr) for 1 hour at 37° C., and used as targets in cytotoxicity assay. Primary tumor cells were isolated from PBMC or biopsy samples of lymphoma patients by MACS prior to labeling with $^{51}$Cr. Target cells ($1 \times 10^4$ cells/well) were incubated with the effector T cells at the indicated ratios in 96-well round-bottom plates at 37° C. for 4 hours, and target cell lysis was determined by chromium release into the supernatants. Spontaneous lysis was determined from the supernatant of target cells cultured without effector cells, and the maximal lysis was determined from the supernatant of target cells cultured with 1% Triton X-100. The specific lysis of target cells was calculated as follows: (Experimental lysis−Spontaneous lysis)×100/(Maximal lysis−Spontaneous lysis). For HLA-blocking studies, target cells were incubated for 30 minutes with 20 µg/ml of the anti-HLA blocking antibodies prior to co-culturing with the effector T cells. All assays were performed in triplicate wells and repeated at least two times.

Statistical Analysis.

The Student t test was used to compare various experimental groups. P values <0.05 were considered statistically significant. Unless otherwise indicated, means and standard deviations are shown.

Example 2

Figure 1B:
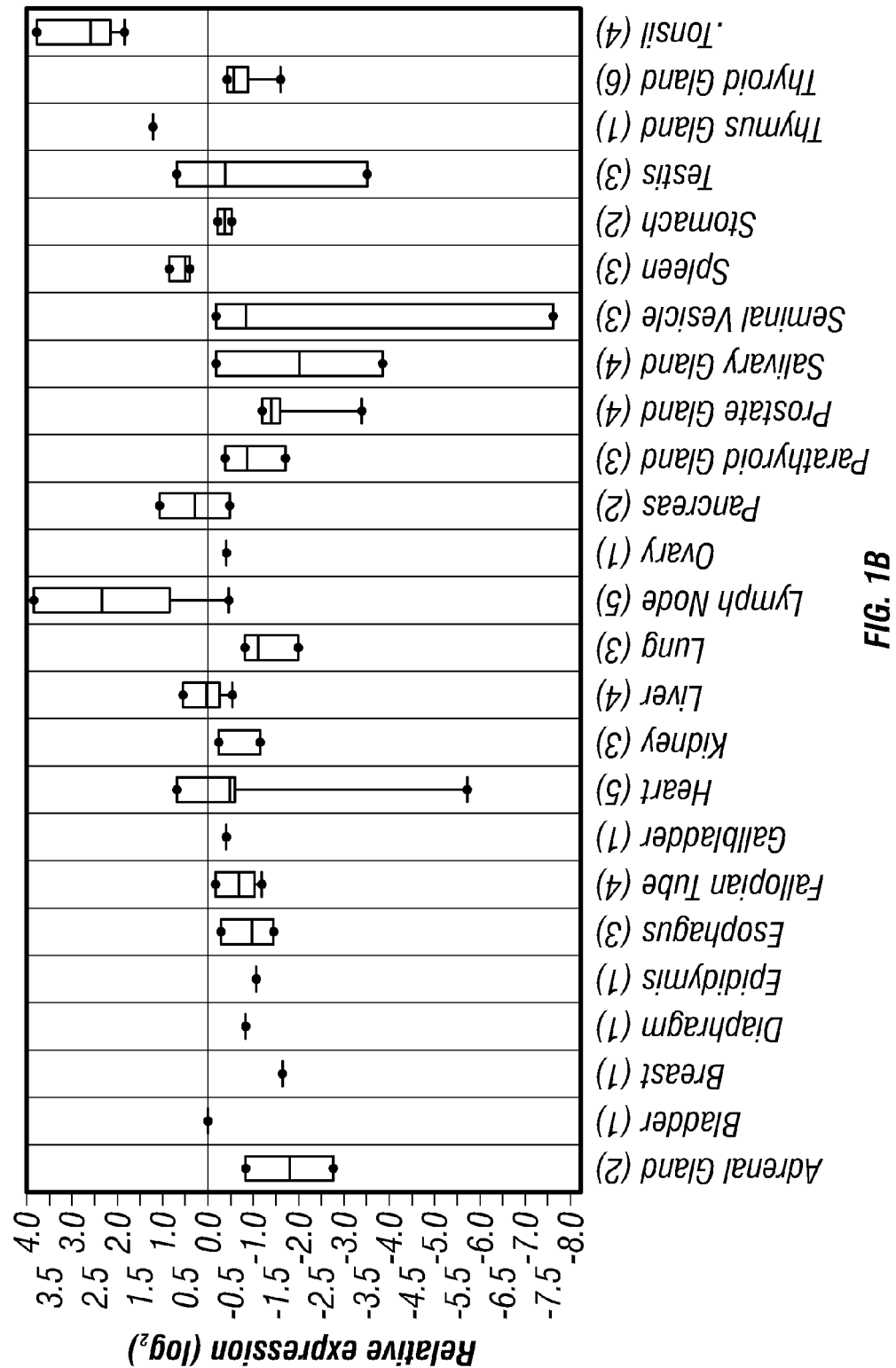
Figure 1C:
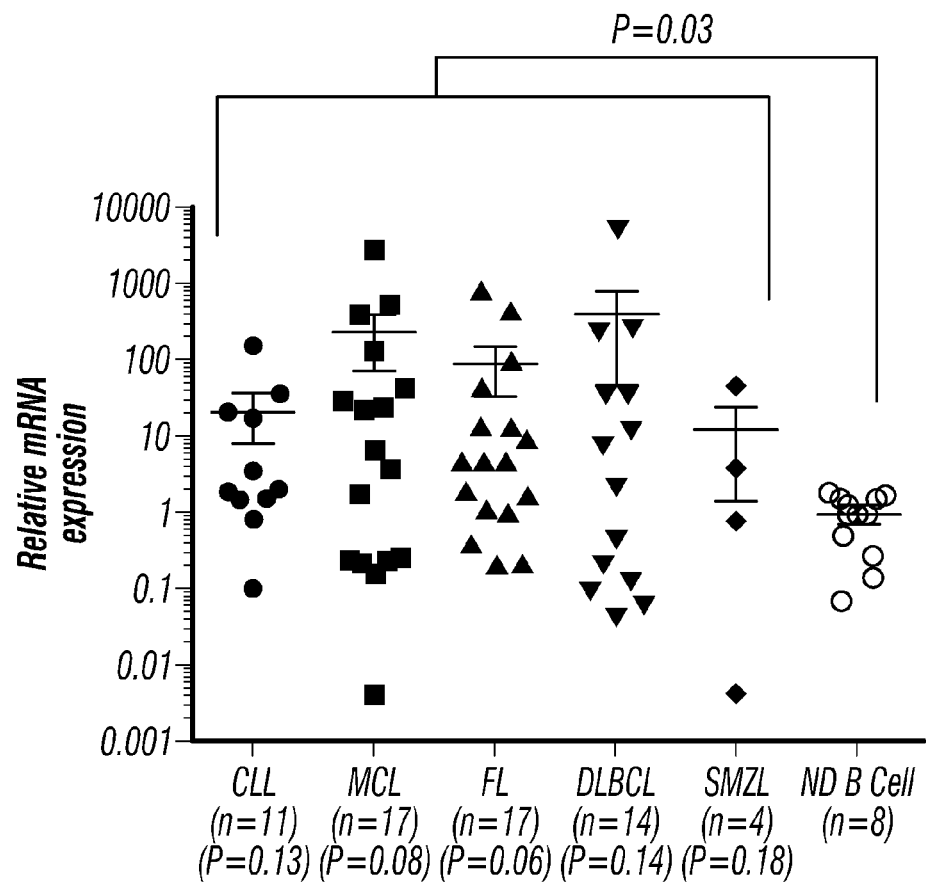
Figure 1D:
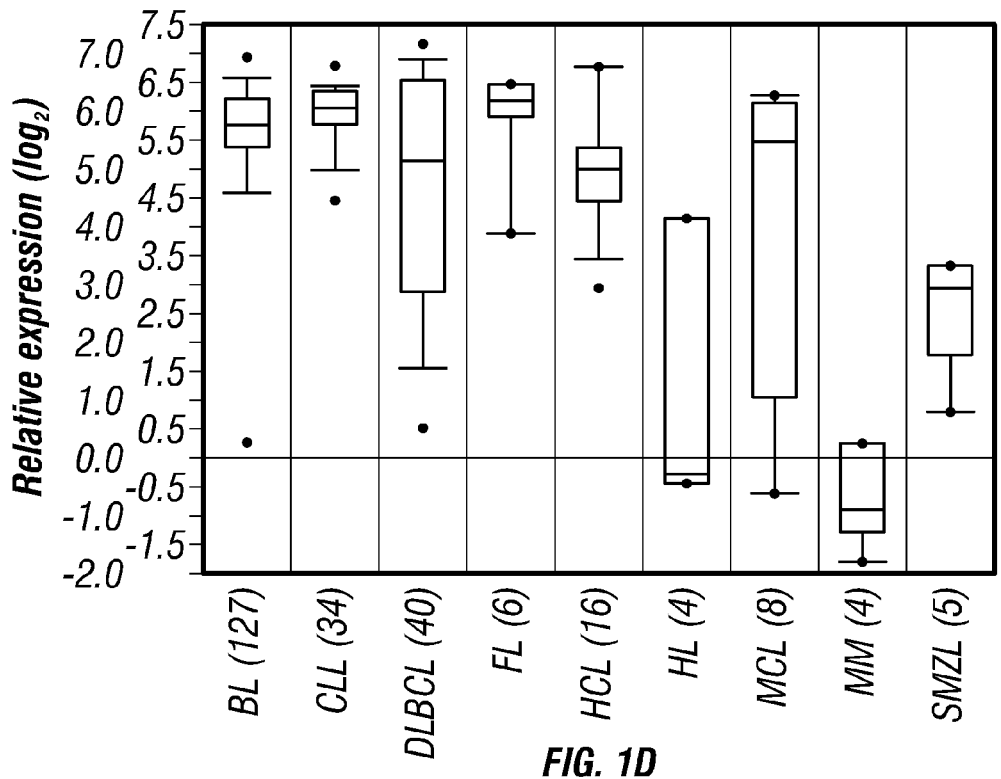

TCL1 is a Shared Tumor-Associated Antigen for Immunotherapy Against B-Cell Lymphomas TCL1 is Hyperexpressed in Multiple B-Cell Lymphomas To determine the expression pattern of TCL1 in normal adult tissues, the inventors performed real-time PCR assay on RNA derived from 21 tissues and peripheral blood B and T cells obtained from normal adults. Consistent with previous reports (Aggarwal et al., 2008; Said et al., 2001; Narducci et al., 2000; Herling et al., 2007) the inventors detected TCL1 mRNA in peripheral blood B cells and two normal lymphoid tissues, lymph node and spleen (FIG. 1A). The inventors also found very low levels of TCL1 mRNA in testis. However, TCL1 mRNA was not detected in peripheral blood T cells and tissues from small intestine, thymus, thyroid, trachea, heart, esophagus, kidney, liver, lung, adipose tissue, bladder, brain, ovary, placenta, prostate, skeletal muscle, colon, and cervix. Our results were also consistent with the expression pattern of TCL1 mRNA observed in cDNA microarray data from normal tissues in Oncomine database (FIG. 1B). Since TCL1 is selectively expressed in normal B cells (FIG. 1A), the inventors compared the expression level of TCL1 mRNA in B-cell lymphomas with peripheral blood B cells from normal donors. The inventors observed that TCL1 mRNA was hyperexpressed in tumor cells isolated from FL, CLL, MCL, DLBCL, and SMZL, as compared with normal B cells (P=0.02) (FIG. 1C). However, when each lymphoma subtype was compared with normal B cells, we found that there was a trend towards higher expression of TCL1 in lymphoma samples but it did not reach statistical significance probably due to the smaller sample size. Analysis of publicly available cDNA microarray data similarly showed that TCL1 mRNA was hyperexpressed in FL, CLL, MCL, SMZL, and DLBCL (FIG. 1D). In addition, TCL1 mRNA was hyperexpressed in Burkitt's lymphoma and hairy cell leukemia, but not in Hodgkin lymphoma and multiple myeloma (FIG. 1D).

Figure 2A:
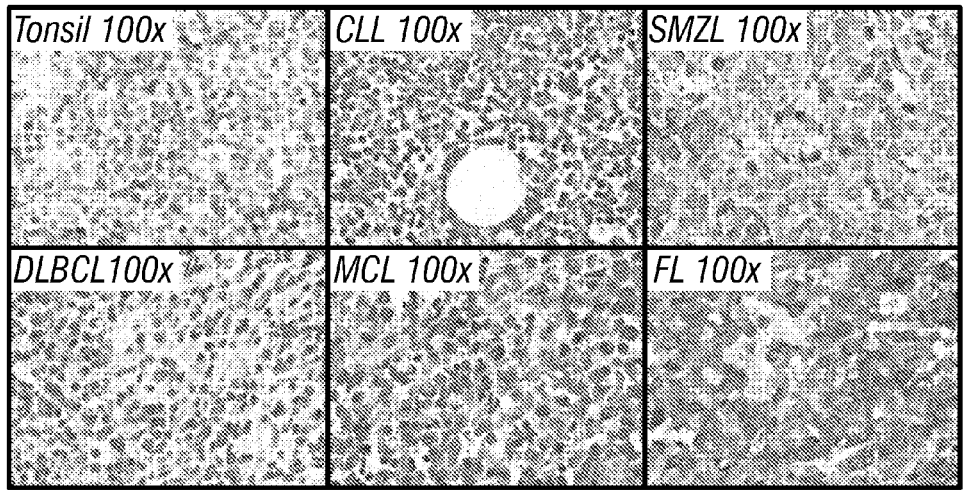
FIGS. 2A-C: TCL1 protein is hyperexpressed in multiple B cell lymphomas.
Figure 2B:
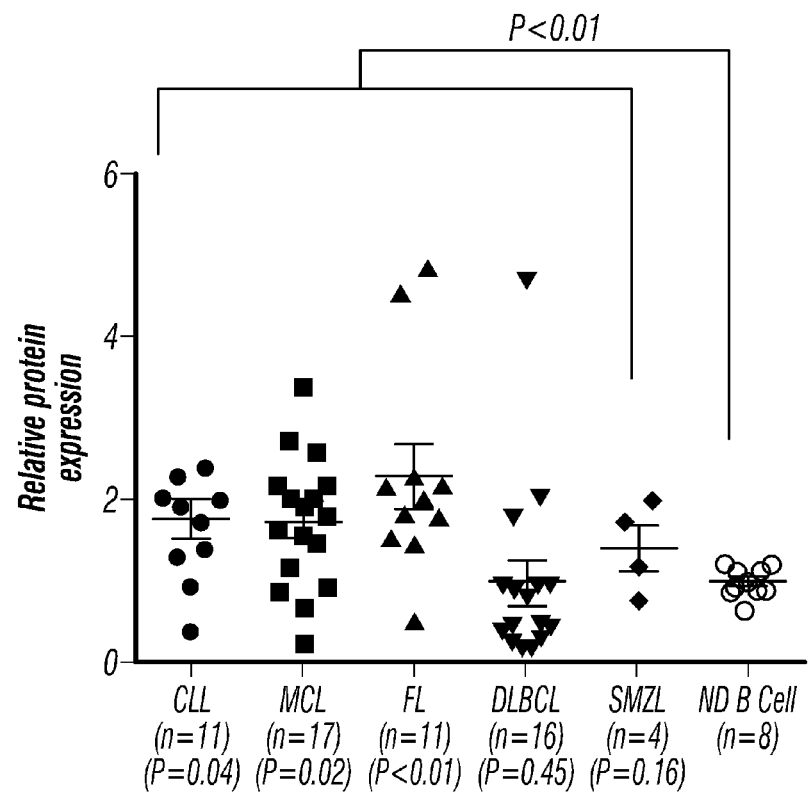
Figure 2C:
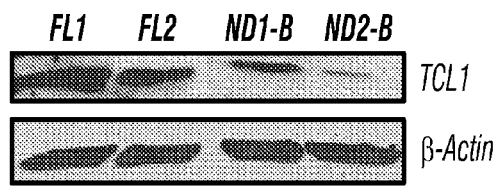
Figure 13A:
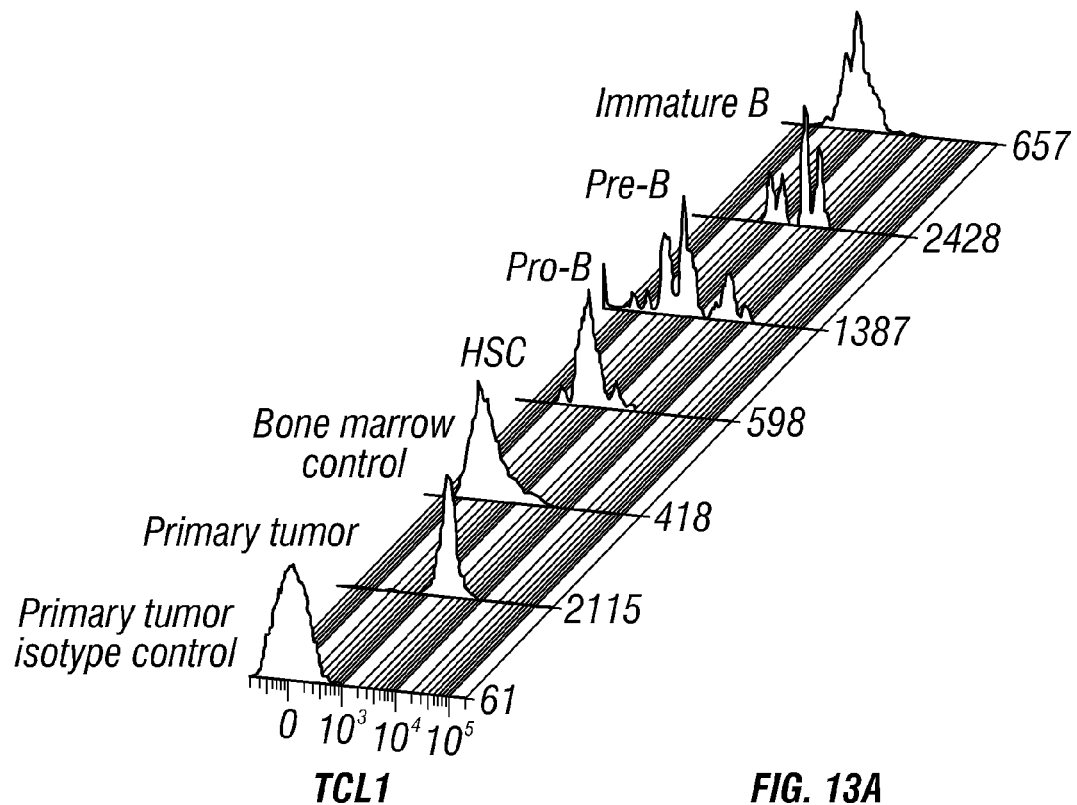
FIGS. 13A-C. TCL1 expression in B cell progenitors, mature B cell subsets, and immature T cells.
Figure 13B:
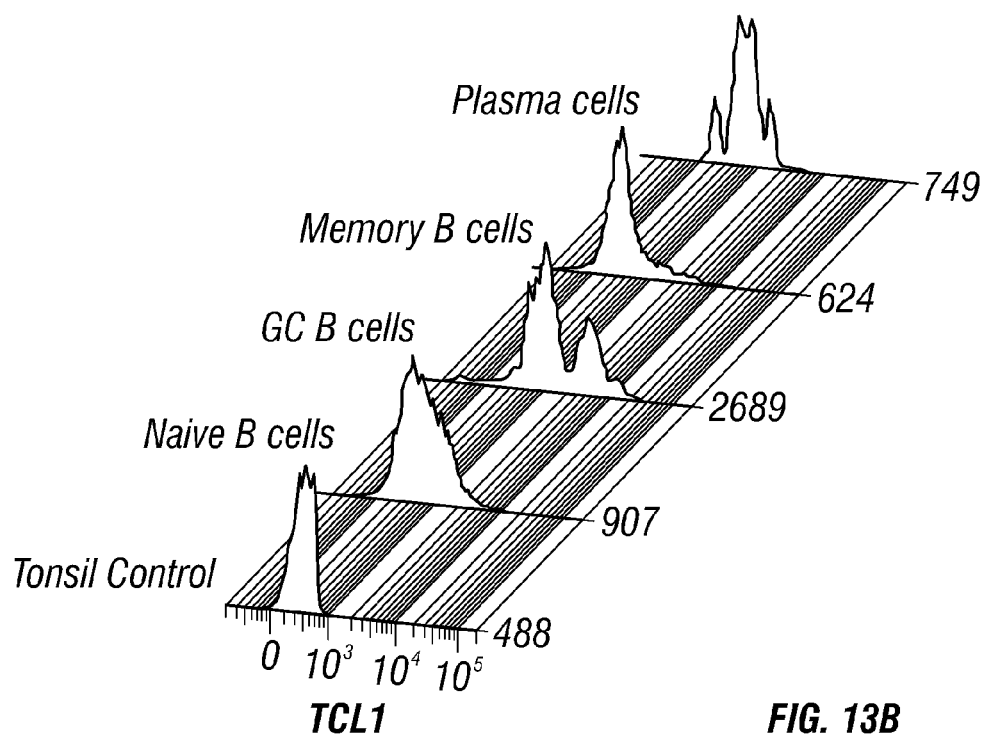
Figure 13C:
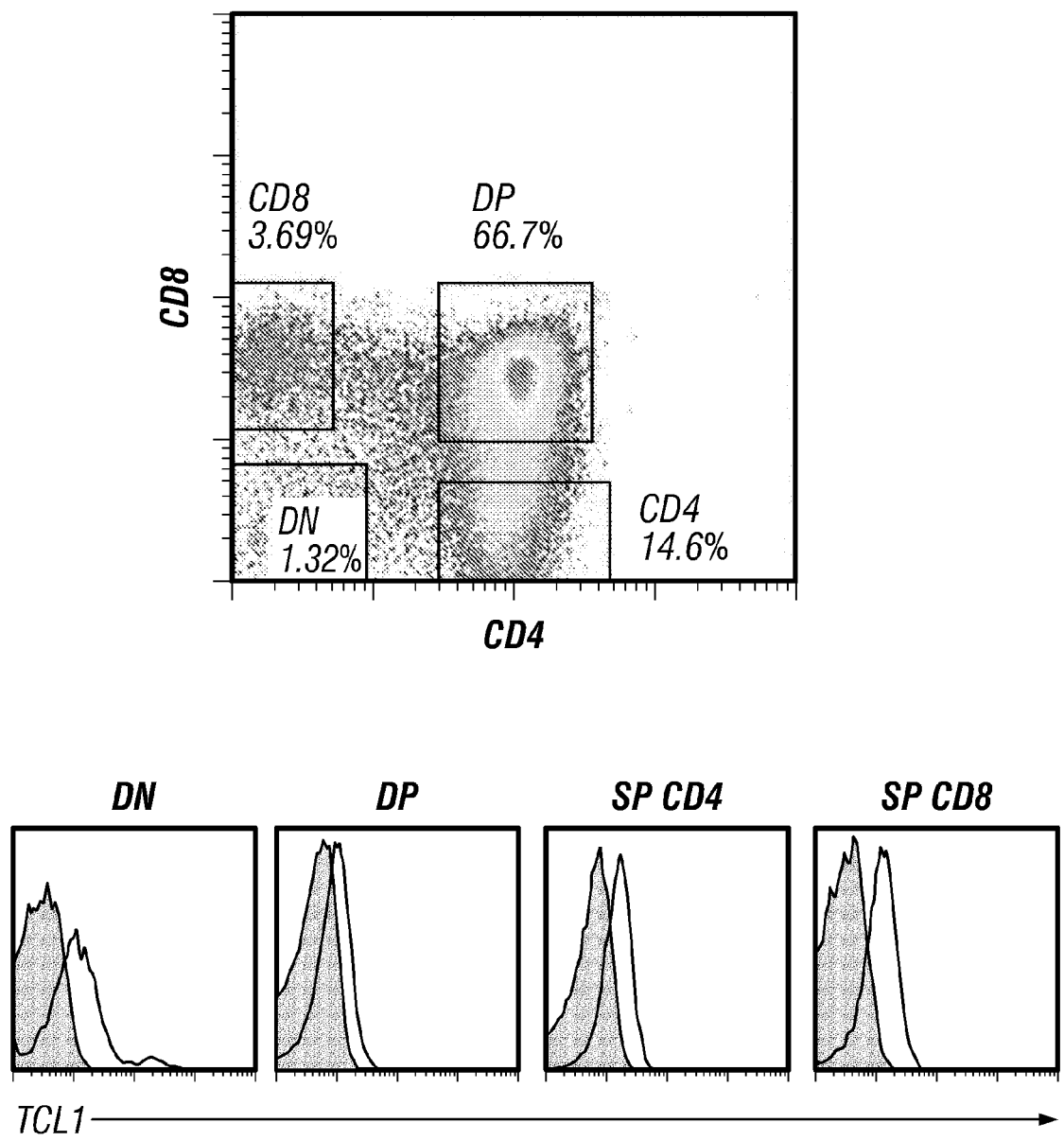

To determine the expression of TCL1 protein in lymphomas, the inventors performed immunohistochemistry, flow cytometry, and Western blotting. As compared to reactive tonsils or peripheral blood B cells, TCL1 protein was hyperexpressed in FL, CLL, MCL, DLCL, and SMZL (FIGS. 2A-C). By flow cytometry, we found that the TCL1 protein was significantly hyperexpressed in tumor cells when all lymphomas were compared with normal B cells (P<0.01) but only in CLL (P=0.04), MCL (P=0.02), and FL (P<0.01) when they were compared individually (FIG. 2B). Furthermore, we found that TCL1 was not expressed in CD34$^+$ hematopoietic stem cells but is expressed in a subset of pro-B, pre-B, and immature B cells in normal human bone marrow samples (FIG. 13A). To determine the subset of mature B cells that express TCL1, we analyzed normal human tonsil samples. We found that TCL1 was present in naïve and GC B cells and was down regulated in memory B cells and plasma cells (FIG. 13B). Amongst immature thymocytes, TCL1 was expressed in a subset of double-negative thymocytes but was very low or absent in double-positive, CD4 single-positive, and CD8 single-positive thymocytes (FIG. 13C). This pattern of expression of TCL1 in normal B cell progenitors, mature B cell subsets, and immature thymocytes was consistent with prior reports in the literature (Aggarwal et al., 2008; Teitell, 2005; Said et al., 2001; Narducci et al., 2000; Herling et al., 2007). Taken together, these results suggest that TCL1 is expressed at low levels in normal B cells and is hyperexpressed in multiple B-cell lymphomas and their precursors and, therefore, may potentially serve as a shared tumor-associated antigen for development of active immunotherapy against these malignancies.

TCL1-Specific T Cells can be Generated from Normal Donors

Figure 3A:
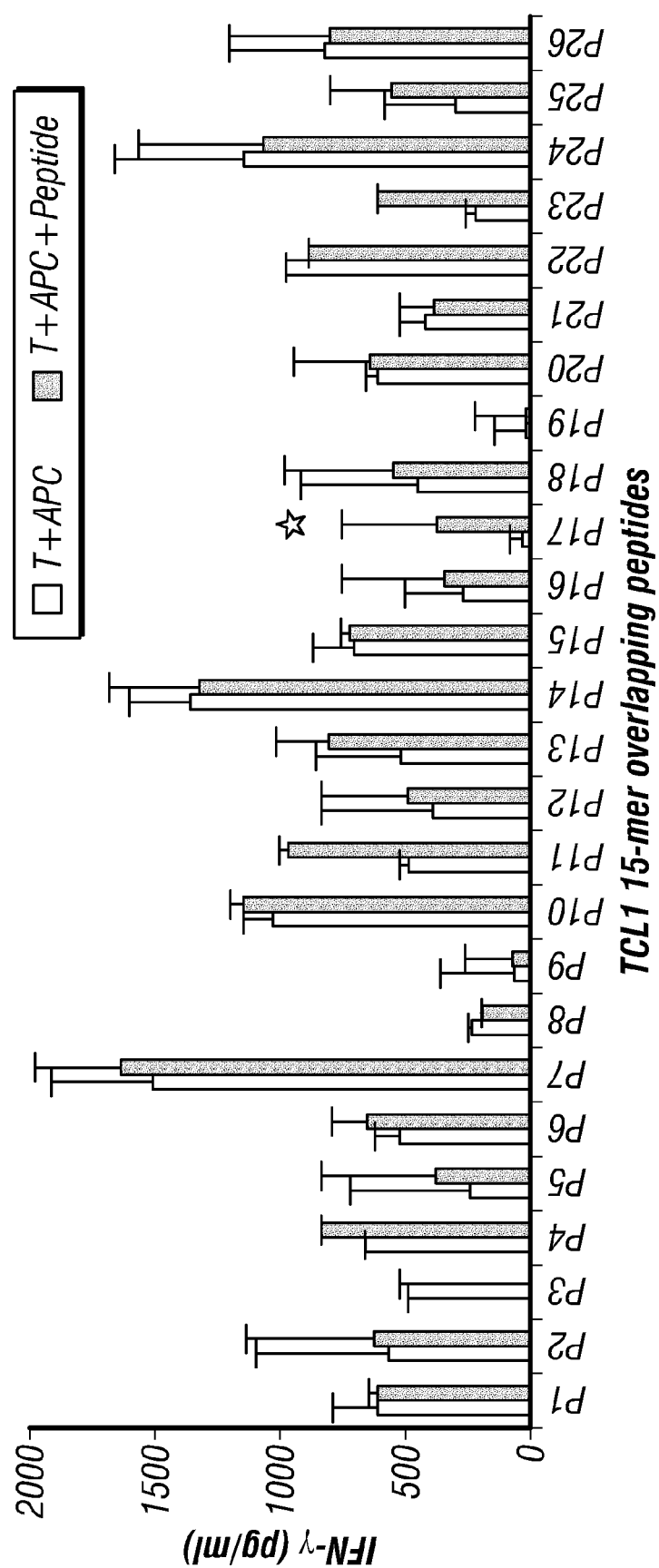
FIGS. 3A-E: TCL1-specific cytotoxic T cells can be generated from normal donors.
Figure 3C:
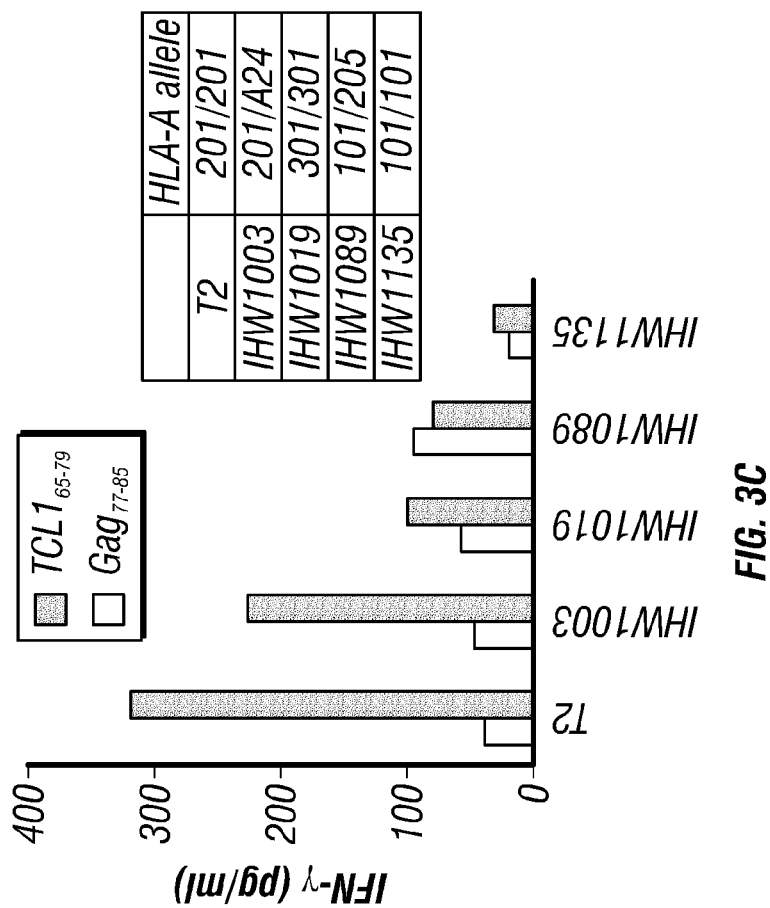
Figure 3B:
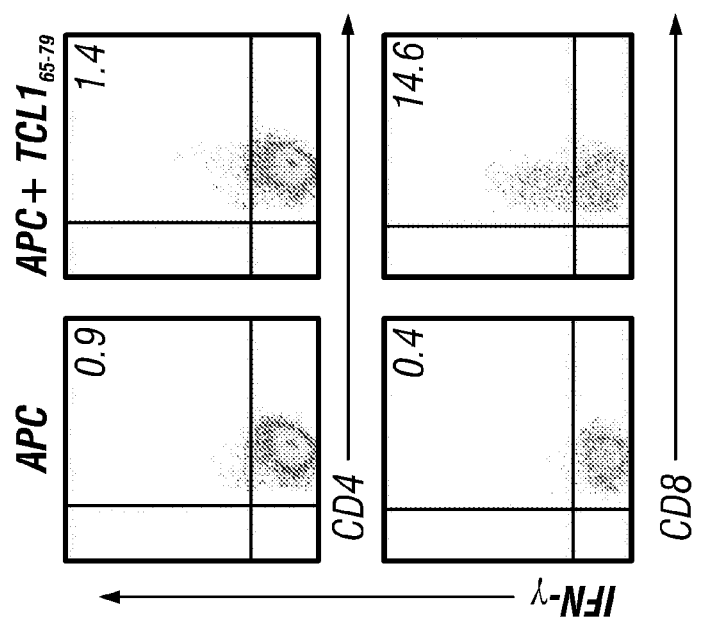
Figure 14:
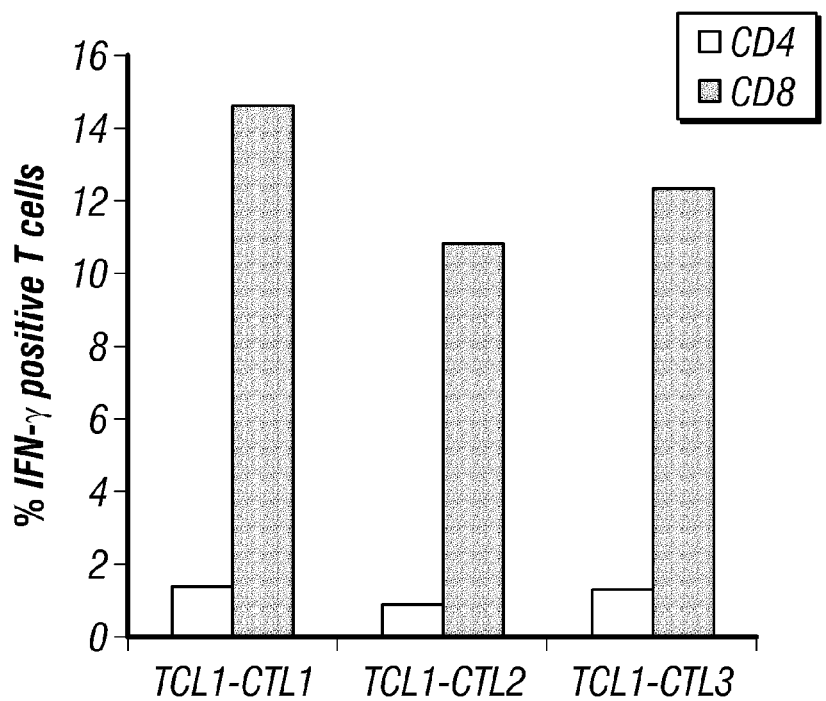
FIG. 14. Percentage of TCL1-specific T cells in T cell lines generated from normal donors. T cell lines generated from three HLA-A2$^+$ normal donors using TCL1$_{65-79}$ peptide were incubated with autologous CD3-depleted PBMC as antigen-presenting cells in the presence or absence of the TCL1$_{65-79}$ peptide, and intracellular cytokine assay was performed. The percentage of CD4$^+$ and CD8$^+$ T cells producing IFN-γ above the background are shown.

To determine whether TCL1 is immunogenic, the inventors synthesized overlapping 15-mer peptides spanning the entire length of the TCL1 protein (Table 2) and stimulated PBMC from HLA-A2$^+$ normal donors to generate TCL1-specific T cells, as described in the Materials and Methods (Hida et al., 2002). The inventors found that TCL1$_{65-79}$ peptide (TQIGPSLLPIMWQLY) (SEQ ID NO:1) consistently induced peptide-specific IFN-γ-producing T cells in three HLA-A2$^+$ normal donors (FIG. 3A). By intracellular cytokine assay, the inventors observed that CD8$^+$ but not CD4$^+$ T cells produced IFN-γ in response to TCL1$_{65-79}$ peptide stimulation (FIG. 3B, and FIG. 14).

Figure 3E:
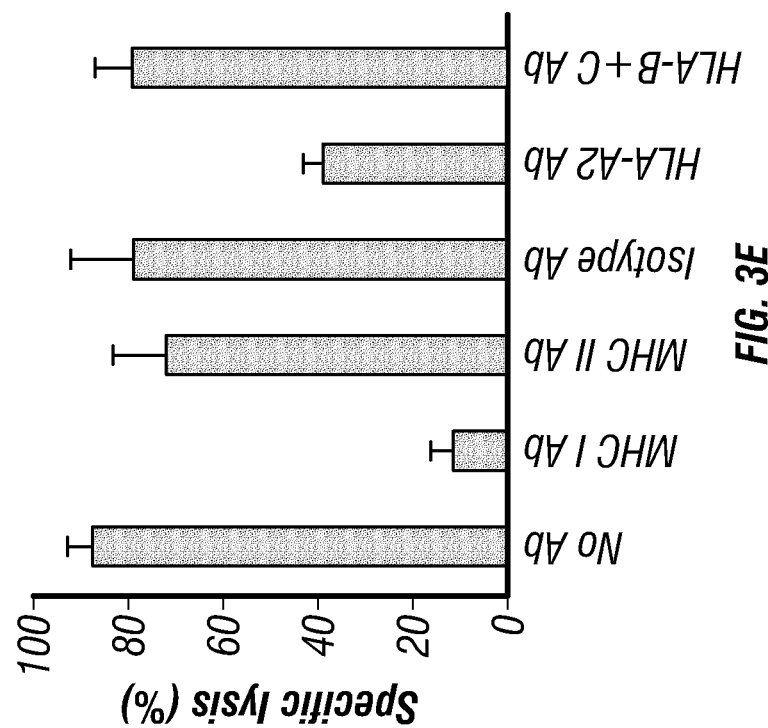
Figure 3D:
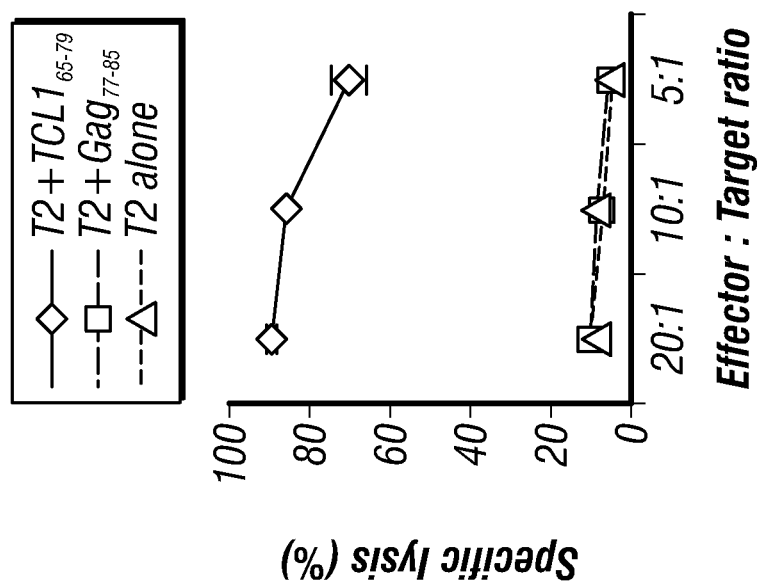

To determine whether HLA-A2 is the restriction element for the TCL1$_{65-79}$ peptide-reactive CD8$^+$ T cells, the inventors co-cultured the T cells with a panel of peptide-pulsed EBV-transformed B lymphoblastoid cell lines that were mismatched at the HLA-A locus. The inventors observed significant production of IFN-γ when the TCL1$_{65-79}$ peptide was presented by IHW1003 cells that expressed HLA-A2 and HLA-A24 but not by antigen presenting cells expressing other HLA-A alleles (FIG. 3C). Interestingly, T2 cells also induced IFN-γ production by TCL1$_{65-79}$ peptide-reactive T cells. As T2 cells are TAP deficient, it is unlikely that the TCL1$_{65-79}$ peptide was processed and presented as a shorter peptide by T2 cells. Since peptides longer than nine amino acids may also bind to MHC class I molecules (Guo et al., 1992; Burrows et al., 2006; Samino et al., 2006; Stryhn et al., 2000; Collins et al., 1994; Blanchard and Shastri, 2008), the inventors reasoned that the unprocessed TCL1$_{65-79}$ peptide was being presented by T2 cells. To further confirm this, the inventors tested whether the TCL1$_{65-79}$ peptide-reactive T cells would lyse peptide-pulsed HLA-A2$^+$ T2 cells. The inventors observed significant lysis of TCL1$_{65-79}$ peptide-pulsed T2 cells but not unpulsed T2 cells or T2 cells pulsed with control HIV Gag$_{77-85}$ peptide (FIG. 3D). The lysis of TCL1$_{65-79}$ peptide-pulsed T2 cells was inhibited by MHC class I and HLA-A2 blocking antibodies but not by MHC class II and HLA-B and C blocking antibodies or isotype control antibody, confirming HLA-A*0201 as the restriction element for this peptide (FIG. 3E). Collectively, these results suggested that the CD8$^+$ T cells generated against TCL1$_{65-79}$ peptide were peptide-specific and recognized the peptide in the context of HLA-A2.

TCL1$_{71-78}$ is the Minimal HLA-A2-Binding Epitope

Figure 4A:
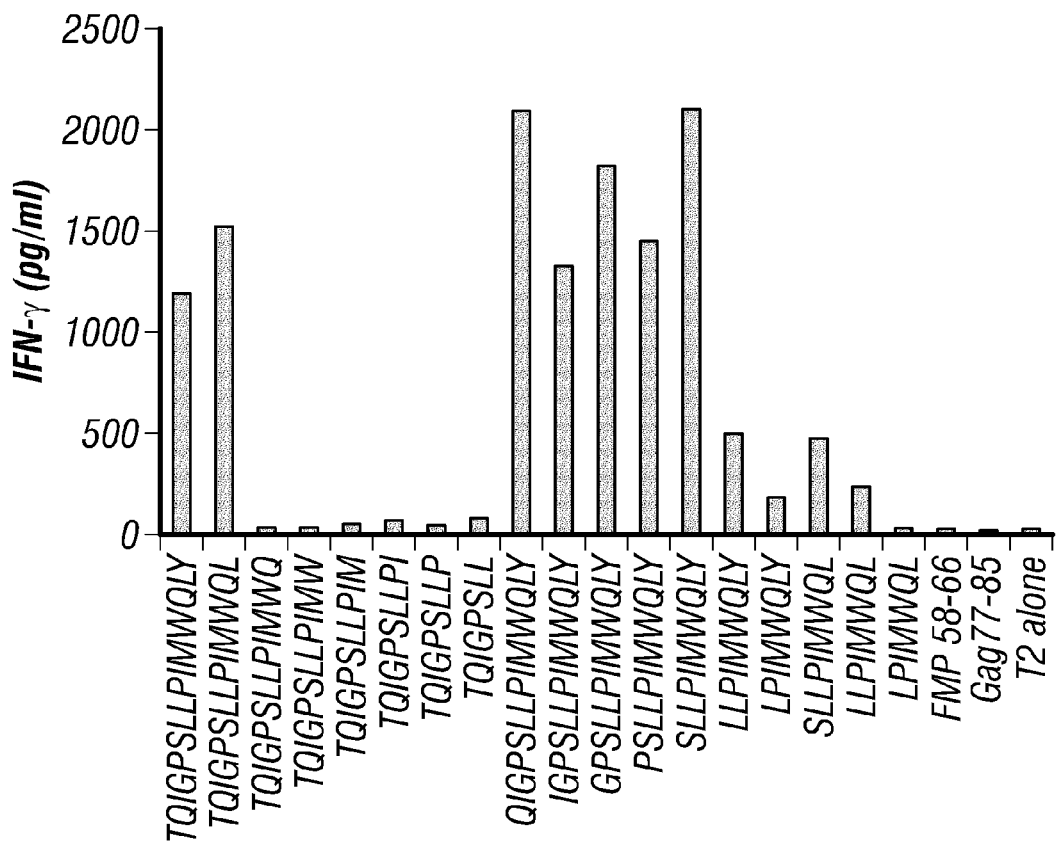
FIGS. 4A-D: $TCL1_{71-78}$ is the minimal HLA-A*0201-binding peptide.
Figure 4B:
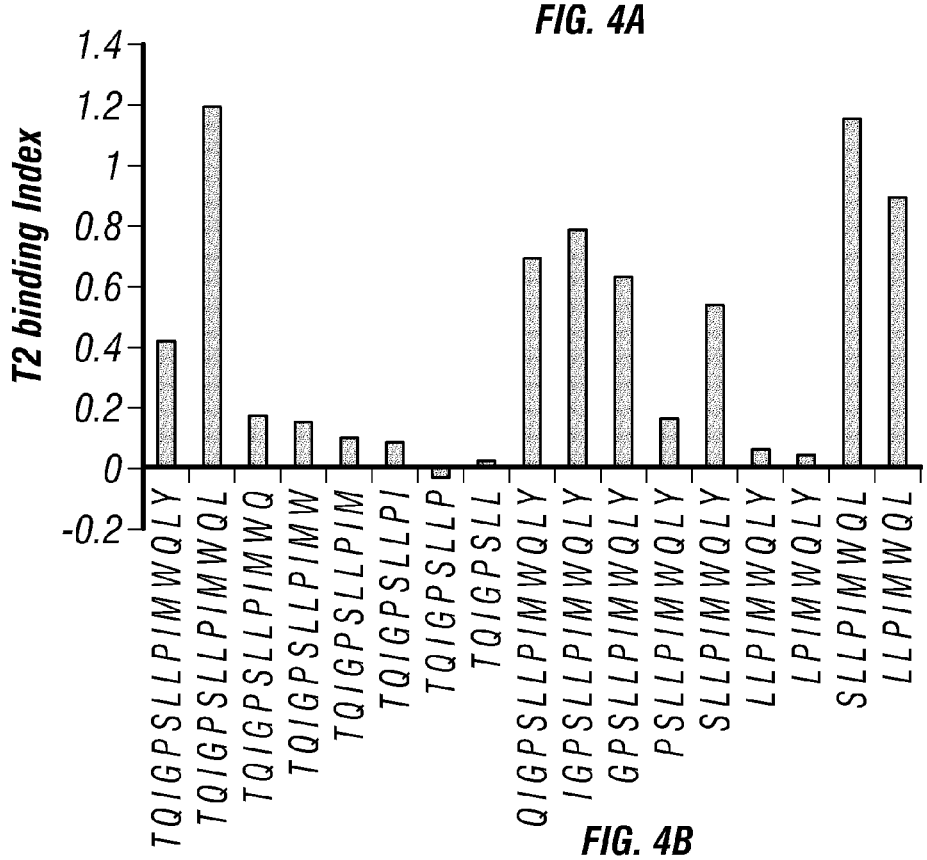
Figure 4C:
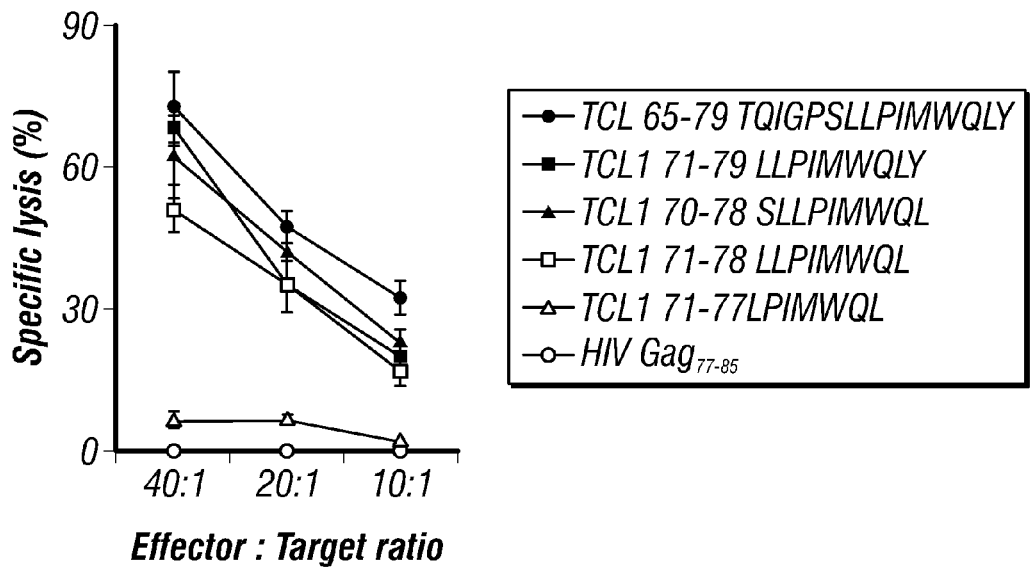
Figure 4D:
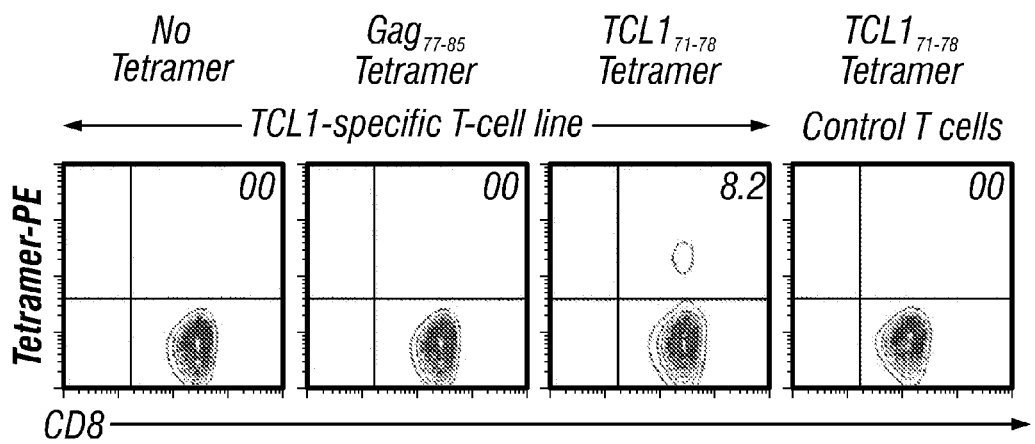
Figure 15:
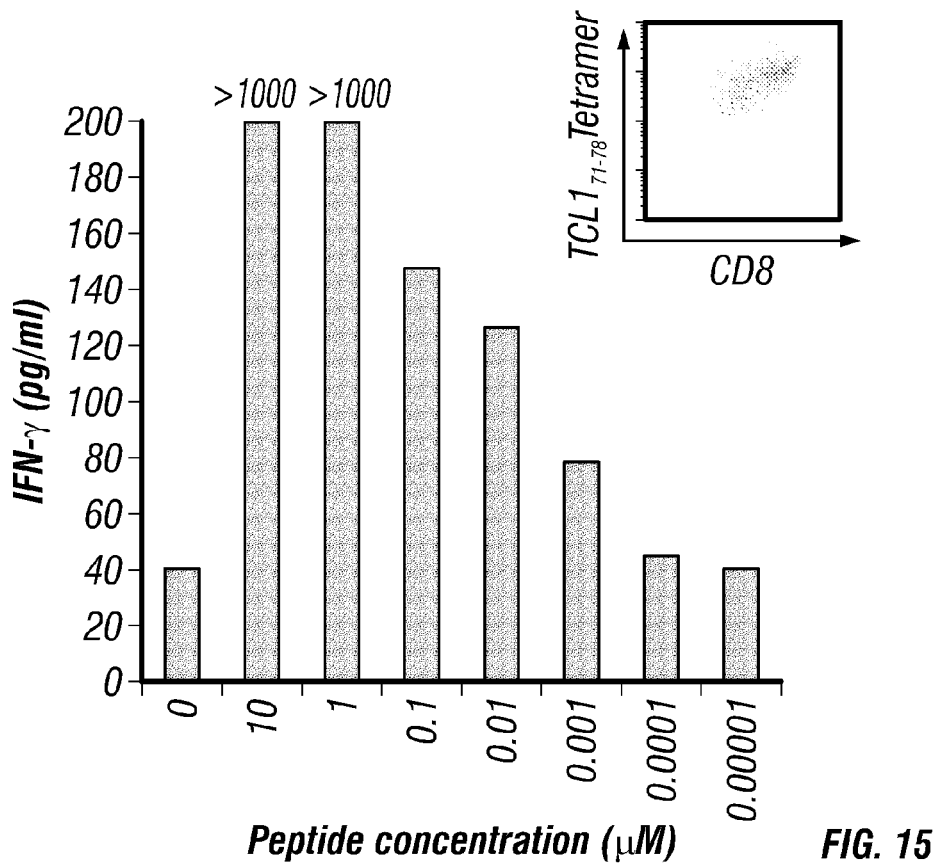
FIG. 15. Avidity of TCL1-specific CTL. TCL1$_{71-78}$ tetramer positive T cells were isolated from a TCL1-specific T cell line by MACS using TCL1$_{71-78}$ tetramer PE and anti-PE microbeads. The isolated T cells were incubated with T2 cells pulsed with various concentrations of TCL1$_{65-79}$ peptide and IFN-γ production was determined in the supernatants by ELISA after 18 hours. Dot plot shows purity of sorted T cells. Representative data from one of two experiments.

To determine the minimal immunogenic epitope in the TCL1$_{65-79}$ peptide, the inventors generated a panel of peptides truncated progressively by one amino acid at the N- and C-termini and incubated the TCL1$_{65-79}$ peptide-specific T cells with T2 cells pulsed with each of the peptides. The inventors found that TCL1$_{71-78}$ (LLPIMWQL) (SEQ ID NO:11) is the minimal epitope that induced significant IFN-γ production by the TCL1$_{65-79}$ peptide-specific T cells (FIG. 4A). Analysis of the peptides in a standard functional peptide-binding assay using T2 cells demonstrated that the peptides that induced IFN-γ production by the TCL1$_{65-79}$ peptide-specific T cells bound to HLA-A2, including the TCL1$_{71-78}$ peptide (FIG. 4B). Conversely, truncated peptides that did not show significant binding to HLA-A2 did not induce IFN-γ production. To further confirm that the TCL1$_{71-78}$ peptide is the minimal epitope recognized by the TCL1$_{65-79}$ peptide-specific T cells, the inventors performed cytotoxicity assay. TCL1$_{65-79}$ peptide-specific T cells specifically lysed T2 cells pulsed with TCL1$_{70-79}$ (SLLPIMWQL) (SEQ ID NO:10), TCL1$_{71-79}$ (LLPIMWQLY) (SEQ ID NO:8) and TCL1$_{71-78}$ (LLPIMWQL) (SEQ ID NO:11) peptides, but not TCL1$_{71-77}$ (LPIMWQL) (SEQ ID NO:44) peptide, indicating that TCL1$_{71-78}$ (LLPIMWQL) (SEQ ID NO:11) is the minimal epitope recognized by TCL1$_{65-79}$ peptide-specific T cells. Finally, the inventors used a tetramer synthesized with the TCL1$_{71-78}$ peptide and found that 8.2% of the TCL1$_{65-79}$ peptide-specific CD8$^+$ T cells stained tetramer positive (FIG. 4D). By peptide titration experiments, we found that these T cells recognized peptide concentrations as low as 1 nM suggesting that they were of moderate avidity (FIG. 15) (McKee et al., 2005). Together, these results suggested that TCL1$_{71-78}$ peptide is the minimal HLA-A2-binding epitope recognized by CD8$^+$ T cells.

TCL1-Specific T Cells Induced Lysis of Primary Human Lymphoma Cells

Figure 5C:
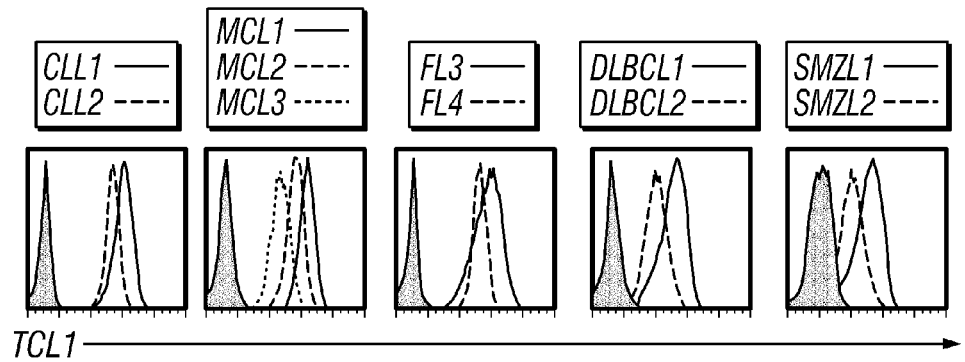
Figure 5D:
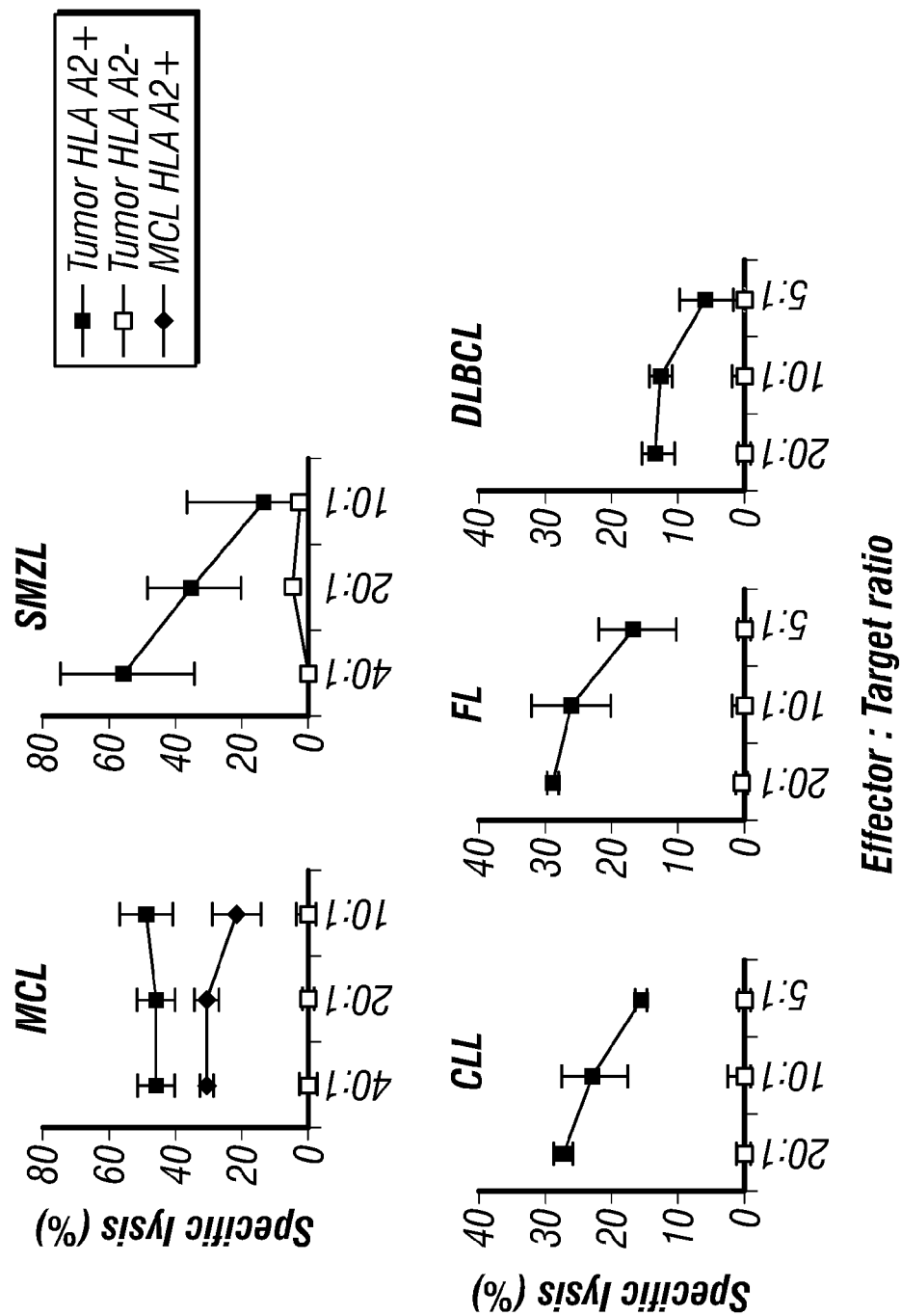
Figure 16A:
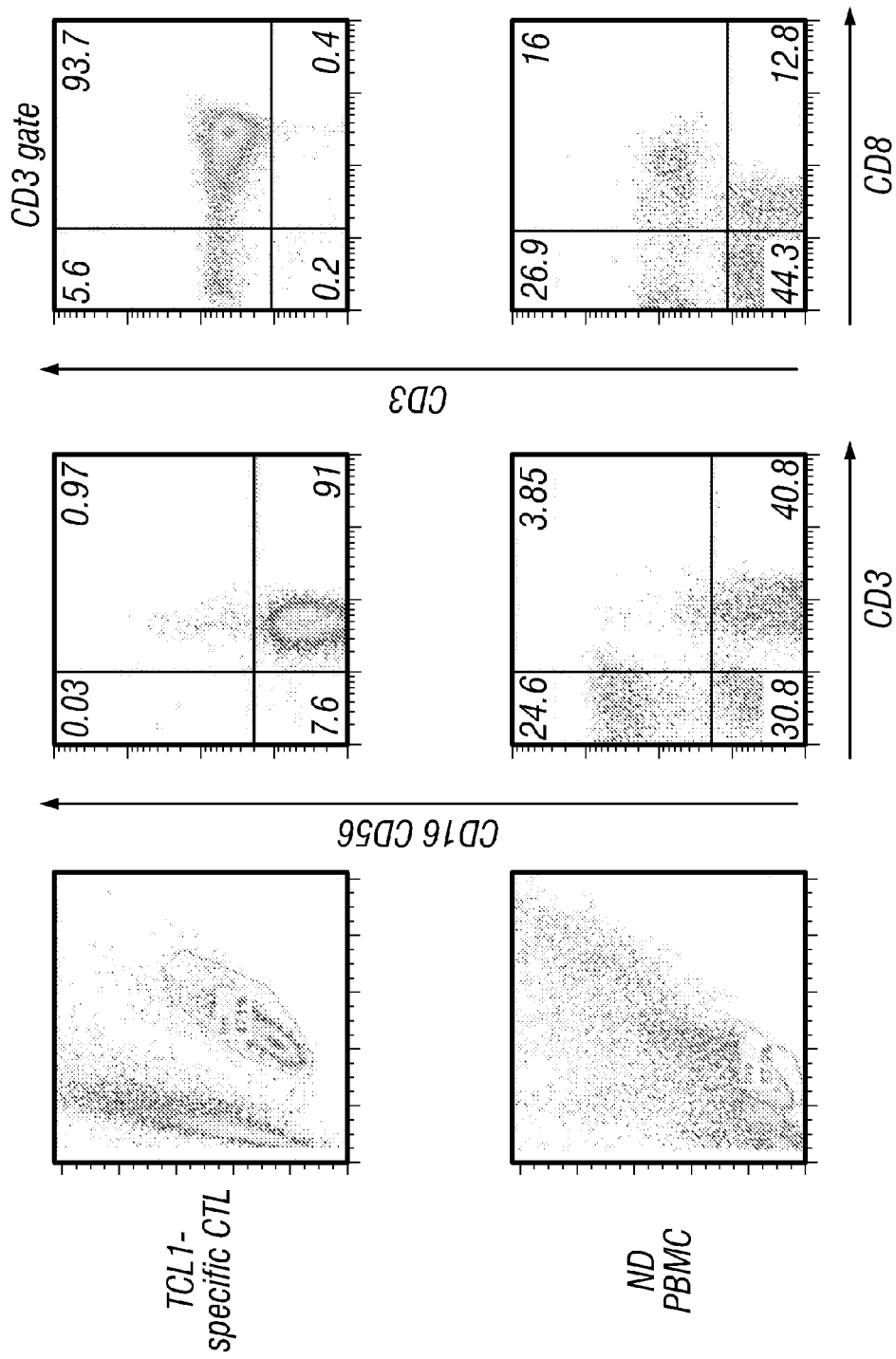
FIGS. 16A-B. Phenotype and specificity of TCL1-specific CTL.
Figure 16B:
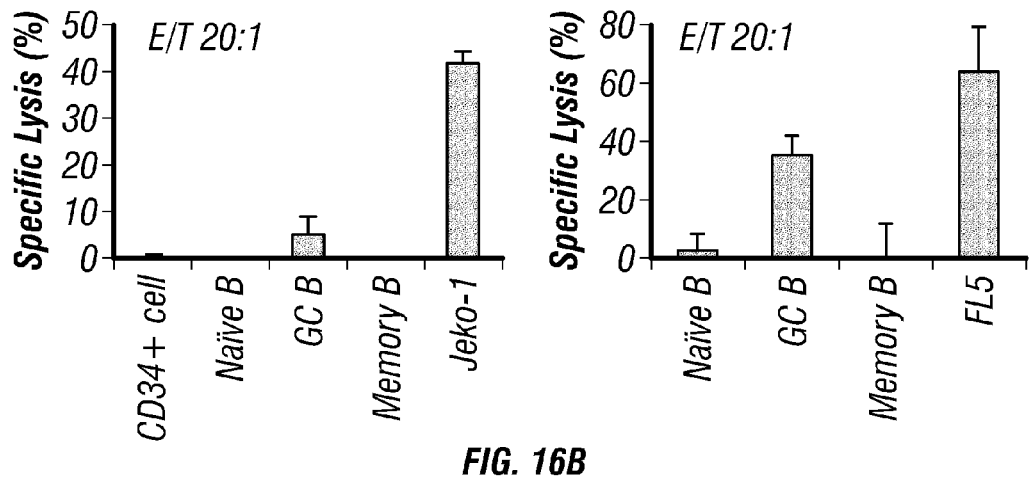

To determine whether endogenous TCL1 is processed and presented by tumor cells, the inventors performed cytotoxicity assay against TCL1-expressing human lymphoma cell lines and primary lymphoma cells. Using flow cytometry, the inventors observed that TCL1 was highly expressed in Mino, Jeko-1, and Daudi lymphoma cell lines and at low levels in normal B cells but not in MCF-7 and K562 cell lines (FIG. 5A). TCL1$_{65-79}$ peptide-specific T cells derived from HLA-A2$^+$ normal donors induced significant lysis of HLA-A2$^+$ TCL1$^+$ Mino and Jeko-1 cells but not HLA-A2$^-$ TCL1$^+$ Daudi cells, HLA-A2$^-$ TCL1$^-$ K562 cells, HLA-A2$^+$ TCL1$^-$ MCF-7 cells, and HLA-A2$^+$ normal donor B cells (FIG. 5B). CD8$^+$ T cells purified from TCL1$_{65-79}$ peptide-specific T cell lines (FIG. 16A) induced significant lysis of HLA-A2$^+$ TCL1$^+$ Mino and Jeko-1 cells but not HLA-A2$^-$TCL1$^+$ Daudi cells, HLA-A2$^-$TCL1$^-$ K562 cells, or HLA-A2$^+$ TCL1$^-$ MCF-7 cells (FIG. 5B). TCL1 was present at low levels in normal donor B cells and consistent with this, TCL1$_{65-79}$ peptide-specific T cells induced very low lysis of HLA-A2$^+$ normal donor B cells. When various normal B cell subsets were used as targets, we found that TCL1-specific T cells had low cytotoxic activity against naïve and GC B cells but not memory B cells (FIG. 16B). Furthermore, consistent with the expression pattern of TCL1 (FIG. 13A), TCL1-specific T cells had no cytotoxic activity against HLA-A2$^+$ CD34$^+$ hematopoietic stem cells (FIG. 16B). Similarly, the inventors observed that the normal donor-derived TCL1$_{65-79}$ peptide-specific T cells induced significant lysis of HLA-A2$^+$ TCL1$^+$ primary tumor cells obtained from patients with FL, CLL, MCL, DLBCL, and SMZL but not HLA-AT TCL1$^+$ tumor cells (FIG. 5C and FIG. 5D). These results suggested that TCL1 is naturally processed and presented on the cell surface by the primary lymphoma cells for recognition by TCL1-specific CD8$^+$ T cells in an HLA-A2 restricted manner.

TCL1$_{71-78}$ Peptide-Specific T Cells can be Generated from Lymphoma Patients

To determine whether TCL1$_{71-78}$ peptide-specific T cells can be generated from lymphoma patients, the inventors stimulated PBMC from a patient with CLL, and PBMC and intratumoral T cells from a patient with FL with TCL1$_{65-79}$ peptide. These patient-derived T-cell lines secreted significant amount of IFN-γ upon incubation with TCL1$_{65-79}$ peptide-pulsed T2 cells (FIG. 6A). Furthermore, these T cells lysed TCL1$_{65-79}$ peptide-pulsed T2 cells at high efficiency but not control peptide-pulsed or unpulsed T2 cells (FIG. 6B). Tetramer staining using TCL1$_{71-78}$ peptide showed that 10.8-23% of the CD8$^+$ T cells were tetramer positive (FIG. 6C). To further confirm the cytotoxic activity of the patient-derived T-cell lines, the inventors incubated the T cells with autologous or allogeneic primary lymphoma cells. The inventors found that the patient-derived TCL1$_{65-79}$ peptide-specific T cells efficiently lysed HLA-A2$^+$ TCL1$^+$ autologous or allogeneic primary lymphoma cells but not HLA-AT TCL1$^+$ lymphoma cells, HLA-A2$^+$ tumor-free PBMC or HLA-A2$^+$ TCL1$^-$ MCF-7 cells (FIG. 6D and FIG. 6E). These results suggested that TCL1-specific CD8$^+$ T cells that specifically recognize the autologous tumor cells could be generated from lymphoma patients.

Figure 7A:
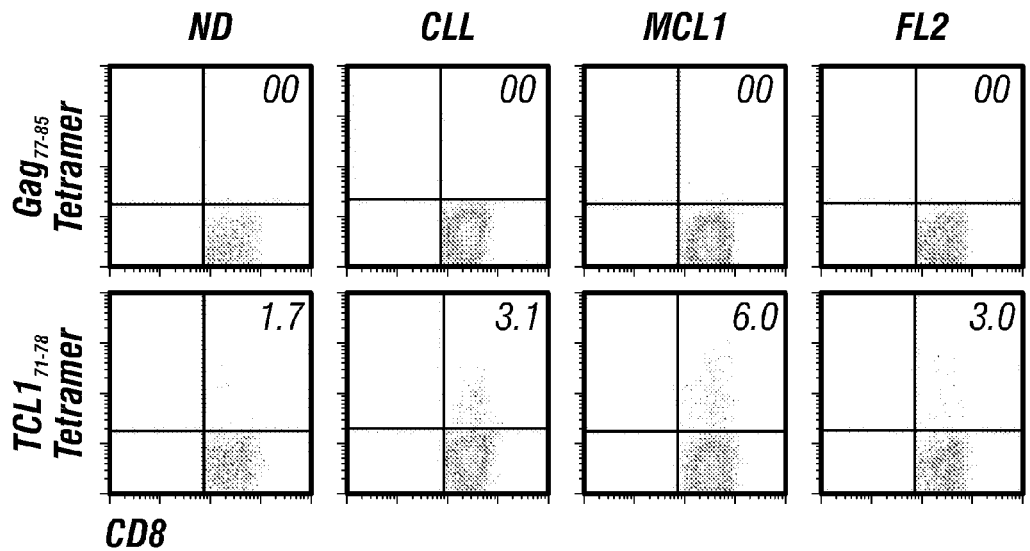
FIGS. 7A-B: TCL1$_{71-78}$ peptide-specific T cells are increased in lymphoma patients. PBMCs from HLA-A2$^+$ normal donors (ND, n=8) or lymphoma patients [chronic lymphocytic leukemia (CLL, n=2), mantle cell lymphoma (MCL, n=5); follicular lymphoma (FL, n=4); diffuse large B-cell lymphoma (n=2); splenic marginal zone B-cell lymphoma (SMZL, n=2)] were stimulated in vitro twice with TCL1$_{65-79}$ peptide and stained with TCL1$_{71-78}$ tetramer or HIV Gag$_{77-85}$ tetramer. Representative data of the tetramer staining (FIG. 7A) and results from all samples analyzed (FIG. 7B) are shown. P value on the top of graph represents comparison between normal donors and all lymphoma patient samples. P values to the right represent comparison between normal donors and patients from each lymphoma subtype. All P values were calculated by two-tailed Student's t test.
Figure 7B:
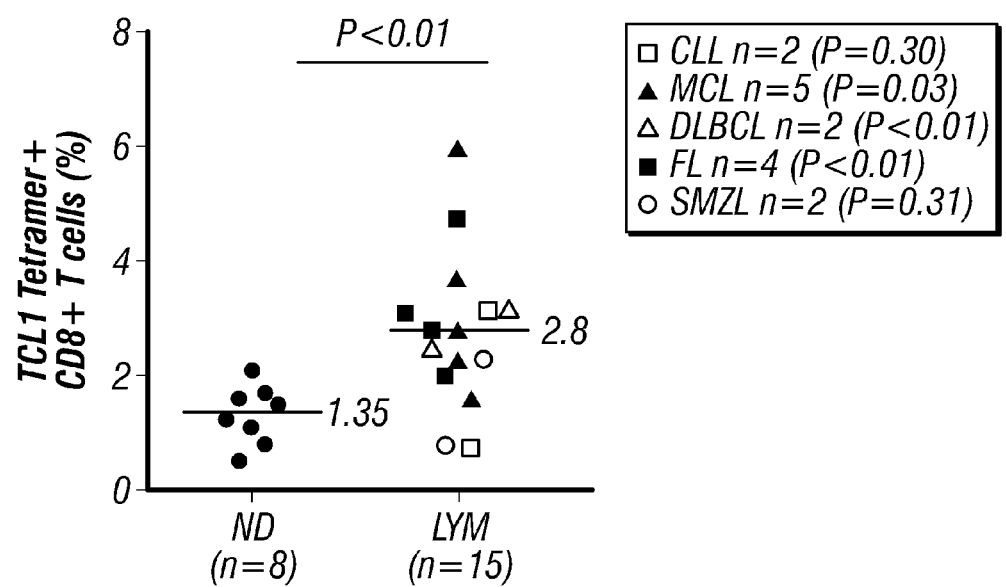
Figure 8:
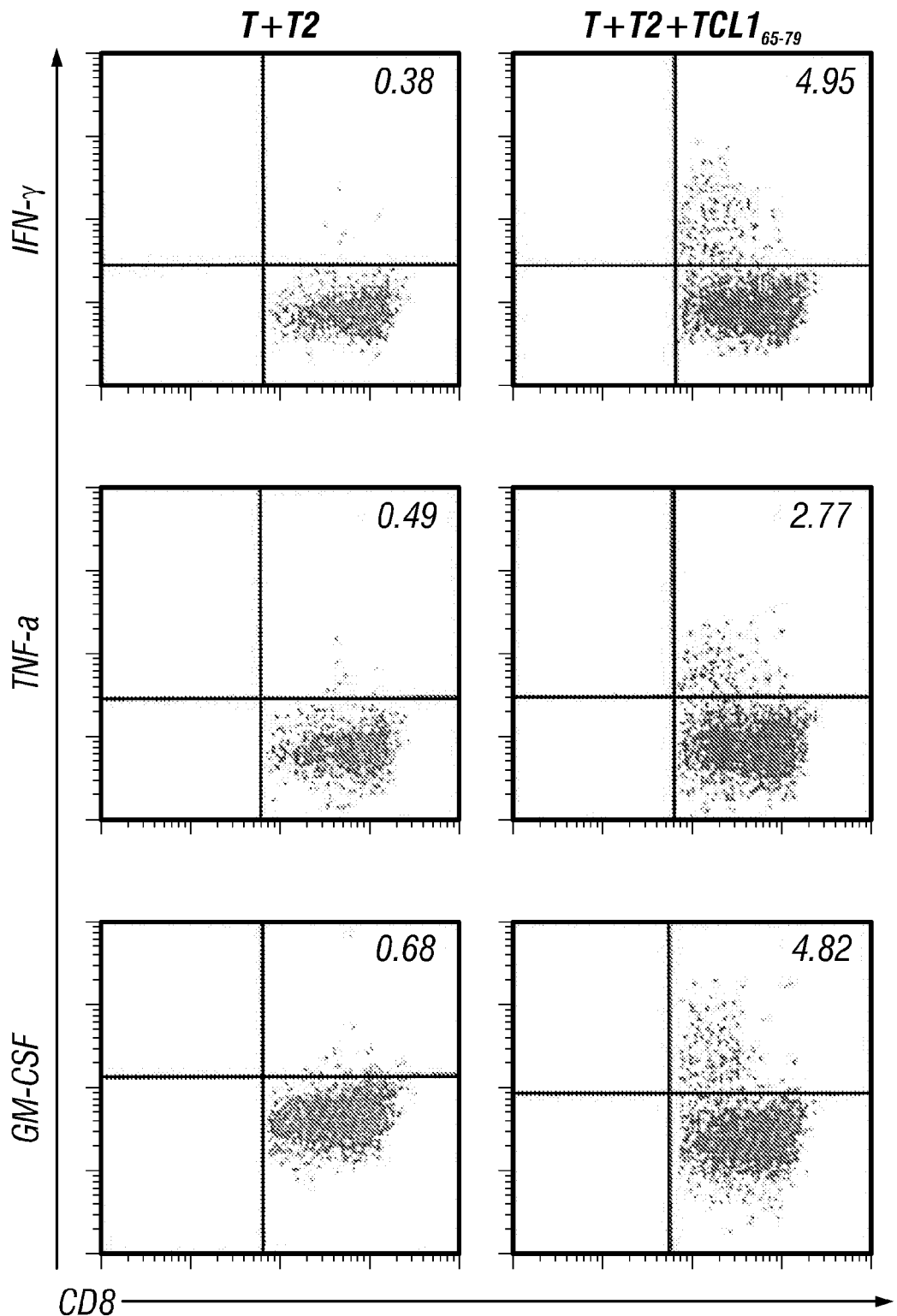
FIG. 8: Cytokine secretion profile of TCL1-specific CTLs. T2 cells were pulsed with TCL1$_{65-79}$ peptide in the presence of 3 ng/ml 132-microglobulin overnight and then incubated with normal donor-derived TCL1-specific CTLs for one hour prior to adding Brefeldin A. The cytokine expression was determined 12 hours later by intracellular staining. TCL1-specific CTLs secreted IFN-γ, GM-CSF, and TNFα but not IL-4, IL-10, and IL-17.
Figure 8:
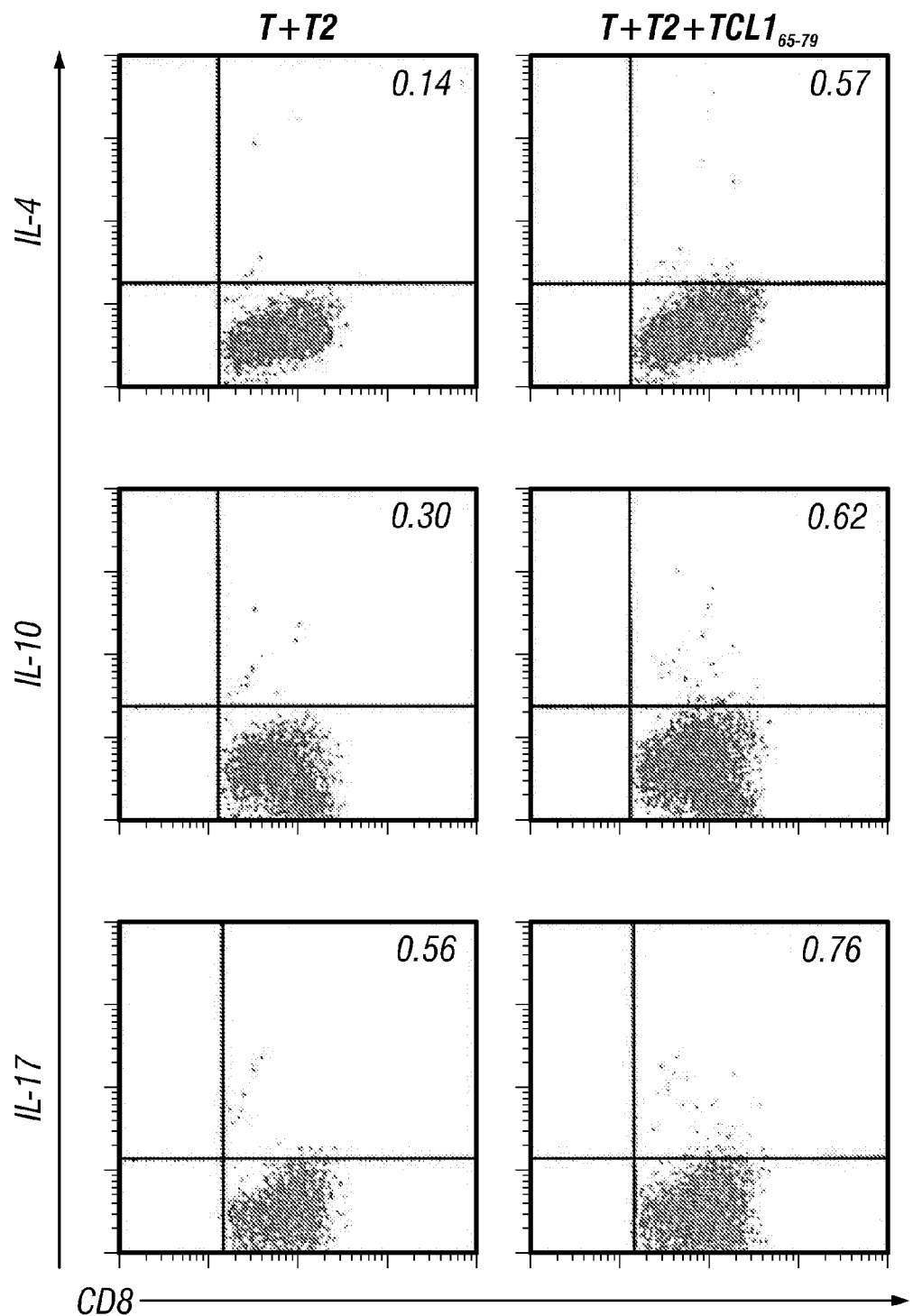
Figure 10:
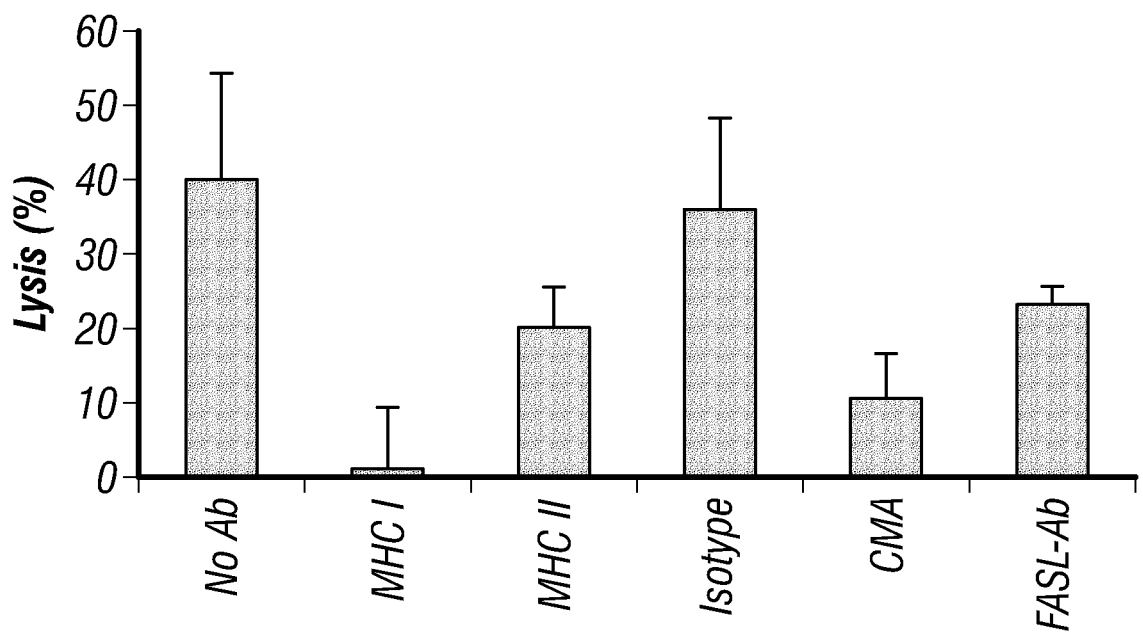
FIG. 10: Mechanism of cytotoxicity of TCL1-specific CTLs against autologous follicular lymphoma cells. TCL1-specific T cells were generated from PBMC obtained from a FL patient and cultured with autologous FL tumor cells pre-incubated with or without 10 μg/ml of MHC class I, class II, and isotype control antibodies at a ratio of 20:1 (Effector: Target). A standard 4 hour chromium-51 release assay was performed. MHC class I but not MHC class II or isotype control antibodies inhibited the cytolysis autologous lymphoma cells. Concanamycin A but not FAS ligand antibody (FASL-Ab) significantly inhibited the cytotoxic ability of TCL1-specific CTLs suggesting that the cytotoxicity is perforin mediated.
Figure 11:
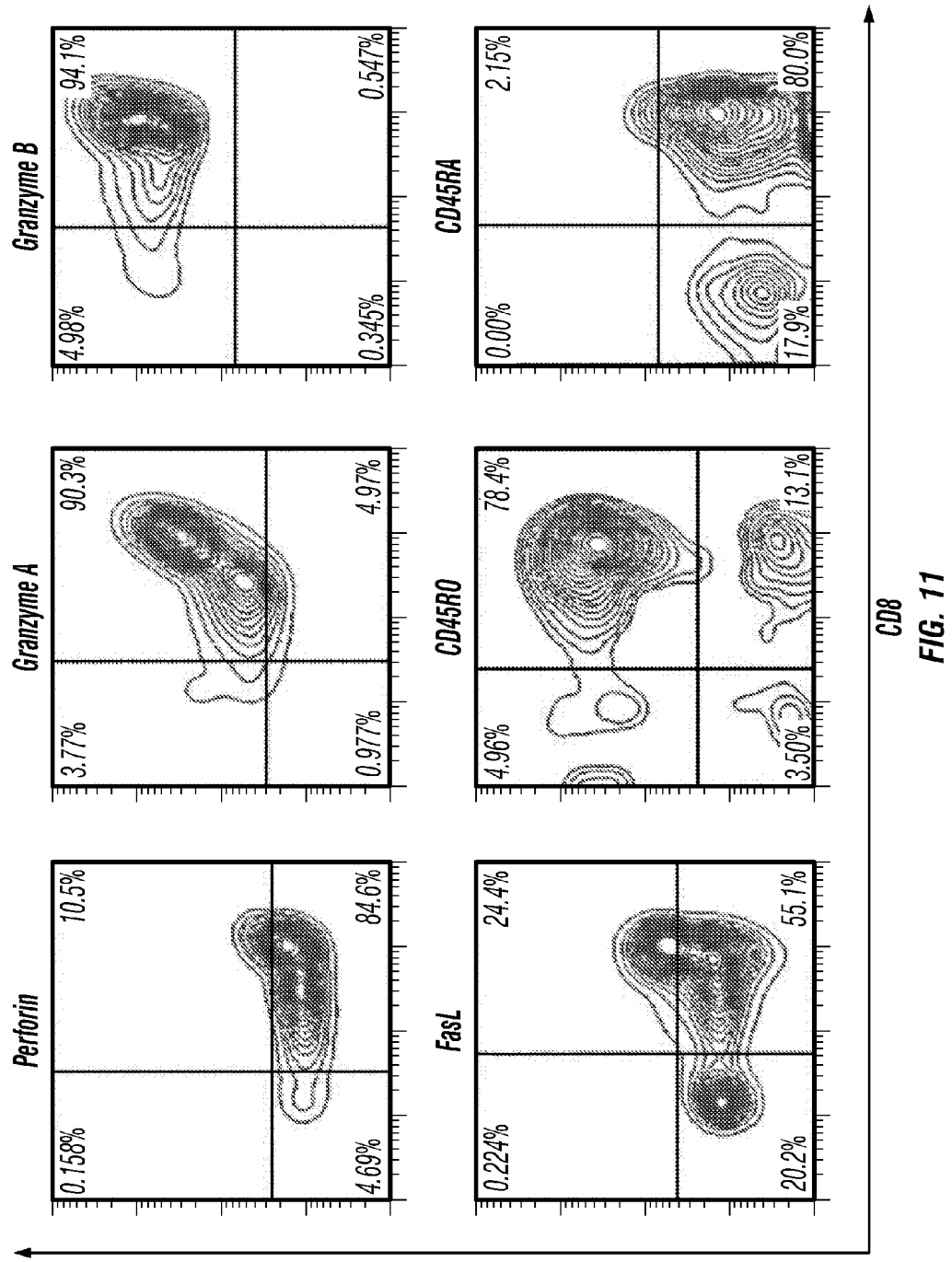
FIG. 11: TCL1-specific CTLs derived from normal donor expressed high levels of Granzyme A, Granzyme B, FAS ligand, and CD45RO but not CD45RA suggesting that they are effector memory T cells.
Figure 12:
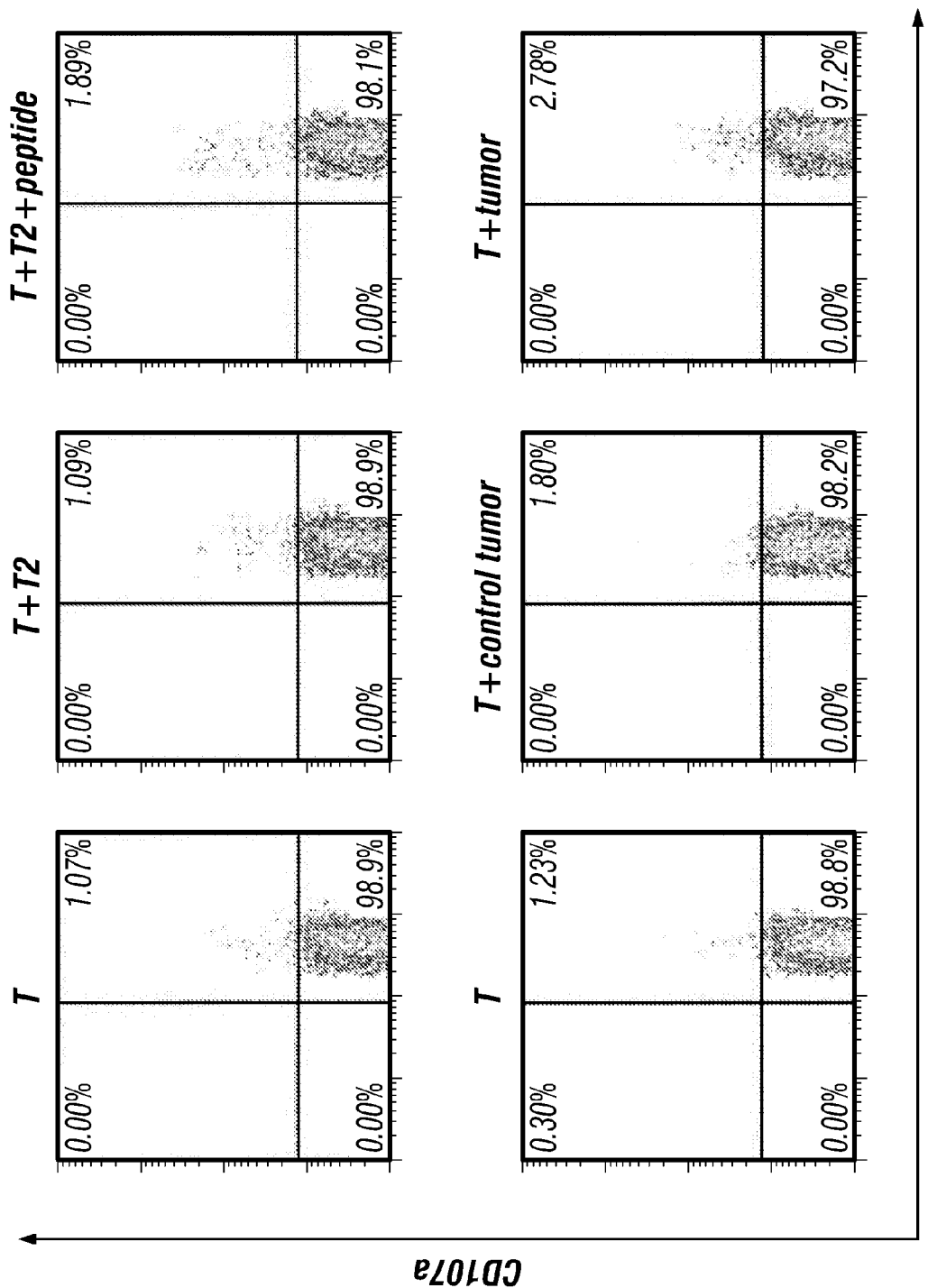
FIG. 12: Expression of CD107a by TCL1-specific CTLs. TCL1-specific CTLs generated from PBMC of a FL patient expressed CD107a when co-cultured with TCL1$_{65-79}$ peptide-pulsed T2 cells or autologous lymphoma cells but not control tumor cells. These results suggest that TCL1-specific CTLs degranulate upon recognition of TCL1-derived peptide.
Figure 17:
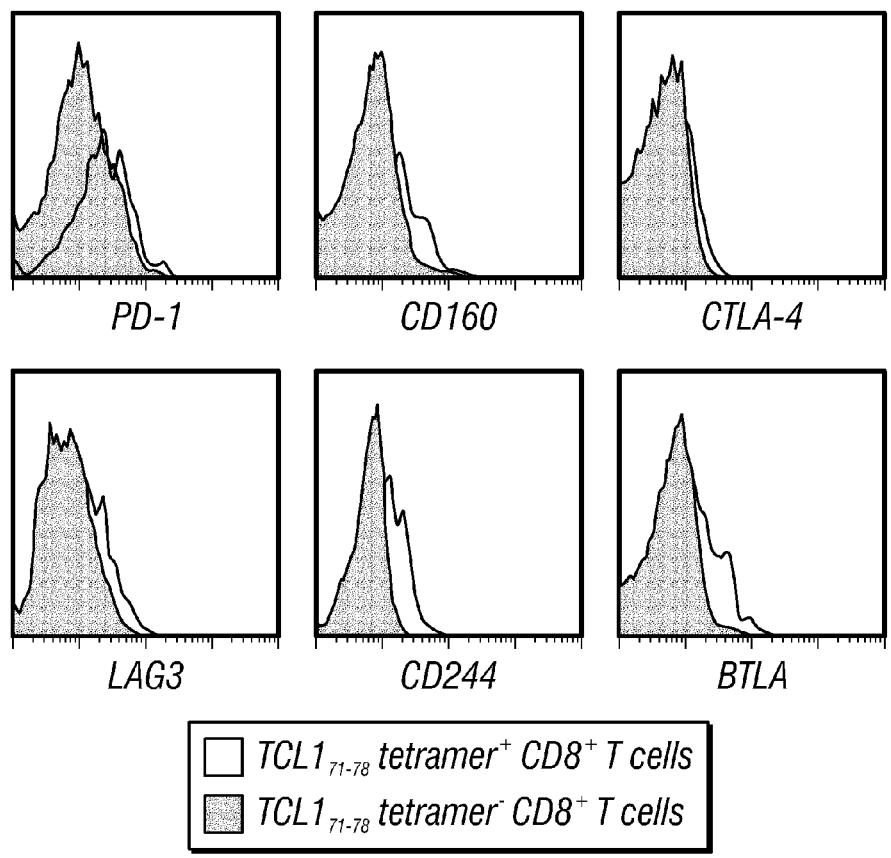
FIG. 17. Expression of coinhibitory molecules on TCL1-specific CTL derived from lymphoma patients. Expression of coinhibitory molecules was determined by flow cytometry on TCL1$_{71-78}$ tetramer$^+$ CD8$^+$ T cells (open histogram) and compared with TCL1$_{71-78}$ tetramer$^-$ CD8$^+$ T cells (grey histogram). Representative data from one of three lymphoma patients is shown.

To determine whether TCL1$_{71-78}$ peptide-specific CD8$^+$ T cells are naturally induced in lymphoma patients, the inventors performed tetramer staining of PBMC derived from HLA-A2$^+$ lymphoma patients at initial diagnosis (N=15) and healthy donors (N=8). As the frequency of TCL1-specific CTL in the unstimulated PBMC was below the threshold of detection by our tetramer assay, we performed two rounds of in vitro stimulation with TCL1$_{65-79}$ peptide.). The inventors found that the percentage of TCL1$_{71-78}$ tetramer positive CD8$^+$ T cells was significantly higher in patients (2.8% median; 0.88-6% range) compared with normal donor PBMC that were similarly stimulated in vitro (1.35% median; 0.38-2.2% range) (P<0.01) (FIGS. 7A-B). These results support the idea that TCL1$_{71-78}$ peptide-specific T cells are naturally induced in HLA-A2$^+$ lymphoma patients. Moreover, these TCL1$_{71-78}$ tetramer positive T cells had low levels of expression of coinhibitory molecules such as PD-1, CD160, CTLA-4, LAG-3, CD244, and BTLA (FIG. 17). These results taken together with the data in FIGS. 6A-E, suggest that the TCL1-specific T cells isolated from lymphoma patients were not exhausted All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,814,097
U.S. Pat. No. 3,817,837
U.S. Pat. No. 3,850,752
U.S. Pat. No. 3,939,350
U.S. Pat. No. 3,964,482
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,373,071
U.S. Pat. No. 4,401,796
U.S. Pat. No. 4,458,066
U.S. Pat. No. 4,472,509
U.S. Pat. No. 4,598,049
U.S. Pat. No. 4,897,268
U.S. Pat. No. 4,938,948
U.S. Pat. No. 5,021,236
U.S. Pat. No. 5,075,109
U.S. Pat. No. 5,196,066
U.S. Pat. No. 5,262,357
U.S. Pat. No. 5,505,928
U.S. Pat. No. 5,552,157
U.S. Pat. No. 5,565,213
U.S. Pat. No. 5,567,434
U.S. Pat. No. 5,656,016
U.S. Pat. No. 5,690,807
U.S. Pat. No. 5,697,899
U.S. Pat. No. 5,738,868
U.S. Pat. No. 5,741,516
U.S. Pat. No. 5,741,957
U.S. Pat. No. 5,750,172
U.S. Pat. No. 5,756,687
U.S. Pat. No. 5,770,219
U.S. Pat. No. 5,770,219
U.S. Pat. No. 5,779,708
U.S. Pat. No. 5,783,208
U.S. Pat. No. 5,795,587
U.S. Pat. No. 5,797,898
U.S. Pat. No. 5,827,690
U.S. Pat. No. 5,990,479
U.S. Pat. No. 6,048,616
U.S. Pat. No. 6,091,001
U.S. Pat. No. 6,274,323
U.S. Pat. No. 6,630,307
U.S. Pat. No. 7,910,109
U.S. Patent Appln. 2005/0065463
Aggarwal et al., *Mod. Pathol.*, 22:206-215, 2008.
Altman et al. *Science* 274(5284):94-6, 1996.
Antibodies: A Laboratory Manual, Cold Spring Harbor Laboratory, 1988.
Atherton et al., *Biol. of Reproduction*, 32, 155-171, 1985.
Baird et al., *Scand. J. Immunol.*, 60(4):363-71, 2004.
Baraldo et al., *Infect. Immun.*, 73(9):5835-41, 2005.
Bendandi et al., *Nat. Med.*, 5:1171-1177, 1999.
Berberian et al., *Science*, 261:1588-1591, 1993.
Bertinetti et al., *Cancer Res.*, 66:4496-4502, 2006.
Bijker et al., *J. Immunol.*, 179:5033-5040, 2007.
Blanchard and Shastri, *Curr. Opin. Immunol.*, 20:82-88, 2008.
Burrows et al., *Trends Immunol.*, 27:11-16, 2006.
Campbell, In: *Monoclonal Antibody Technology, Laboratory Tech. Biochem. Molec. Biol.*, Vol. 13, Burden and Von Knippenberg (Eds.), 75-83, Amsterdam, Elsevier, 1984.
Celluzzi et al., *J. Exp. Med.*, 183 283-287, 1996.
Cheson and Leonard, *N. Eng. J. Med.*, 359:613-626, 2008.
Cleary et al., *J. Biol. Chem.*, 269(29):18747-9, 1994.
Coiffier et al., *N. Eng. J. Med.*, 346:235-242, 2002.
Collins et al., *Nature*, 371:626-629, 1994.
Cumber et al., *J. Immunol.*, 149B:120-126, 1992.
De Jager et al., *Semin. Nucl. Med.* 23(2), 165-179, 1993.
Dholakia et al., *J. Biol. Chem.*, 264, 20638-20642, 1989.
Di Nicola et al., *Blood*, 113:18-27, 2009.
Doolittle and Ben-Zeev, *Methods Mol. Biol.*, 109, 215-237, 1999.
Drin et al., *AAPS Pharm. Sci.*, 4(4):E26, 2002.
Du et al., *J. Pept. Res.*, 51:235-243, 1998.
Dudley et al., *J. Immunol.*, 26(4):332-342, 2003.
Elliott and O'Hare, *Cell*, 88:23-233, 1997.
European Patent 0 216 846
European Patent 0 256 055
European Patent 0 323 997
European Patent Appl. 89303964.4
Frankel and Pabo, *Cell*, 55:189-1193, 1988.
Gefter et al., *Somatic Cell Genet.*, 3:231-236, 1977.
Goding, In: *Monoclonal Antibodies: Principles and Practice*, 2d ed., Orlando, Fla., Academic Press, 60-61, 65-66, 71-74, 1986.
Goeddel, *Methods Enzymol.*, 185:3-7, 1990.
Gritti et al., *Blood*, 92:368-373, 1998.
Gulbis and Galand, *Hum. Pathol.* 24(12), 1271-1285, 1993.
Guo et al., *Nature*, 360:364-366, 1992.
Gupta et al., *Biomaterials*, 26:3995-4021, 2005.
Hawkins et al., *Hum. Gene Ther.*, 21(6):665-72, 2010.
Herling et al., *Am. J. Surg. Pathol.*, 31:1123-1129, 2007.
Herling et al., *Blood*, 114(21):4675-4686, 2009.
Hida et al., *Cancer Immunol. Immunotherapy*, 51:219-228, 2002.
Houot and Levy, *Blood Rev.*, 23:137-142, 2009.
Hoyer et al., *J. Immunol.*, 175:864-873, 2005.
Hoyer et al., *Proc. Natl. Acad. Sci. USA*, 99:14392-14397, 2002.
Inoges et al., *J. Natl. Cancer Inst.*, 98:1292-1301, 2006.
Irvine et al., *Nature*, 419:845-849, 2002.
Kang et al., *Blood*, 105:1288-1294, 2005.
Kang et al., *Science*, 240:1034-1036, 1988.
Khatoon et al., *Ann. of Neurology*, 26, 210-219, 1989.
King et al., *J. Biol. Chem.*, 269, 10210-10218, 1989.
Kohler and Milstein, *Eur. J. Immunol.*, 6, 511-519, 1976.
Kohler and Milstein, *Nature*, 256, 495-497, 1975.
Kohler et al., *Methods Enzymol.*, 178:3, 1989.
Kreier et al., In: *Infection, Resistance and Immunity*, Harper and Row, New York, 1991.
Kwak et al., *N. Eng. J. Med.*, 327:1209-1215, 1992.
Laine et al., *Molec. Cell*, 6:395-407, 2000.
Lee et al., *J. Immunol. Methods*, 331:13-26, 2008.
Lenert et al., *Science*, 248:1639-1643, 1990.
Lin et al., *Immunol. Cell Biol.*, 86:353-362, 2008.
Lin et al., *J. Biol. Chem.*, 270:4255-14258, 1995.
Liu et al., *Cell Mol. Biol.*, 49(2):209-216, 2003.
Malyguine et al., *J. Transl. Med.*, 2:9, 2004.
Marcus et al., *Blood*, 105:1417-1423, 2005.
Maus et al., *Nat. Biotech.*, 20:143-148, 2002.
McKee et al., *J Transl Med.* 3:35, 2005.
McLaughlin et al., *J. Clin. Oncol.*, 16:2825-2833, 1998.
Melief and van der Burg, *Nat. Rev. Cancer*, 8:351-360, 2008.
Moorthy et al., *PLoS Med.*, 1(2):e33, 2004.

Nakamura et al., In: *Enzyme Immunoassays: Heterogeneous and Homogeneous Systems*, Chapter 27, 1987.
Narducci et al., *Cancer Res.*, 57:5452-5456, 1997b.
Narducci et al., *Cancer Res.*, 60:2095-2100, 2000.
Narducci et al., *Oncogene*, 15:919-926, 1997a.
Narducci et al., *Proc. Natl. Acad. Sci. USA*, 99:11712-11717, 2002.
Navarrete et al., *Blood*, 117:1483-1491, 2011.
Neelapu et al., *Nat. Med.*, 11:986-991, 2005.
Neelapu et al., *Blood*, 15:109(12):5160-5163, 2007.
Nestle et al., *Nat. Med.*, 4:328, 1998.
O'Shannessy et al., *J. Immun. Meth.*, 99, 153-161, 1987.
Owens and Haley, *J. Biol. Chem.*, 259, 14843-14848, 1987.
Pack et al., *Biochem.*, 31:1579-1584, 1992.
Park and Neelapu, *Br. J. Haemat.*, 142:179-191, 2008.
PCT Publn. WO 99/26299
Pekarsky et al., *Proc. Natl. Acad. Sci. USA*, 105:19643-19648, 2008.
Popescu et al. *Blood*, 15:109(12):5407-5410, 2007.
Potter and Haley, *Meth. Enzymol.*, 91, 613-633, 1983.
Quintarelli et al., *Blood*, 117:3353-3362, 2011.
Ramuz et al., *Int. J Oncol.*, 26:151-157, 2005.
Remington, In: *The Science and Practice of Pharmacy*, 21$^{st}$ Ed., Lippincott Williams and Wilkins, 2005.
Remington, In: *The Science and Practice of Pharmacy*, 21$^{st}$ Ed., Pharmaceutical Press, 2011.
Ribas et al., *Trends Immunol.*, 24:58-61, 2003.
Riddell et al., *J. Immunol.*, 128(2):189-201, 1990.
Rojas et al., *J. Biol. Chem.*, 271:27456-27461, 1996.
Rojas et al., *Proc. West. Pharmacol. Soc.*, 41:55-56, 1998.
Said et al., *Lab. Invest.* 81:555-564, 2001.
Samino et al., *J. Biol. Chem.*, 281:6358-6365, 2006.
Sasso et al., *J. Immunol.*, 142:2778-2783, 1989.
Schuster et al., *J. Clin. Oncol.*, 29(20):2787-94, 2011.
Schwarze et al., *Trends in Cell Biol.*, 10:290-295, 2000.
Schwenzer et al., *J. Biol. Chem.*, 274:19368-19374, 1999.
Shorki et al., *J. Immunol.*, 146:936-940, 1991.
Silvermann et al., *J. Clin. Invest.*, 96:417-426, 1995.
Skull and Kemp, *Arch. Dis. Child.*, 74:527-530, 1996.
Stryhn et al., *Eur. J. Immunol.*, 30:3089-3099, 2000.
Teitell, *Nat. Rev. Cancer*, 5:640-648, 2005.
Timmerman et al., *Blood*, 99:1517-1526, 2002.
Virgilio et al., *Proc. Natl. Acad. Sci. USA*, 95:3885-3889, 1998.
Wakim et al., *Nature*, 471:629-632, 2011.
Wang and Wang, *Nat. Biotechnol.*, 20:149-154, 2002.
Yoo et al., *J. Immunol. Methods*, 261(1-2):1-20, 2002.
Young et al., *J. Exp. Med.*, 183:-11, 1996.
Zwaveling et al., *J. Immunol.*, 169:350-358, 2002.

The invention claimed is:

1. An isolated peptide 20 amino acids in length or less and comprising the sequence of $TCL1_{65-78}$ (SEQ ID NO:2) or $TCL1_{71-78}$ (SEQ ID NO:11) or a sequence having at least 90% identity to $TCL1_{65-78}$ (SEQ ID NO:2) or $TCL1_{71-78}$ (SEQ ID NO:11), wherein the peptide selectively binds HLA-A2 or HLA-A*0201.

2. The peptide of claim 1, wherein the peptide is 15 amino acids in length or less.

3. The peptide of claim 1, wherein the peptide comprises $TCL1_{65-79}$ (SEQ ID NO:1).

4. The peptide of claim 3, wherein the peptide consists of $TCL1_{65-79}$ (SEQ ID NO:1).

5. The peptide of claim 1, wherein the peptide comprises $TCL1_{70-79}$ (SEQ ID NO:7).

6. The peptide of claim 1, wherein the peptide is comprised in a pharmaceutical preparation.

7. The peptide of claim 6, wherein the pharmaceutical preparation is formulated for parenteral administration, intravenous injection, intramuscular injection, inhalation, or subcutaneous injection.

8. The peptide of claim 7, wherein the peptide is comprised in a liposome, lipid-containing nanoparticle, or in a lipid-based carrier.

9. The peptide of claim 8, wherein the pharmaceutical preparation is formulated for injection or inhalation as a nasal spray.

10. The peptide of claim 1, wherein the peptide is comprised in a cell culture media.

11. The peptide of claim 1, wherein the peptide was produced via peptide synthesis.

12. The peptide of claim 1, wherein the peptide was recombinantly produced.

13. An in vitro method for inducing a population of T cells to proliferate, comprising contacting T cells in vitro with a peptide of claim 1 in an amount sufficient to bind a HLA-A*0201 or a HLA-A2 in the T cells and promote proliferation of one or more of the T cells.

14. A method of promoting an immune response in a subject against TCL1, comprising administering to the subject a peptide of claim 1 in an amount effective to cause proliferation of T cells that selectively target TCL1, wherein said TCL1 is expressed by a cell in the subject, wherein the cell is a B-cell malignancy, a leukemia, or a lymphoma.

15. An isolated nucleic acid encoding the peptide of claim 1.

16. A vector comprising a contiguous sequence consisting of the nucleic acid segment of claim 15.

17. An isolated antibody that selectively binds to the peptide of claim 1.

18. A kit comprising the peptide of claim 1 in a container.

* * * * *

UNITED STATES PATENT AND TRADEMARK OFFICE
CERTIFICATE OF CORRECTION

PATENT NO. : 9,290,541 B2
APPLICATION NO. : 14/358896
DATED : March 22, 2016
INVENTOR(S) : Sattva S. Neelapu and Jinsheng Weng Page 1 of 1

It is certified that error appears in the above-identified patent and that said Letters Patent is hereby corrected as shown below:

In the Specification:

Column 1, lines 9-11, delete paragraph and insert --This invention was made with government support under K23CA123149 and CA16672 awarded by the National Institutes of Health. The government has certain rights in the invention.-- therefor.

Signed and Sealed this
Nineteenth Day of July, 2016

Michelle K. Lee
*Director of the United States Patent and Trademark Office*

```
                        SEQUENCE LISTING

<160> NUMBER OF SEQ ID NOS: 44

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Thr Gln Ile Gly Pro Ser Leu Leu Pro Ile Met Trp Gln Leu Tyr
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

<400> SEQUENCE: 2

Thr Gln Ile Gly Pro Ser Leu Leu Pro Ile Met Trp Gln Leu
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide

<400> SEQUENCE: 3

Gln Ile Gly Pro Ser Leu Leu Pro Ile Met Trp Gln Leu Tyr
1               5                   10

<210> SEQ ID NO 4
<211> LENGTH: 13
<212> TYPE: PRT
<213> ORGANISM: Artificial Sequence
<220> FEATURE:
```

<223> OTHER INFORMATION: Synthetic peptide

<400> SEQUENCE: 4

Ile Gly Pro Ser Leu Leu Pro Ile Met Trp Gln Leu Tyr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5

Gly Pro Ser Leu Leu Pro Ile Met Trp Gln Leu Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide

<400> SEQUENCE: 6

Pro Ser Leu Leu Pro Ile Met Trp Gln Leu Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Ser Leu Leu Pro Ile Met Trp Gln Leu Tyr
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Leu Leu Pro Ile Met Trp Gln Leu Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Leu Pro Ile Met Trp Gln Leu Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 10

Ser Leu Leu Pro Ile Met Trp Gln Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Leu Leu Pro Ile Met Trp Gln Leu
1               5

<210> SEQ ID NO 12
<211> LENGTH: 13
<212> TYPE: PRT
<213> ORGANISM: Artificial Sequence
<220> FEATURE:
<223> OTHER INFORMATION: Synthetic peptide

<400> SEQUENCE: 12

Thr Gln Ile Gly Pro Ser Leu Leu Pro Ile Met Trp Gln
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Thr Gln Ile Gly Pro Ser Leu Leu Pro Ile Met Trp
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Thr Gln Ile Gly Pro Ser Leu Leu Pro Ile Met
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Thr Gln Ile Gly Pro Ser Leu Leu Pro Ile
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 16

Thr Gln Ile Gly Pro Ser Leu Leu Pro
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Thr Gln Ile Gly Pro Ser Leu Leu
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Leu Pro Ile Met Trp Gln Leu
1               5

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Met Ala Glu Cys Pro Thr Leu Gly Glu Ala Val Thr Asp His Pro
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

Pro Thr Leu Gly Glu Ala Val Thr Asp His Pro Asp Arg Leu Trp
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Glu Ala Val Thr Asp His Pro Asp Arg Leu Trp Ala Trp Glu Lys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22
```

```
Asp His Pro Asp Arg Leu Trp Ala Trp Glu Lys Phe Val Tyr Leu
1               5                   10                  15
```

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

```
Arg Leu Trp Ala Trp Glu Lys Phe Val Tyr Leu Asp Glu Lys Gln
1               5                   10                  15
```

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

```
Trp Glu Lys Phe Val Tyr Leu Asp Glu Lys Gln His Ala Trp Leu
1               5                   10                  15
```

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

```
Val Tyr Leu Asp Glu Lys Gln His Ala Trp Leu Pro Leu Thr Leu
1               5                   10                  15
```

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

```
Glu Lys Gln His Ala Trp Leu Pro Leu Thr Ile Glu Ile Lys Asp
1               5                   10                  15
```

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

```
Ala Trp Leu Pro Leu Thr Ile Glu Ile Lys Asp Arg Leu Gln Leu
1               5                   10                  15
```

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

```
Leu Thr Ile Glu Ile Lys Asp Arg Leu Gln Leu Arg Val Leu Leu
1               5                  10                  15
```

<210> SEQ ID NO 29
<211> LENGTH: 15
<212> TYPE: PRT
<213> ORGANISM: Artificial Sequence
<220> FEATURE:
<223> OTHER INFORMATION: Synthetic peptide

<400> SEQUENCE: 29

```
Ile Lys Asp Arg Leu Gln Leu Arg Val Leu Leu Arg Arg Glu Asp
1               5                  10                  15
```

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

```
Leu Gln Leu Arg Val Leu Leu Arg Arg Glu Asp Val Val Leu Gly
1               5                  10                  15
```

<210> SEQ ID NO 31
<211> LENGTH: 15
<212> TYPE: PRT
<213> ORGANISM: Artificial Sequence
<220> FEATURE:
<223> OTHER INFORMATION: Synthetic peptide

<400> SEQUENCE: 31

```
Val Leu Leu Arg Arg Glu Asp Val Val Leu Gly Arg Pro Met Thr
1               5                  10                  15
```

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide

<400> SEQUENCE: 32

```
Arg Glu Asp Val Val Leu Gly Arg Pro Met Thr Pro Thr Gln Ile
1               5                  10                  15
```

<210> SEQ ID NO 33
<211> LENGTH: 15
<212> TYPE: PRT
<213> ORGANISM: Artificial Sequence
<220> FEATURE:
<223> OTHER INFORMATION: Synthetic peptide

<400> SEQUENCE: 33

```
Val Leu Gly Arg Pro Met Thr Pro Thr Gln Ile Gly Pro Ser Leu
1               5                  10                  15
```

<210> SEQ ID NO 34
<211> LENGTH: 15
<212> TYPE: PRT
<213> ORGANISM: Artificial Sequence
<220> FEATURE:
<223> OTHER INFORMATION: Synthetic peptide

<400> SEQUENCE: 34

```
Pro Met Thr Pro Thr Gln Ile Gly Pro Ser Leu Leu Pro Ile Met
```

<210> SEQ ID NO 35
<211> LENGTH: 15
<212> TYPE: PRT
<213> ORGANISM: Artificial Sequence
<220> FEATURE:
<223> OTHER INFORMATION: Synthetic peptide

<400> SEQUENCE: 35

Pro Ser Leu Leu Pro Ile Met Trp Gln Leu Tyr Pro Asp Gly Arg
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic peptide

<400> SEQUENCE: 36

Pro Ile Met Trp Gln Leu Tyr Pro Asp Gly Arg Tyr Arg Ser Ser
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic peptide

<400> SEQUENCE: 37

Gln Leu Tyr Pro Asp Gly Arg Tyr Arg Ser Ser Asp Ser Ser Phe
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic peptide

<400> SEQUENCE: 38

Asp Gly Arg Tyr Arg Ser Ser Asp Ser Ser Phe Trp Arg Leu Val
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic peptide

<400> SEQUENCE: 39

Arg Ser Ser Asp Ser Ser Phe Trp Arg Leu Val Tyr His Ile Lys
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide

<400> SEQUENCE: 40

Ser Ser Phe Trp Arg Leu Val Tyr His Ile Lys Ile Asp Gly Val
1               5                   10                  15

```
<210> SEQ ID NO 41
<211> LENGTH: 15
<212> TYPE: PRT
<213> ORGANISM: Artificial Sequence
<220> FEATURE:
<223> OTHER INFORMATION: Synthetic peptide

<400> SEQUENCE: 41

Arg Leu Val Tyr His Ile Lys Ile Asp Gly Val Glu Asp Met Leu
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic peptide

<400> SEQUENCE: 42

His Ile Lys Ile Asp Gly Val Glu Asp Met Leu Leu Glu Leu Leu
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: Synthetic peptide

<400> SEQUENCE: 43

Asp Gly Val Glu Asp Met Leu Leu Glu Leu Leu Pro Asp Asp
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Leu Pro Ile Met Trp Gln Leu
1               5
```